US010006050B2

(12) United States Patent
Mebatsion et al.

(10) Patent No.: US 10,006,050 B2
(45) Date of Patent: *Jun. 26, 2018

(54) RECOMBINANT POXVIRAL VECTORS EXPRESSING BOTH RABIES AND OX40 PROTEINS, AND VACCINES MADE THEREFROM

(71) Applicant: MERIAL, INC., Duluth, GA (US)

(72) Inventors: Teshome Mebatsion, Watkinsville, GA (US); Jules Maarten Minke, Nice (FR); Frederic David, Watkinsville, GA (US)

(73) Assignee: MERIAL, INC., Duluth, GA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/410,588

(22) Filed: Jan. 19, 2017

(65) Prior Publication Data

US 2017/0137843 A1    May 18, 2017

Related U.S. Application Data

(63) Continuation of application No. 13/767,603, filed on Feb. 14, 2013, now Pat. No. 9,567,606.

(Continued)

(51) Int. Cl.
*C12N 15/63* (2006.01)
*C12N 15/86* (2006.01)
(Continued)

(52) U.S. Cl.
CPC ............ *C12N 15/86* (2013.01); *A61K 39/008* (2013.01); *A61K 39/12* (2013.01); *A61K 39/205* (2013.01);
(Continued)

(58) Field of Classification Search
None
See application file for complete search history.

(56) References Cited

U.S. PATENT DOCUMENTS 5,756,103 A    5/1998  Paoletti et al.
6,309,647 B1  10/2001  Paoletti et al.
(Continued)

FOREIGN PATENT DOCUMENTS

CN         101884793        6/2010

OTHER PUBLICATIONS

Perkus et al. Cloning and expression of foreign genes in vaccinia virus, using a host range selection system.J Virol. Sep. 1989;63(9):3829-36.*

(Continued)

*Primary Examiner* — Michelle S Horning
(74) *Attorney, Agent, or Firm* — Judy Jarecki-Black; Richard Seeger; Merial Inc.

(57) ABSTRACT

The present invention provides vectors that contain and co-express in vivo or in vitro immunogenic polypeptides or antigens together with an OX40L polypeptide, which functions as a genetic adjuvant. Together, the immunogenic polypeptide and the OX40L polypeptide elicit an immune response in animal or human, which is greater than the immune response elicited by the immunogenic polypeptide alone. In a particular example, the invention provides vectors encoding a Rabies G immunogenic polypeptide and a canine OX40L genetic adjuvant, which vectors elicit strong immune responses in canine against rabies virus.

20 Claims, 30 Drawing Sheets

Related U.S. Application Data

(60) Provisional application No. 61/598,610, filed on Feb. 14, 2012.

(51) Int. Cl.

| | | |
|---|---|---|
| *C12N 15/863* | (2006.01) | |
| *A61K 39/008* | (2006.01) | |
| *A61K 39/12* | (2006.01) | |
| *A61K 39/39* | (2006.01) | |
| *A61K 39/205* | (2006.01) | |
| *A61K 39/00* | (2006.01) | |

(52) U.S. Cl.
CPC .......... *A61K 39/39* (2013.01); *C12N 15/8633* (2013.01); *A61K 2039/5256* (2013.01); *A61K 2039/53* (2013.01); *A61K 2039/552* (2013.01); *A61K 2039/55516* (2013.01); *C12N 2710/24043* (2013.01); *C12N 2760/20134* (2013.01)

(56) References Cited

U.S. PATENT DOCUMENTS

| | | |
|---|---|---|
| 7,794,736 B2 | 9/2010 | Fischer |
| 8,008,268 B2 | 8/2011 | Yao et al. |
| 8,980,280 B2 | 3/2015 | Poulet et al. |
| 9,567,606 B2 * | 2/2017 | Mebatsion ........... A61K 39/008 |
| 2004/0071675 A1 | 4/2004 | Mazarakis |
| 2013/0209511 A1 | 8/2013 | Mebatsion et al. |

OTHER PUBLICATIONS

Fang et al. Expression of vaccinia E3L and K3L genes by a novel recombinant canarypox HIV vaccine vector enhances HIV-1 pseudovirion production and inhibits apoptosis in human cells. Virology. Dec. 20, 2001;291(2):272-84.*

UniProtKB—E2RP79 (E2RP79_CANLF) 2010.*

Liu J et al. "CD40L expressed from the canarypox vector, ALVAC, can boost immunogenicity of HIV-1 canarypox vaccine in mice and enhance the in vitro expansion of viral specific CD8+ T cell memory responses from HIV-1-infected and HIV-1-uninfected individuals." Vaccine 26 (2008) 4062-4072.

Faber et al. "Overexpression of the Rabies Virus Glycoprotein Results in Enhancement of Apoptosis and Antiviral Immune Response." Journal of Virology, Apr. 2002, p. 3374-3381. vol. 76, No. 7.

Liu J et al. "The adjuvancy of OX40 ligand (CD252) on an HIV-1 canarypox vaccine." Vaccine 27 (2009) 5077-5084.

Serghides L et al. "Evaluation of OX40 Ligand as a Costimulator of Human Antiviral Memory CD8 T Cell Responses Comparison with B7.1 and 4-1BBL." J Immunol 2005;175;6368-6377.

* cited by examiner

Fragment of vCP3006

Fragment of vCP3006 Sequence Key (complete sequence is as set forth in SEQ ID NO:2):
1st BLACK Text: C3 Right arm (SEQ ID NO:3)
*1st GREY Text: I3L promoter (SEQ ID NO:4)*
2nd BLACK Text: Synthetic Rabies G (SEQ ID NO:5)
*2nd GREY Text: C3 right arm (SEQ ID NO:6)*
Underlined Text is cloning VECTOR sequence GCTTTATGAAGAGGAGGATTTTTACATTTTAAAATATCGGCACCGTGTTCTAGTAATAATTTTA
CCATTTCTATATCAGAAATACTTACGGCTAAATACAAAGACGTTGATAGTATATTTACGTTATT
GTATTTGCATTTTTTAAGTATATACCTTACTAAATTTATATCTCTATACCTTATAGCTTTATGC
AGTTCATTTATAAGTCTTCCATTACTCATTTCTGGTAATGAAGTATTATATATCATTATGATAT
TATCTCTATTTTATTCTAATAAAAACCGTTATCATGTTATTTATTATTTGTTATAATTATACTA
TTTAATAAATTATACCAAATACTTAGATACTTATTAATACCATCCTAGAACTTGTATTTCTTGC
CCCCTAAACTTGGACATGCACTCCATTAGGCGTTTCTTGTTTTCGACATCGTCCTCCTTAACAT
ATCCTACTGTTATGTGAGGATTCCACGGATTATCTACTGTGATATCACCAAACACGTCCTTCGA
ACAGGGTACCGCATTCAGCAGAACATTTCTTAGGGCTCTAAGTTCATCAGATACCTCCAGTTTC
ATAACTACAGCGCATCCTTTCGCTCCCAACTGTTTAGAGGCGTTACTCTGAGGAAAACACATCT
CTTCTTTACAGACTATAGAAATAGTCTGTAAATCTTGATCAGTTATTTGCTTTTTGAAATTTTC
AAATCTATCACATTGATCCATATTTGCTATTCCAAGAGTTATATGAGGAAAAATATCACATCCT
GTCATGTATTTTATTGTAACATTATTATAATCTGTAACATCAGTATCTAACCTAACGTCGTAAA
AGTTAACAGATGCCCAGTTACTATAATCCCAAGGAACCTTAACATCTAATCCCATTAAAATAGT
ATCCTTTCTACTATTTTTTTCATTGGCAAGTATGTGGCTTAGTTTACACAAAATTCCTGCCATT
TTGTAACGATAGCGAAGCAATAGCTTGTATG<u>CTTTTTATTTGATTAACTAGTCATAAAAATCGG
GATCCCTCGAG</u>*ATGAGATAAAGTGAAAATATATATCATTATATTACAAAGTACAATTATTTAGG
TTTAATC*ATGGTGCCCCAGGCCCTGCTGTTCGTGCCCCTGCTGGTGTTCCCCCTGTGCTTCGGC
AAGTTCCCCATCTACACCATCCCCGACAAGCTGGGCCCCTGGAGCCCCATCGACATCCACCACC
TGAGCTGCCCCAACAATCTGGTGGTGGAGGATGAGGGCTGCACCAATCTGAGCGGCTTCAGCTA
CATGGAGCTGAAAGTGGGCTACATCCTGGCCATCAAGATGAACGGCTTCACCTGCACCGGCGTG
GTGACCGAGGCCGAGACCTACACCAACTTTGTGGGCTACGTGACCACCACCTTCAAGCGGAAGC

*FIG. 7A*

ACTTCAGACCTACCCCCGACGCCTGCAGAGCCGCCTACAACTGGAAGATGGCCGGCGACCCTAG
ATACGAGGAGAGCCTGCACAACCCCTACCCCGACTACAGATGGCTGCGGACCGTGAAAACCACC
AAGGAGTCCCTGGTGATCATCAGCCCTAGCGTGGCCGATCTGGACCCCTACGACAGAAGCCTGC
ACAGCAGAGTGTTCCCTAGCGGCAAGTGCAGCGGCGTGGCCGTGTCCAGCACCTACTGCAGCAC
CAACCACGACTACACCATCTGGATGCCCGAGAACCCTAGACTGGGCATGAGCTGCGACATCTTC
ACCAACAGCCGGGGCAAGAGAGCCAGCAAGGGCAGCGAGACCTGCGGCTTCGTGGACGAGAGAG
GCCTGTACAAGAGCCTGAAGGGCGCCTGCAAGCTGAAGCTGTGCGGCGTGCTGGGCCTGAGACT
GATGGACGGCACCTGGGTGGCCATGCAGACCAGCAACGAGACCAAGTGGTGCCCTCCTGACCAG
CTGGTGAACCTGCACGACTTCCGGAGCGATGAGATCGAGCACCTGGTGGTGGAAGAGCTGGTGC
GGAAGAGAGAGGAGTGCCTGGACGCCCTGGAGAGCATCATGACCACCAAGAGCGTGTCCTTCCG
GAGACTGAGCCACCTGAGAAAGCTGGTGCCCGGCTTTGGCAAGGCCTACACAATCTTCAACAAG
ACCCTGATGGAGGCCGATGCCCACTACAAGTCTGTGCGGACCTGGAACGAGATCCTGCCTAGCA
AGGGCTGCCTGAGAGTGGGCGGCAGATGCCACCCCCACGTGAACGGCGTGTTCTTCAACGGCAT
CATCCTGGGCCCTGACGGCAACGTGCTGATCCCTGAGATGCAGAGCAGCCTGCTGCAGCAGCAC
ATGGAACTGCTGGAGAGCAGCGTGATCCCCCTGGTGCACCCCCTGGCCGACCCCAGCACCGTGT
TCAAGGATGGCGACGAGGCCGAGGACTTCGTGGAGGTGCACCTGCCCGATGTGCACAACCAGGT
GTCCGGCGTGGACCTGGGCCTGCCCAACTGGGGCAAGTACGTGCTGCTGAGCGCCGGAGCCCTG
ACCGCCCTGATGCTGATCATCTTCCTGATGACCTGCTGCCGGAGGGTGAACAGAAGCGAGCCCA
CCCAGCACAACCTGAGAGGCACCGGCAGAGAGGTGTCCGTGACCCCCCAGAGCGGCAAGATCAT
CAGCAGCTGGGAGAGCCACAAGAGCGGCGGAGAGACCAGACTATGATTTTTTATGCCCGGGTTTT
TATAGCTAATTAGTCAAATGTGAGTTAATATTAGTATACTACATTACTAATTATTACATATTC
ATTTATATCAATCTAGTAGCATTTAGCTTTTATAAACAATATAACTGAATAGTACATACTTTA
CTAATAGTTATAAATAAGAGATACATATTTATAGTATTTTACTTTCTACACTGAATATAATAA
TATAATTATACAAATATAATTTTTAATACTATATAGTATATAACTGAAATAAAATACCAGTGTA
ATATAGTTATTATACATTATACCACATCAAAGATGAGTTATAACATCAGTGTCACTGTTAGCA
ACAGTAGTTATACGATGAGTAGTTACTCTCGTATGGCGTTAGTATGTATGTATCTTCTAGTTTT
CTTAGTAGGCATTATAGGAAACGTCAAGCTTATAAGGTTATTAATGGTATCTAGAAATATATCT
ATTATACCGTTTCTCAACTTGGGAATAGCCGATTTGCTGTTTGTGATATTCATACCTTTATACA
TTATATACATACTAAGTAATTTCCATTGGCATTTTGGTAAAGCACTTTGTAAAATTAGTTCTTT
CTTTTTACTTCTAACATGTTTGCAAGTATATTTTAATAACTGTAATAAGCGTATATAGATAT

*FIG. 7B*

GTAAAAATTACCCTTCCTGGATTTACCTATAAATATGTTAACATTAGAAATATGTACATTACTA
TATTTTTCATATGGATTATTTCTATTATACTAGGGATTCCTGCTCTTTACTTTAGAAATACTAT
CGTAACAAAAATAACGACACGCTGTGTATTAATCATTATCATGATAATAGAGAAATTGCTGAA
TTGATTTACAAAGTTATTATCTGTATCAGATTATTTTAGGATACCTACTACCTACGATAATTA
TACTCGTATGCTATACGTTACTGAT

FIG. 7C

Synthetic codon-optimized rabies virus glycoprotein G (SEQ ID NO:1)

```
  1  MVPQALLFVP  LLVFPLCFGK  FPIYTIPDKL  GPWSPIDIHH  LSCPNNLVVE
 51  DEGCTNLSGF  SYMELKVGYI  LAIKMNGFTC  TGVVTEAETY  TNFVGYVTTT
101  FKRKHFRPTP  DACRAAYNWK  MAGDPRYEES  LHNPYPDYRW  LRTVKTTKES
151  LVIISPSVAD  LDPYDRSLHS  RVFPSGKCSG  VAVSSTYCST  NHDYTIWMPE
201  NPRLGMSCDI  FTNSRGKRAS  KGSETCGFVD  ERGLYKSLKG  ACKLKLCGVL
251  GLRLMDGTWV  AMQTSNETKW  CPPDQLVNLH  DFRSDEIEHL  VVEELVRKRE
301  ECLDALESIM  TTKSVSFRRL  SHLRKLVPGF  GKAYTIFNKT  LMEADAHYKS
351  VRTWNEILPS  KGCLRVGGRC  HPHVNGVFFN  GIILGPDGNV  LIPEMQSSLL
401  QQHMELLESS  VIPLVHPLAD  PSTVFKDGDE  AEDFVEVHLP  DVHNQVSGVD
451  LGLPNWGKYV  LLSAGALTAL  MLIIFLMTCC  RRVNRSEPTQ  HNLRGTGREV
501  SVTPQSGKII  SSWESHKSGG  ETRL*
```

FIG. 8

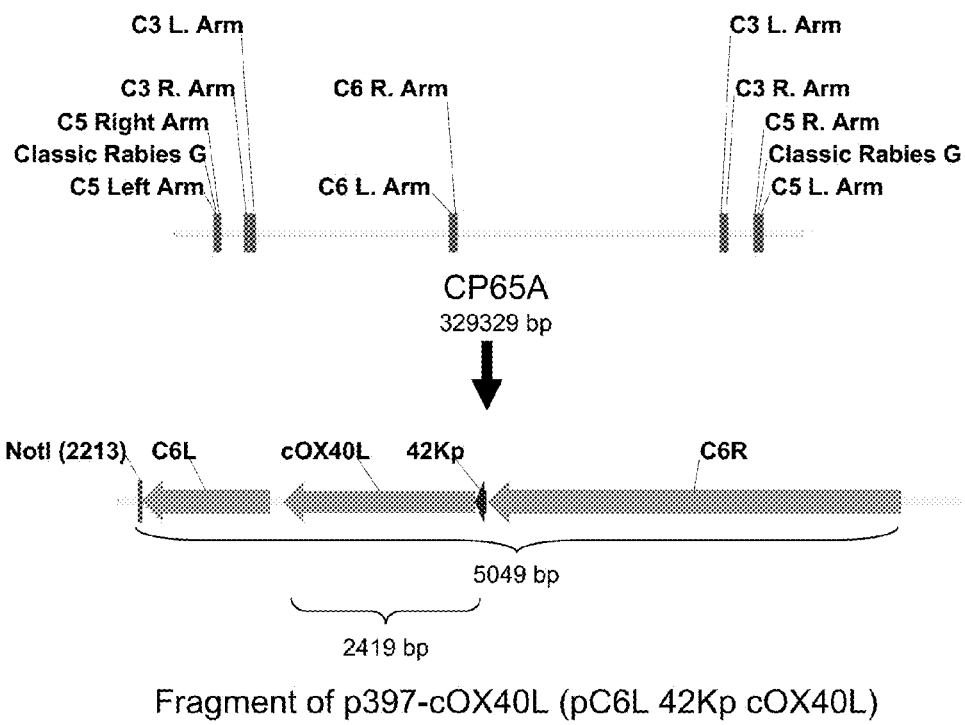
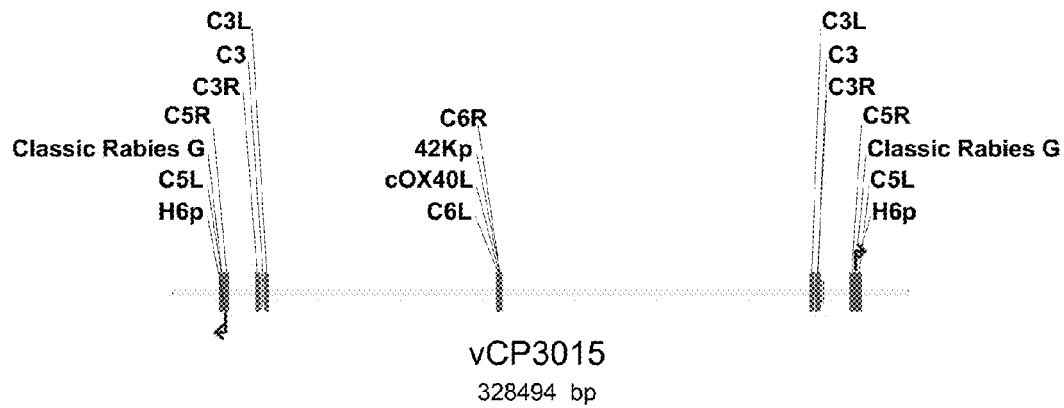
FIG. 10

Fragment of vCP3015 C6R to C6L (SEQ ID NO:7) sequence key

C6R arm (1-1148): SEQ ID NO:8

42K promoter (1155-1186): SEQ ID NO:9 cOX40L (1187-1735): SEQ ID NO:10

C6L arm (1777-2141): SEQ ID NO:11

```
   1  GTTCTAAAGT TCTTTCCTCC GAAGGTATAG AACAAAGTAT TTCTTCTACA
  51  TCCTTACTAT TTATTGCAGC TTTTAACAGC CTATCACGTA TCCTATTTTT
 101  AGTATTGGTA GAACGTTTTA GTTCTAAAGT TAAAATATTA GACATAATTG
 151  GCATATTGCT TATTCCTTGC ATAGTTGAGT CTGTAGATCG TTTCAGTATA
 201  TCACTGATTA ATGTACTACT GTTATGATGA AATATAGAAT CGATATTGGC
 251  ATTTAACTGT TTTGTTATAC TAAGTCTAGA TTTTAAATCT TCTAGTAATA
 301  TGCTATTTAA TATAAAAGCT TCCACGTTTT TGTATACATT TCTTTCCATA
 351  TTAGTAGCTA CTACTAAATG ATTATCTTCT TTCATATCTT GTAGATAAGA
 401  TAGACTATCT TTATCTTTAT TAGTAGAAAA TACTTCTGGC CATACATCGT
 451  TAAATTTTTT TGTTGTTGTT AGATATAATA TTAAATATCT AGAGGATCCT
 501  ATTATTTGTG GTAAAATGTT TATAGAGTAA AATGATCTGG CTATTAAACA
 551  TAGGCCAGTT ACCATAGAAT GCTGCTTCCC GTTACAGTGT TTTACCATAA
 601  CCATAGATCT GCCTGTATTG TTGATACATA TAACAGCTGT AAATCCTAAA
 651  AAATTCCTAT CATAATTATT AATATTAGGT AATTCATTTC CATGTGAAAG
 701  ATAGACTAAT TTTATATCCT TTACCTCCAA ATAATTATTT ACATCTCTTA
 751  AACAATCTAT TTTAATATCA TTAACTGGTA TTTTATAATA TCCAGAAAGG
 801  TTTGAAGGGG TTGATGGAAT AAGTCTATTA ACATCGTTAA GTAAATTATT
 851  AATATCATGA ATCTTTATTA TATTATACCC ATAAGTTAAA TTTATATTTA
 901  CTTTCTCATC ATCTGACTTA GTTAGTTTGT AATAAGGTGT GTCTGAAAAA
 951  ATTAAAAGGT AATTCGTTGA ATGAAGCTGT ATTTGCTGTA TCATTTTTAT
1001  CTAATTTTGG AGATTTAGCA GTACTTACTT CATTAGAAGA AGAATCTGCC
1051  AGTTCCTGTC TATTACTGAT ATTTCGTTTC ATTATTATAT GATTTATATT
```

*FIG. 15A*

```
1101  TTACTTTTTC  AATTATATAT  ACTCATTTGA  CTAGTTAATC  AATAAAAAGA
1151  ATTCTCAAAA  TTGAAAATAT  ATAATTACAA  TATAAAATGG  AAGGAGTACA
1201  ACCATTAGAT  CAAATGTTG   GAAATACACC  AGGAAGAAGA  TTTCAAAAAA
1251  ATAAAGTATT  ATTAGTAGCA  GCAATAATTC  AAGGTTTAGG  ATTATTATTA
1301  TGTTTTACAT  ATATATGTTT  ACACTTTTAT  GCATCTCAAG  TACCACCTCA
1351  ATATCCACCT  ATACAAAGTA  TAAGAGTTCA  GTTTACAAGA  TGTGAAAATG
1401  AAAAAGGTTG  TATTATTACA  TCTCCAAGTA  AAGATGAAAC  TATGAAAGTA
1451  CAAGATAATT  CAATAATCAT  AAATTGTGAT  GGTTTTACT   TAATTAGTTT
1501  AAAAGGATAT  TTTCAGAAG   AATTATCATT  ATCTTTATAT  TATAGAAAAG
1551  GTAGAGGACC  TTTATTTTCT  TTATCAAAAG  TAACATCAGT  TGATTCTATT
1601  GGAGTTGCAT  ATTTGGCTTT  TAAAGATAAA  GTATATTTTA  ATGTTACAAC
1651  TCATTCTACT  AGTTATAAAG  ATATACAAGT  AAATGGTGGT  GAATTAATAT
1701  TAATACATCA  AAATCCTGGT  GGATTTTGTG  CTTATTAATT  TTTATCCCGG
1751  GTTTTTATAG  CTAATTAGTC  ATTTTTCGTA  AGTAAGTATT  TTTATTTAAT
1801  ACTTTTTATT  GTACTTATGT  TAAATATAAC  TGATGATAAC  AAAATCCATT
1851  ATGTATTATT  TATAACTGTA  ATTTCTTTAG  CGTAGTTAGA  TGTCCAATCT
1901  CTCTCAAATA  CATCGGCTAT  CTTTTAGTG   AGATTTTGAT  CTATGCAGTT
1951  GAAACTTATG  AACGCGTGAT  GATTAAAATG  TGAACCGTCC  AAATTTGCAG
2001  TCATTATATG  AGCGTATCTA  TTATCTACTA  TCATCATCTT  TGAGTTATTA
2051  ATATCATCTA  CTTTAGAATT  GATAGGAAAT  ATGAATACCT  TGTAGTAAT
2101  ATCTATACTA  TCTACACCTA  ACTCATTAAG  ACTTTTGATA  G
```

*FIG. 15B*

Predicted amino acid sequence of synthetic cOX40L (SEQ ID NO:12)
```
  1   MEGVQPLDQN  VGNTPGRRFQ  KNKVLLVAAI  IQGLGLLLCF  TYICLHFYAS
 51   QVPPQYPPIQ  SIRVQFTRCE  NEKGCIITSP  SKDETMKVQD  NSIIINCDGF
101   YLISLKGYFS  EELSLSLYYR  KGRGPLFSLS  KVTSVDSIGV  AYLAFKDKVY
151   FNVTTHSTSY  KDIQVNGGEL  ILIHQNPGGF  CAY
```

*FIG. 16*

Fragment of vCP3015

C5 Right arm to Classic Rabies G:SEQ ID NO:13
1st BLACK Text: C5 right arm: SEQ ID NO:14
GREY Text: H6 promoter: SEQ ID NO:15
2nd BLACK Text: Classic Rabies G: SEQ ID NO:16
Underlined Text: Vector Sequence GCTATAAATATGCATTGGAAAAATAATCCATTTAAAGAAAGGATTCAAATACTACAAAACCTAAGCGATA
ATATGTTAACTAAGCTTATTCTTAACGACGCTTTAAATATACACAAATAAACATAATTTTTGTATAACCT
AACAAATAACTAAAACATAAAAATAATAAAAGGAAATGTAATATCGTAATTATTTTACTCAGGAATGGGG
TTAAATATTTATATCACGTGTATATCTATACTGTTATCGTATACTCTTTACAATTACTATTACGAATATG
CAAGAGATAATAAGATTACGTATTTAAGAGAATCTTGTCATGATAATTGGGTACGACATAGTGATAAATG
CTATTTCGCATCGTTACATAAAGTCAGTTGGAAAGATGGATTTGACAGATGTAACTTAATAGGTGCAAAA
ATGTTAAATAACAGCATTCTATCGGAAGATAGGATACCAGTTATATTATACAAAATCACTGGTTGGATA
AAACAGATTCTGCAATATTCGTAAAAGATGAAGATTACTGCGAATTTGTAAACTATGACAATAAAAAGCC
ATTTATCTCAACGACATCGTGTAATTCTTCCATGTTTTATGTATGTGTTTCAGATATTATGAGATTACTA
TAAACTTTTTGTATACTTATATTCCGTAAACTATATTAATCATGAAGAAAATGAAAAAGTATAGAAGCTG
TTCACGAGCGGTTGTTGAAAACAACAAAATTATACATTCAAGATGGCTTACATATACGTCTGTGAGGCTA
TCATGGATAATGACAATGCATCTCTAAATAGGTTTTTGGACAATGGATTCGACCCTAACACGGAATATGG
TACTCTACAATCTCCTCTTGAAATGGCTGTAATGTTCAAGAATACCGAGGCTATAAAAATCTTGATGAGG
TATGGAGCTAAACCTGTAGTTACTGAATGCACAACTTCTTGTCTGCATGATGCGGTGTTGAGAGACGACT
ACAAAATAGTGAAAGATCTGTTGAAGAATAACTATGTAAACAATGTTCTTTACAGCGGAGGCTTTACTCC
TTTGTGTTTGGCAGCTTACCTTAACAAAGTTAATTTGGTTAAACTTCTATTGGCTCATTCGGCGGATGTA
GATATTTCAAACACGGATCGGTTAACTCCTCTACATATAGCCGTATCAAATAAAAATTTAACAATGGTTA
AACTTCTATTGAACAAAGGTGCTGATACTGACTTGCTGGATAACATGGGACGTACTCCTTTAATGATCGC
TGTACAATCTGGAAATATTGAAATATGTAGCACACTACTTAAAAAAAATAAAATGTCCAGAACTGGGAAA
AATTGATCTTGCCAGCTGTAATTCATGGTAGAAAAGAAGTGCTCAGGCTACTTTTCAACAAAGGAGCAGA
TGTAAACTACATCTTTGAAAGAAATGGAAAATCATATACTGTTTTGGAATTGATTAAAGAAAGTTACTCT
GAGACACAAAGAGGTAGCTGAAGTGGTACTCTCAAAAGCTTCCCGGGTTAATTAATTAGTTATTAGACA
AGGTGAAAACGAAACTATTTGTAGCTTAATTAATTAGAGCTTCTTTATTCTATACTTAAAAAGTGAAAAT
AAATACAAAGGTTCTTGAGGGTTGTGTTAAATTGAAAGCGAGAAATAATCATAAATTATTTCATTATCGC
GATATCCGTTAAGTTTGTATCGTAATGGTTCCTCAAGCTCTCCTGTTTGTACCCCTTCTGGTTTTTCCGT

*FIG. 18A*

```
TGTGTTTTGGAAAATTCCCTATTTACACAATCCCAGACAAGCTTGGTCCCTGGAGCCCGATTGACATACA
TCACCTCAGCTGCCCAAACAATTTGGTAGTGGAGGACGAAGGATGCACCAACCTGTCAGGGTTCTCCTAC
ATGGAACTTAAAGTTGGATACATCTTAGCCATAAAAATGAACGGGTTCACTTGCACAGGCGTTGTGACGG
AGGCTGAAACCTACACTAACTTCGTTGGTTATGTCACAACCACGTTCAAAAGAAAGCATTTCCGCCCAAC
ACCAGATGCATGTAGAGCCGCGTACAACTGGAAGATGGCCGGTGACCCCAGATATGAAGAGTCTCTACAC
AATCCGTACCCTGACTACCGCTGGCTTCGAACTGTAAAAACCACCAAGGAGTCTCTCGTTATCATATCTC
CAAGTGTAGCAGATTTGGACCCATATGACAGATCCCTTCACTCGAGGGTCTTCCCTAGCGGGAAGTGCTC
AGGAGTAGCGGTGTCTTCTACCTACTGCTCCACTAACCACGATTACACCATTTGGATGCCCGAGAATCCG
AGACTAGGGATGTCTTGTGACATTTTTACCAATAGTAGAGGGAAGAGAGCATCCAAAGGGAGTGAGACTT
GCGGCTTTGTAGATGAAAGAGGCCTATATAAGTCTTTAAAAGGAGCATGCAAACTCAAGTTATGTGGAGT
TCTAGGACTTAGACTTATGGATGGAACATGGGTCGCGATGCAAACATCAAATGAAACCAAATGGTGCCCT
CCCGATCAGTTGGTGAACCTGCACGACTTTCGCTCAGACGAAATTGAGCACCTTGTTGTAGAGGAGTTGG
TCAGGAAGAGAGAGGAGTGTCTGGATGCACTAGAGTCCATCATGACAACCAAGTCAGTGAGTTTCAGACG
TCTCAGTCATTTAAGAAAACTTGTCCCTGGGTTTGGAAAAGCATATACCATATTCAACAAGACCTTGATG
GAAGCCGATGCTCACTACAAGTCAGTCAGAACTTGGAATGAGATCCTCCCTTCAAAAGGGTGTTTAAGAG
TTGGGGGAGGTGTCATCCTCATGTGAACGGGGTGTTTTTCAATGGTATAATATTAGGACCTGACGGCAA
TGTCTTAATCCCAGAGATGCAATCATCCCTCCTCCAGCAACATATGGAGTTGTTGGAATCCTCGGTTATC
CCCCTTGTGCACCCCCTGGCAGACCCGTCTACCGTTTTCAAGGACGGTGACGAGGCTGAGGATTTTGTTG
AAGTTCACCTTCCCGATGTGCACAATCAGGTCTCAGGAGTTGACTTGGGTCTCCCGAACTGGGGAAGTA
TGTATTACTGAGTGCAGGGCCCTGACTGCCTTGATGTTGATAATTTTCCTGATGACATGTTGTAGAAGA
GTCAATCGATCAGAACCTACGCAACACAATCTCAGAGGGACAGGGAGGGAGGTGTCAGTCACTCCCCAAA
GCGGGAAGATCATATCTTCATGGAATCACACAAGAGTGGGGGTGAGACCAGACTGTGA
```

FIG. 18B

Predicted amino acid sequence of classical rabies virus G (SEQ ID NO:1)

```
  1   MVPQALLFVP  LLVFPLCFGK  FPIYTIPDKL  GPWSPIDIHH  LSCPNNLVVE
 51   DEGCTNLSGF  SYMELKVGYI  LAIKMNGFTC  TGVVTEAETY  TNFVGYVTTT
101   FKRKHFRPTP  DACRAAYNWK  MAGDPRYEES  LHNFYPDYRW  LRTVKTTKES
151   LVIISPSVAD  LDPYDRSLHS  RVFPSGKCSG  VAVSSTYCST  NHDYTIWMPE
201   NPRLGMSCDI  FTNSRGKRAS  KGSETCGFVD  ERGLYKSLKG  ACKLKLCGVL
251   GLRLMDGTWV  AMQTSNETKW  CPPDQLVNLH  DFRSDEIEHL  VVEELVRKRE
301   ECLDALESIM  TTKSVSFRRL  SHLRKLVPGF  GKAYTIFNKT  LMEADAHYKS
351   VRTWNEILPS  KGCLRVGGRC  HPHVNGVFFN  GIILGPDGNV  LIPEMQSSLL
401   QQHMELLESS  VIPLVHPLAD  PSTVFKDGDE  AEDFVEVHLP  DVHNQVSGVD
451   LGLPNWGKYV  LLSAGALTAL  MLIIFLMTCC  RRVNRSEPTQ  HNLRGTGREV
501   SVTPQSGKII  SSWESHKSGG  ETRL*
```

FIG. 19

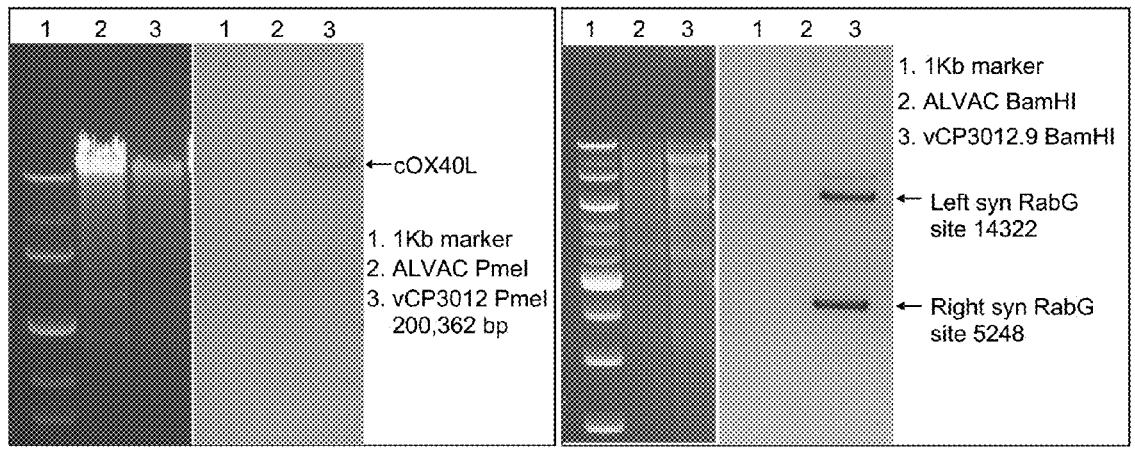
FIG. 21
FIG. 22
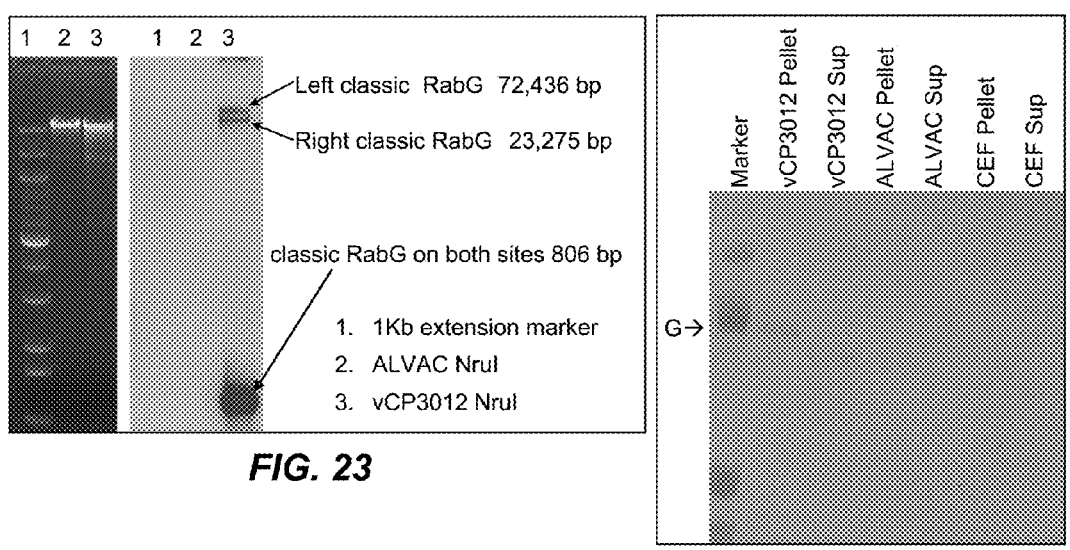
FIG. 23
FIG. 24
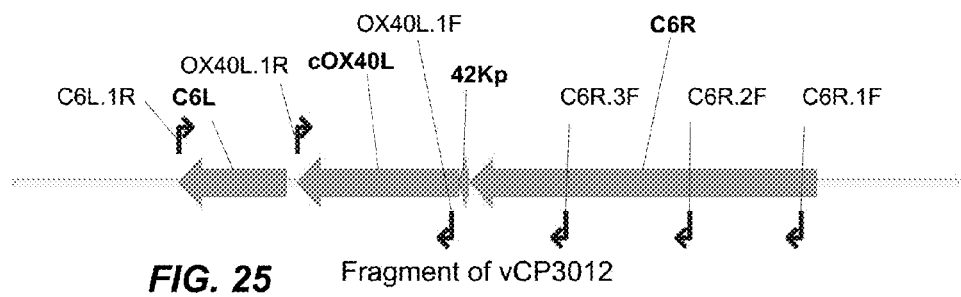
FIG. 25    Fragment of vCP3012 vCP3012 C6 Right arm to C6 Left arm: SEQ ID NO:17
1st BLACK Text: C6R arm (SEQ ID NO:18)
*1st GREY Text: 42K promoter (SEQ ID NO:9)*
2nd BLACK Text: cOX40L (SEQ ID NO:10)
*2nd GREY Text: C6L arm (SEQ ID NO:19)*
Vector = underlined text GTTCTAAAGTTCTTTCCTCCGAAGGTATAGAACAAAGTATTTCTTCTACATCCTTACTATTTATTGCAGCTTTTAAC
AGCCTATCACGTATCCTATTTTAGTATTGGTAGAACGTTTTAGTTCTAAAGTTAAAATATTAGACATAATTGGCAT
ATTGCTTATTCCTTGCATAGTTGAGTCTGTAGATCGTTTCAGTATATCACTGATTAATGTACTACTGTTATGATGAA
ATATAGAATCGATATTGGCATTTAACTGTTTTGTTATACTAAGTCTAGATTTTAAATCTTCTAGTAATATGCTATTT
AATATAAAAGCTTCCACGTTTTTGTATACATTTCTTTCCATATTAGTAGCTACTACTAAATGATTATCTTCTTTCAT
ATCTTGTAGATAAGATAGACTATCTTTATCTTTATTAGTAGAAAATACTTCTGGCCATACATCGTTAAATTTTTTG
TTGTTGTTAGATATAATATTAAATATCTAGAGGATCCTATTATTTGTGGTAAAATGTTTATAGAGTAAAATGATCTG
GCTATTAAACATAGGCCAGTTACCATAGAATGCTGCTTCCCGTTACAGTGTTTTACCATAACCATAGATCTGCCTGT
ATTGTTGATACATATAACAGCTGTAAATCCTAAAAAATTCCTATCATAATTATTAATATTAGGTAATTCATTTCCAT
GTGAAAGATAGACTAATTTTATATCCTTTACCTCCAAATAATTATTTACATCTCTTAAACAATCTATTTTAATATCA
TTAACTGGTATTTTATAATATCCAGAAAGGTTTGAAGGGGTTGATGGAATAAGTCTATTAACATCGTTAAGTAAATT
ATTAATATCATGAATCTTTATTATATTATACCCATAAGTTAAATTTATATTTACTTTCTCATCATCTGACTTAGTTA
GTTTGTAATAAGGTGTGTCTGAAAAAATTAAAAGGTAATTCGTTGAATGAAGCTGTATTTGCTGTATCATTTTTATC
TAATTTTGGAGATTTAGCAGTACTTACTTCATTAGAAGAAGAATCTGCCAGTTCCTGTCTATTACTGATATTTCGTT
TCATTATTATATGATTTATATTTTACTTTTTCAATTATATATACTCATTTGACTAGTTAATCAATAAAAA<u>GAATTC</u>*<u>*
<u>CAAATTGAAAATATATAATTACAATATAAA</u>ATGGAAGGAGTACAACCATTAGATCAAAATGTTGGAAATACACCAG
GAAGAAGATTTCAAAAAAATAAAGTATTATTAGTAGCAGCAATAATTCAAGGTTTAGGATTATTATTATGTTTTACA
TATATATGTTTACACTTTTATGCATCTCAAGTACCACCTCAATATCCACCTATACAAAGTATAAGAGTTCAGTTTAC
AAGATGTGAAAATGAAAAAGGTTGTATTATTACATCTCCAAGTAAAGATGAAACTATGAAAGTACAAGATAATTCAA
TAATCATAAATTGTGATGGTTTTTACTTAATTAGTTTAAAAGGATATTTTTCAGAAGAATTATCATTATCTTTATAT
TATAGAAAAGGTAGAGGACCTTTATTTTCTTTATCAAAAGTAACATCAGTTGATTCTATTGGAGTTGCATATTTGGC
TTTTAAAGATAAAGTATATTTTAATGTTACAACTCATTCTACTAGTTATAAAGATATACAAGTAAATGGTGGTGAAT
TAATATTAATACATCAAAATCCTGGTGGATTTTGTGCTTATTAA<u>TTTTATCCCGGGTTTTATAGCTAATTAGTCA</u>
<u>TTTTCGTAAGTAAGTATTTTATTTAATACTTTTATTGTACTTATGTTAATATAACTGATGATAACAAAATCCA</u>
<u>TTATGTATTATTATAACTGTAATTTCTTTAGCGTAGTTAGATGTCCAATCTCTCTCAAATACATCGGCTATCTTTT</u>
<u>TAGTGAGATTTTGATCTATGCAGTTGAAACTTATGAACGCGTGATGATTAAAATGTGAACCGTCCAAATTTGCAGTC</u>
<u>ATTATATGAGCGTATCTATTATCTACTATCATCATCTTTGAGTTATTAATATCATCTACTTTGAATTGATAGGAAA</u>
<u>TATGAATACCTTTGTAGTAATATCTATACTATCTACACCTAACTCATTAAGACTTTTGATAG</u>

*FIG. 26*

Fragment of vCP3012 showing synthetic rabies virus G and flanking regions (5900 bp of 329138 bp)

*FIG. 27*

Fragment of vCP3012 containing C3R arm to C3L arm (SEQ ID NO:20)

1st BLACK Text: C3R arm (SEQ ID NO:21)

*1st GREY Text: I3L promoter (SEQ ID NO:4)*

2nd BLACK Text: Synthetic Rabies G (SEQ ID NO:5)

*2nd GREY TEXT: C3R arm (SEQ ID NO:22)*

TGTAATGGGGTTTTACCTAAATCATCTTGTTCGTTTATAGGCACTCCGTGATTTATAAGTAACGCTATTATATCGTA
ACTACAATTATTTTTAAGTGCCTTTATGAGATACTGTTTATGCAAAAATAAACTTTTATCTATTTTAATACTATTAT
CTAACAATATCCTAATTAAATCTATATTCTTATACTTTATAGCGTAATGTAACGGAGTTTCAAAATTTCTAGTTTGT
ATATTAAGATCAATATTAAAATCTATAAATATTTTATACATATCATCAGATATCTTATCATACAGTACATCGTAATA
ATTTAGAAAGAATCTATTACAATTAACACCTTTTTTTAATAAATATCTAGTTAATGACTTATTGTTTCTATATACAG
AAATATATAACGGACTATTTCCAGAATGTATCTGTTCTATGTCAGCGCCAGAATCTATTAGTAGTTTAGCAATTTCT
GTATTATCTAAACTAGCAGCTTTATGAAGAGGAGGATTTTTACATTTTAAAATATCGGCACCGTGTTCTAGTAATAA
TTTTACCATTTCTATATCAGAAATACTTACGGCTAAATACAAAGACGTTGATAGTATATTTACGTTATTGTATTTGC
ATTTTTTAAGTATATACCTTACTAAATTTATATCTCTATACCTTATAGCTTTATGCAGTTCATTTATAAGTCTTCCA
TTACTCATTTCTGGTAATGAAGTATTATATATCATTATGATATTATCTCTATTTTATTCTAATAAAAACCGTTATCA
TGTTATTTATTATTTGTTATAATTATACTATTTAATAAATTATACCAAATACTTAGATACTTATTAATACCATCCTA
GAACTTGTATTTCTTGCCCCCTAAACTTGGACATGCACTCCATTAGGCGTTTCTTGTTTTCGACATCGTCCTCCTTA
ACATATCCTACTGTTATGTGAGGATTCCACGGATTATCTACTGTGATATCACCAAACACGTCCTTCGAACAGGGTAC

*FIG. 28A*

CGCATTCAGCAGAACATTTCTTAGGGCTCTAAGTTCATCAGATACCTCCAGTTTCATAACTACAGCGCATCCTTTCG
CTCCCAACTGTTTAGAGGCGTTACTCTGAGGAAAACACATCTCTTCTTTACAGACTATAGAAATAGTCTGTAAATCT
TGATCAGTTATTTGCTTTTTGAAATTTTCAAATCTATCACATTGATCCATATTTGCTATTCCAAGAGTTATATGAGG
AAAAATATCACATCCTGTCATGTATTTATTGTAACATTATTATAATCTGTAACATCAGTATCTAACCTAACGTCGT
AAAAGTTAACAGATGCCCAGTTACTATAATCCCAAGGAACCTTAACATCTAATCCCATTAAAATAGTATCCTTTCTA
CTATTTTTTTCATTGGCAAGTATGTGGCTTAGTTTACACAAAATTCCTGCCATTTTGTAACGATAGCGAAGCAATAG
CTTGTATGCTTTTTATTTGATTAACTAGTCATAAAAATCGGGATCCCTCGAGATGACATAAAGTGAAAATATATATC
ATTATATTACAAAGTACAATTATTTAGGTTTAATCATGGTGCCCCAGGCCCTGCTGTTCGTGCCCCTGCTGGTGTTC
CCCCTGTGCTTCGGCAAGTTCCCCATCTACACCATCCCCGACAAGCTGGGCCCCTGGAGCCCATCGACATCCACCA
CCTGAGCTGCCCCAACAATCTGGTGGTGGAGGATGAGGGCTGCACCAATCTGAGCGGCTTCAGCTACATGGAGCTGA
AAGTGGGCTACATCCTGGCCATCAAGATGAACGGCTTCACCTGCACCGGCGTGGTGACCGAGGCCGAGACCTACACC
AACTTTGTGGGCTACGTGACCACCACCTTCAAGCGGAAGCACTTCAGACCTACCCCCGACGCCTGCAGAGCCGCCTA
CAACTGGAAGATGGCCGGCGACCCTAGATACGAGGAGAGCCTGCACAACCCCTACCCCGACTACAGATGGCTGCGGA
CCGTGAAAACCACCAAGGAGTCCCTGGTGATCATCAGCCCTAGCGTGGCCGATCTGGACCCCTACGACAGAAGCCTG
CACAGCAGAGTGTTCCCTAGCGGCAAGTGCAGCGGCGTGGCCGTGTCCAGCACCTACTGCAGCACCAACCACGACTA
CACCATCTGGATGCCCGAGAACCCTAGACTGGGCATGAGCTGCGACATCTTCACCAACAGCCGGGGCAAGAGAGCCA
GCAAGGGCAGCGAGACCTGCGGCTTCGTGGACGAGAGAGGCCTGTACAAGAGCCTGAAGGGCGCCTGCAAGCTGAAG
CTGTGCGGCGTGCTGGGCCTGAGACTGATGGACGGCACCTGGGTGGCCATGCAGACCAGCAACGAGACCAAGTGGTG
CCCTCCTGACCAGCTGGTGAACCTGCACGACTTCCGGAGCGATGAGATCGAGCACCTGGTGGTGGAAGAGCTGGTGC
GGAAGAGAGAGGAGTGCCTGGACGCCCTGGAGAGCATCATGACCACCAAGAGCGTGTCCTTCCGGAGACTGAGCCAC
CTGAGAAAGCTGGTGCCCGGCTTTGGCAAGGCCTACACAATCTTCAACAAGACCCTGATGGAGGCCGATGCCCACTA
CAAGTCTGTGCGGACCTGGAACGAGATCCTGCCTAGCAAGGGCTGCCTGAGAGTGGGCGGCAGATGCCACCCCCACG
TGAACGGCGTGTTCTTCAACGGCATCATCCTGGGCCCTGACGGCAACGTGCTGATCCCTGAGATGCAGAGCAGCCTG
CTGCAGCAGCACATGGAACTGCTGGAGAGCAGCGTGATCCCCCTGGTGCACCCCCTGGCCGACCCCAGCACCGTGTT
CAAGGATGGCGACGAGGCCGAGGACTTCGTGGAGGTGCACCTGCCCGATGTGCACAACCAGGTGTCCGGCGTGGACC
TGGGCCTGCCCAACTGGGGCAAGTACGTGCTGCTGAGCGCCGGAGCCCTGACCGCCCTGATGCTGATCATCTTCCTG
ATGACCTGCTGCCGGAGGGTGAACAGAAGCGAGCCCACCCAGCACAACCTGAGAGGCACCGGCAGAGAGGTGTCCGT
GACCCCCCAGAGCGGCAAGATCATCAGCAGCTGGGAGAGCCACAAGAGCGGCGGAGAGACCAGACTATGATTTTTAT
GCCCGGGTTTTTATAGCTAATTAGTCAAATGTGAGTTAATATTAGTATACTACATTACTAATTATTACATATTCAT
TTATATCAATCTAGTAGCATTTAGCTTTTATAAACAATATAACTGAATAGTACATACTTTACTAATAAGTTATAAA
TAAGAATACATATTTTATAGTATTTTACTTTCTACACTGAATATAATAATATAATTATACAAATATAATTTTTAATA
CTATATAGTATATAACTGAAATAAAATACCAGTGTAATATAGTTATTATACATTTATACCACATCAAAGATGAGTTA
TAACATCAGTGTCACTGTTAGCAACAGTAGTTATACGATGAGTAGTTACTCTCGTATGCTTAGTATGTATGTATC
TTCTAGTTTTCTTAGTAGGCATTATAGGAAACGTCAAGCTTATAAGGTTATTAATGGTATCTAGAAATATATCTATT
ATACCGTTTCTCAACTTGGGAATAGCCGATTTGCTGTTTGTGATATTCATACCTTATACATTATATACATACTAAG

*FIG. 28B*

TAATTCCATTGGCATTTGTAAAGCACTTTGTAAATTAGTTCTTTCTTTTTACTTCTAACATGTTTGCAAGTA
TATTTTAATAACTGTAATAAGCGTATATAGATATGTAAAAATTACCCTTCCTGGATTTACCTATAAATATGTTAAC
ATTAGAAATATGTACATTACTATATTTTTCATATGGATTATTTCTATTATACTAGGGATTCCTGCTCTTTACTTTAG
AAATACTATCGTAACAAAAATAACGACACGCTGTGTATTAATCATTATCATGATAATAGAGAAATTGCTGAATTGA
TTTACAAAGTTATTATCTGTATCAGATTTATTTTAGGATACCTACTACCTACGATAATTATACTCGTATGCTATACG
TTACTGAT

*FIG. 28C*

Xho I (306085)
Classic G new
CP65.4F
CP65.3F
C5L.1R
C5L
C5L.2R
7634CXLF    C5R    H6p                                  7635CXLR Fragment of vCP3012 - rabies virus G and flanking regions
4191 bp (molecule 329138)

*FIG. 29*

Fragment of vCP3012 - rabies virus G and flanking regions (SEQ ID NO:23)
1st BLACK Text: C5R arm (SEQ ID NO:24)
GREY Text: H6 promoter (SEQ ID NO:15)
2nd BLACK Text: Classic Rabies G (SEQ ID NO:16)
Underlined Text: vector sequence GCTATAAATATGCATTGGAAAAATAATCCATTTAAAGAAAGGATTCAAATACTACAAAACCTAAGCGATAATATGTT
AACTAAGCTTATTCTTAACGACGCTTTAAATATACACAAATAAACATAATTTTTGTATAACCTAACAAATAACTAAA
ACATAAAAATAATAAAAGGAAATGTAATATCGTAATTATTTTACTCAGGAATGGGGTTAAATATTTATATCACGTGT
ATATCTATACTGTTATCGTATACTCTTTACAATTACTATTACGAATATGCAAGAGATAATAAGATTACGTATTTAAG
AGAATCTTGTCATGATAATTGGGTACGACATAGTGATAAATGCTATTTCGCATCGTTACATAAAGTCAGTTGGAAAG
ATGGATTTGACAGATGTAACTTAATAGGTGCAAAAATGTTAAATAACAGCATTCTATCGGAAGATAGGATACCAGTT
ATATTATACAAAAATCACTGGTTGGATAAAACAGATTCTGCAATATTCGTAAAAGATGAAGATTACTGCGAATTTGT
AAACTATGACAATAAAAAGCCATTTATCTCAACGACATCGTGTAATTCTTCCATGTTTTATGTATGTGTTTCAGATA
TTATGAGATTACTATAAACTTTTTGTATACTTATATTCCGTAAACTATATTAATCATGAAGAAAATGAAAAAGTATA
GAAGCTGTTCACGAGCGGTTGTTGAAAACAACAAAATTATACATTCAAGATGGCTTACATATACGTCTGTGAGGCTA
TCATGGATAATGACAATGCATCTCTAAATAGGTTTTTGGACAATGGATTCGACCCTAACACGGAATATGGTACTCTA
CAATCTCCTCTTGAAATGGCTGTAATGTTCAAGAATACCGAGGCTATAAAAATCTTGATGAGGTATGGAGCTAAACC
TGTAGTTACTGAATGCACAACTTCTTGTCTGCATGATGCGGTGTTGAGAGACGACTACAAAATAGTGAAAGATCTGT
TGAAGAATAACTATGTAAACAATGTTCTTTACAGCGGAGGCTTTACTCCTTTGTGTTTGGCAGCTTACCTTAACAAA
GTTAATTTGGTTAAACTTCTATTGGCTCATTCGGCGGATGTAGATATTTCAAACACGGATCGGTTAACTCCTCTACA
TATAGCCGTATCAAATAAAAATTTAACAATGGTTAAACTTCTATTGAACAAAGGTGCTGATACTGACTTGCTGGATA
ACATGGGACGTACTCCTTTAATGATCGCTGTACAATCTGGAAATATTGAAATATGTAGCACACTACTTAAAAAAAAT
AAAATGTCCAGAACTGGGAAAAATTGATCTTGCCAGCTGTAATTCATGGTAGAAAAGAAGTGCTCAGGCTACTTTTC
AACAAAGGAGCAGATGTAAACTACATCTTTGAAAGAAATGGAAAATCATATACTGTTTTGGAATTGATTAAAGAAAG
TTACTCTGAGACACAAAAGAGGTAGCTGAAGTGGTACTCTCAAAAGCTTCCCGGGTTAATTAATTAGTTATTAGACA
AGGTGAAAACGAAACTATTTGTAGCTTAATTAATTAGAGCTTCTTTATTCTATACTTAAAAAGTGAAAATAAAT
ACAAAGGTTCTTGAGGGTTGTGTTAAATTGAAAGCGAGAAATAATCATAAATTATTTCATTATCGCGATA
TCCGTTAAGTTTGTATCGTAATGGTTCCTCAAGCTCTCCTGTTTGTACCCCTTCTGGTTTTTCCGTTGTGTTTTG
GAAAATTCCCTATTTACACAATCCCAGACAAGCTTGGTCCCTGGAGCCCGATTGACATACATCACCTCAGCTGCCCA
AACAATTTGGTAGTGGAGGACGAAGGATGCACCAACCTGTCAGGGTTCTCCTACATGGAACTTAAAGTTGGATACAT
CTTAGCCATAAAAATGAACGGGTTCACTTGCACAGGCGTTGTGACGGAGGCTGAAACCTACACTAACTTCGTTGGTT
ATGTCACAACCACGTTCAAAAGAAAGCATTTCCGCCCAACACCAGATGCATGTAGAGCCGCGTACAACTGGAAGATG
GCCGGTGACCCCAGATATGAAGAGTCTCTACACAATCCGTACCCTGACTACCGCTGGCTTCGAACTGTAAAAACCAC

*FIG. 30A*

```
CAAGGAGTCTCTCGTTATCATATCTCCAAGTGTAGCAGATTTGGACCCATATGACAGATCCCTTCACTCGAGGGTCT
TCCCTAGCGGGAAGTGCTCAGGAGTAGCGGTGTCTTCTACCTACTGCTCCACTAACCACGATTACACCATTTGGATG
CCCGAGAATCCGAGACTAGGGATGTCTTGTGACATTTTTACCAATAGTAGAGGGAAGAGAGCATCCAAAGGGAGTGA
GACTTGCGGCTTTGTAGATGAAAGAGGCCTATATAAGTCTTTAAAAGGAGCATGCAAACTCAAGTTATGTGGAGTTC
TAGGACTTAGACTTATGGATGGAACATGGGTCGCGATGCAAACATCAAATGAAACCAAATGGTGCCCTCCCGATCAG
TTGGTGAACCTGCACGACTTTCGCTCAGACGAAATTGAGCACCTTGTTGTAGAGGAGTTGGTCAGGAAGAGAGAGGA
GTGTCTGGATGCACTAGAGTCCATCATGACAACCAAGTCAGTGAGTTTCAGACGTCTCAGTCATTTAAGAAAACTTG
TCCCTGGGTTTGGAAAAGCATATACCATATTCAACAAGACCTTGATGGAAGCCGATGCTCACTACAAGTCAGTCAGA
ACTTGGAATGAGATCCTCCCTTCAAAAGGGTGTTTAAGAGTTGGGGGAGGTGTCATCCTCATGTGAACGGGGTGTT
TTTCAATGGTATAATATTAGGACCTGACGGCAATGTCTTAATCCCAGAGATGCAATCATCCCTCCTCCAGCAACATA
TGGAGTTGTTGGAATCCTCGGTTATCCCCCTTGTGCACCCCCTGGCAGACCCGTCTACCGTTTTCAAGGACGGTGAC
GAGGCTGAGGATTTTGTTGAAGTTCACCTTCCCGATGTGCACAATCAGGTCTCAGGAGTTGACTTGGGTCTCCCGAA
CTGGGGAAGTATGTATTACTGAGTGCAGGGGCCCTGACTGCCTTGATGTTGATAATTTTCCTGATGACATGTTGTA
GAAGAGTCAATCGATCAGAACCTACGCAACACAATCTCAGAGGGACAGGGAGGGAGGTGTCAGTCACTCCCCAAAGC
GGGAAGATCATATCTTCATGGGAATCACACAAGAGTGGGGGTGAGACCAGACTGTGA
```

*FIG. 30B*

Non-primer sequences disclosed in this application

| SEQ ID NO | DNA/ PRT | Sequence Description |
|---|---|---|
| 1 | PRT | Predicted Rabies G AA sequence (for both wild type and synthetic codon-optimized) |
| 2 | DNA | Subsequence of recombinant vCP3006 covering the flanking C3 arms, the I3L promoter as well as the synthetic rabies G |
| 3 | DNA | vCP3006 C3L arm |
| 4 | DNA | vCP3006 I3L promoter |
| 5 | DNA | vCP3006 synthetic rabies G |
| 6 | DNA | vCP3006 C3R arm |
| 7 | DNA | Fragment of vCP3015 containing C6R arm to C6L arm |
| 8 | DNA | vCP3015 C6R arm |
| 9 | DNA | vCP3015 42K promoter |
| 10 | DNA | vCP3015 cOX40L |
| 11 | DNA | vCP3015 C6L arm |
| 12 | PRT | cOX40L predicted AA sequence |
| 13 | DNA | Fragment of vCP3015 containing C5R arm to Classic Rabies G |
| 14 | DNA | vCP3015 C5R arm |
| 15 | DNA | vCP3015 H6 promoter |
| 16 | DNA | Classic rabies G gene (wild type) |
| 17 | DNA | vCP3012 C6R arm to C6L arm |
| 18 | DNA | vCP3012 C6R arm |
| 19 | DNA | vCP3012 C6L arm |
| 20 | DNA | vCP3012 C3R arm to C3L arm |
| 21 | DNA | vCP3012 C3R arm |
| 22 | DNA | vCP3012 C3L arm |
| 23 | DNA | Fragment of vCP3012 - rabies virus G and flanking regions |
| 24 | DNA | vCP3012 C5R arm |
| 63 | PRT | Felis catus OX40L |
| 64 | PRT | Equus caballus OX40L |
| 65 | PRT | Bos taurus OX40L |
| 66 | PRT | Sus scrofa OX40L |
| 67 | PRT | Pan troglodytes OX40L |
| 68 | DNA | Plasmid p397-cOX40L (pC6 42Kp cOX40L) |
| 69 | DNA | Plasmid p397-Syn Rabies G (pC3 I3Lp Syn Rabies G) |
| 70 | PRT | Gallus gallus OX40L |
| 71 | PRT | Ovis aries OX40L |

*FIG. 36*

| Primer name | Sequences ( 5' → 3') | Gene | SEQ ID |
|---|---|---|---|
| C5R.1R primer | CTCTTGCATATTCGTAATAGTAATTG | Classic G/C5 | 25 |
| C5R.1F primer | ATTCTATCGGAAGATAGGATACCAG | | 26 |
| C5R.2R primer | TCAACAACCGCTCGTGAACAGCTTC | | 27 |
| C5R.2F primer | ATGCACAACTTCTTGTCTGCATGATG | | 28 |
| C5R.3R primer | TACGGCTATATGTAGAGGAGTTAACC | | 29 |
| C5R.3F primer | CTCTGAGACACAAAAGAGGTAGCTG | | 30 |
| C5L.1F primer | CATCATGAGCAACGCGTTAGTATAT | | 31 |
| C5L.1R primer | TTAGAAATTATGCATTTTAGA | | 32 |
| C5L.2R primer | GGAGATACCTTTAGATATGGATCTG | | 33 |
| C5L.3R primer | TTGTAACCATAGTATATCTTAGCGC | | 34 |
| 7634CXL-F primer | GTTCTCGTAGGAGAGAACTATTGAC | | 35 |
| 7635CXL-R primer | CGTCTTCAGCTGTAAACAAATATAATG | | 36 |
| CP65.1F primer | ATGGTTCCTCAGGCTCTCCTGTTTG | | 37 |
| CP65.1R primer | TCACAGTCTGGTCTCACCCCCACTC | | 38 |
| CP65.2R primer | GACCCATGTTCCATCCATAA | | 39 |
| CP65.3F primer | GTCTCACCCCCACTCTTGTGTG | | 40 |
| CP65.4F primer | GAAAACGGTAGACGGGTCTG | | 41 |
| C3R.1F primer | CATAGCTTTATGTAAAGGAGTAT | Synthetic G/C3 | 42 |
| C3R.2F primer | TGTAATGGGGTTTTACCTAA | | 43 |
| C3R.3F primer | GCTTTATGAAGAGGAGGATTTT | | 44 |
| C3R.4F primer | GCATTCAGCAGAACATTTCT | | 45 |
| C3L.1F primer | TAGTTACTCTCGTATGGCGT | | 46 |
| C3L.1R primer | ATCAGTAACGTATAGCATACG | | 47 |
| C3L.2R primer | TACATATTTCTAATGTTAACATATT | | 48 |
| I3L.1F primer | GGATCCCTCGAGATGAGATA | | 49 |
| RabG.PF primer | ATAGCTTGTATGCTTTTTATTTGAT | | 50 |
| RabG.PR primer | GAACAGCAGGGCCTGGGGCACCATG | | 51 |
| RabG.1F primer | GTGAAAACCACCAAGGAGTC | | 52 |
| RabG.1R primer | TTCTGTTCACCCTCCGGCAG | | 53 |
| RabG.2R primer | TGGTGAAGATGTCGCAGCTCATGCC | | 54 |
| RabG.2F primer | ACCACCAAGAGCGTGTCCTT | | 55 |
| RabG.3F primer | TTCCTGATGACCTGCTGCCGGA | | 56 |
| C6R.1F primer | GTTCTAAAGTTCTTTCCTCC | cOX40L/C6 | 57 |
| C6R.2F primer | TCTTTCATATCTTGTAGATAAGA | | 58 |
| C6R.3F primer | TGAAGGGGTTGATGGAATAA | | 59 |
| C6L.1R primer | CTATCAAAAGTCTTAATGAGTTAGG | | 60 |
| OX40L.1F primer | ATGGAAGGAGTACAACCATTAGATC | | 61 |
| OX40L.1R primer | TTAATAAGCACAAAATCCACCAGGA | | 62 |

*FIG. 37*

SEQ NO:12 (dog); SEQ NO:63 (cat); SEQ NO:64 (horse); SEQ ID NO:65 (cow)
SEQ NO:66 (pig); SEQ NO:67 (chimp); SEQ NO:71 (sheep)
SEQ NO:70 (chicken; first 50 AA not shown for this alignment)

```
                  51                                              100
SEQ ID: 12   (1)  -MEGVQPLDQNVGNTPGRRFQK KVL  AAII GLG  L FT ICLHFYA
SEQ ID: 63   (1)  -MEGVQPLDENVGNAPGRRFQS KLL  TAVI QLC  L FT ICLHFYA
SEQ ID: 67   (1)  -MERVQPLEENVGNAARPRFER KLL  ASVI QGLG L FT ICLHFSA
SEQ ID: 64   (1)  -MEGVQPLEENVGNTPGRRFQR KLL  TSII QGLG L LT VCLHFYT
SEQ ID: 65   (1)  -MEGVQPLDENVGNVPGRRFLR KLL  ASII GLG  L LT ICLHFYA
SEQ ID: 71   (1)  -MEGVQPLDENVGNAPGRRFLR KLL  ASII GLG  L LT ICLHFYA
SEQ ID: 66   (1)  -MEGVQPLDENVGNAPGRRLLR KLL  ASVI QCLG L LT ICLHLYA
SEQ ID: 70  (51)  KEPAGMRSDDEWRGWQKGQAKR TLY  SAAT WIL  A LI LGTDSLQ
                  101                                             150
SEQ ID: 12  (50)  SQVPPQYPPIQSIRVQF RCENEK CIITSPSKDETMK QDN II N
SEQ ID: 63  (50)  SQVPPQYPPIQSIKVQF KCGNGT CIITSPNKDETMK QDN II N
SEQ ID: 67  (50)  LQVSHRYPRIQSIKVQF EYKKEK FILTSQKEDEVMK QNN VI N
SEQ ID: 64  (50)  SQVPSQYPPIQSIRVQF SCENEK FIITSPNQDEIMK QDN II N
SEQ ID: 65  (50)  -QVPSQYPPIQSIRVQF KCENEN FIITSPDADGTMK QNN II T
SEQ ID: 71  (50)  -QVPSQYPPIQSIRVRF -CENEN FIITSPDADGTMK QNN II T
SEQ ID: 66  (50)  -QVPSQYPPIQSIKVQF KCENDN FIITPSSKDGTMK QNN II N
SEQ ID: 70 (101)  -LWTPHSDKVKWTYIRY GQ-SIA VAMNLSAEFTSIP ING IM P
                  151                                             200
SEQ ID: 12 (100)  F LI   YF EELSLSLYR-------  GRG  FSLSKVTSVDSIGVAY
SEQ ID: 63 (100)  F LI   YF EELSLSLYYR-------  GRK  FSLSKVKSVDSIGVAH
SEQ ID: 67 (100)  F LI   YF QEVNISLHYQ-------  DEE  FQLKKVRSVNSLMVAS
SEQ ID: 64 (100)  F LI   YF QELSLSLHYR-------  GRE  SSLSKVRSVNSIMVAY
SEQ ID: 65  (99)  F LI   YF QELSLRLLYR-------  GRE  FSLNMVKIVDSVTVAY
SEQ ID: 71  (98)  F LI   YF QKLSLRLLYR-------  GRE  FSLNMVKIVDSVTVAY
SEQ ID: 66  (99)  F LI   YF QELSLMLQYR-------  GRK  FSLNKVKSVDSVTVAD
SEQ ID: 70 (149)  L VV   VL PDLEKSSLKLMMKNTES NAA  WERDVQNSSNAVDLIT
                  201                                   241
SEQ ID: 12 (143)  LAFKDKVYF VTTHST YKDIQVNGGE ILIHQNPGG  AY
SEQ ID: 63 (143)  LAFKDKVYF VTTHNT YKDIQVNGGE IVILQNPGG  VL
SEQ ID: 67 (143)  LTYKDKVYL VTTDNT LDDFHVNGGE ILIHQNPGE  VL
SEQ ID: 64 (143)  LAFKDKVYL VTTHNT CDDIQVNGGE ILIHQNPGG  AY
SEQ ID: 65 (142)  LRFKDKVYL MTTQNA CEDIQVNGGE ILIHQNPGG  VY
SEQ ID: 71 (141)  LRFKDKVYL VTTQNA CEDIQVNGGE ILIHQNPGG  VY
SEQ ID: 66 (142)  LAFKDKVFL VTTHSA CEDIQVNGGE ILIHQNPGG  VY
SEQ ID: 70 (199)  MLYLF-AQN IILSTS NATIQCLTFS VLLNP---V  NP
```

|        | SEQ 12 | SEQ 63 | SEQ 67 | SEQ 64 | SEQ 65 | SEQ 71 | SEQ 66 | SEQ 70 |
|--------|--------|--------|--------|--------|--------|--------|--------|--------|
| SEQ 12 |        | 89     | 68     | 86     | 81     | 81     | 81     | 22     |
| SEQ 63 |        |        | 69     | 82     | 79     | 79     | 82     | 22     |
| SEQ 67 |        |        |        | 73     | 69     | 70     | 69     | 22     |
| SEQ 64 |        |        |        |        | 84     | 83     | 81     | 23     |
| SEQ 65 |        |        |        |        |        | 98     | 88     | 24     |
| SEQ 71 |        |        |        |        |        |        | 88     | 24     |
| SEQ 66 |        |        |        |        |        |        |        | 24     |
| SEQ 70 |        |        |        |        |        |        |        |        |

*FIG. 38*

SEQUENCE LISTING

```
<160> NUMBER OF SEQ ID NOS: 71

<210> SEQ ID NO 1
<211> LENGTH: 524
```

-continued

```
<212> TYPE: PRT
<213> ORGANISM: Rabies virus

<400> SEQUENCE: 1

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr Arg Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400
```

```
Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520

<210> SEQ ID NO 2
<211> LENGTH: 3609
<212> TYPE: DNA
<213> ORGANISM: Artificial Sequence
<220> FEATURE:
<223> OTHER INFORMATION: Subsequence of recombinant vCP3006 covering the
      flanking C3 arms, the I3L promoter as well as the synthetic rabies
      G

<400> SEQUENCE: 2
gctttatgaa gaggaggatt tttacatttt aaaatatcgg caccgtgttc tagtaataat     60
tttaccattt ctatatcaga aatacttacg gctaaataca aagacgttga tagtatattt    120
acgttattgt atttgcattt tttaagtata taccttacta aatttatatc tctatacctt    180
atagctttat gcagttcatt tataagtctt ccattactca tttctggtaa tgaagtatta    240
tatatcatta tgatattatc tctattttat tctaataaaa accgttatca tgttatttat    300
tatttgttat aattatacta tttaataaat tataccaaat acttagatac ttattaatac    360
catcctagaa cttgtatttc ttgcccccta aacttggaca tgcactccat taggcgtttc    420
ttgttttcga catcgtcctc cttaacatat cctactgtta tgtgaggatt ccacggatta    480
tctactgtga tatcaccaaa cacgtccttc gaacagggta ccgcattcag cagaacattt    540
cttagggctc taagttcatc agatacctcc agtttcataa ctacagcgca tcctttcgct    600
cccaactgtt tagaggcgtt actctgagga aaacacatct cttctttaca gactatagaa    660
atagtctgta aatcttgatc agttatttgc tttttgaaat tttcaaatct atcacattga    720
tccatatttg ctattccaag agttatatga ggaaaaatat cacatcctgt catgtatttt    780
attgtaacat tattataatc tgtaacatca gtatctaacc taacgtcgta aaagttaaca    840
gatgcccagt tactataatc ccaaggaacc ttaacatcta atcccattaa aatagtatcc    900
tttctactat ttttttcatt ggcaagtatg tggcttagtt tacacaaaat tcctgccatt    960
ttgtaacgat agcgaagcaa tagcttgtat gctttttatt tgattaacta gtcataaaaa   1020
tcgggatccc tcgagatgag ataaagtgaa aatatatatc attatattac aaagtacaat   1080
tatttaggtt taatcatggt gccccaggcc ctgctgttcg tgcccctgct ggtgttcccc   1140
ctgtgcttcg gcaagttccc catctacacc atccccgaca agctgggccc ctggagcccc   1200
atcgacatcc accacctgag ctgccccaac aatctggtgg tggaggatga gggctgcacc   1260
```

```
aatctgagcg gcttcagcta catggagctg aaagtgggct acatcctggc catcaagatg    1320
aacggcttca cctgcaccgg cgtggtgacc gaggccgaga cctacaccaa ctttgtgggc    1380
tacgtgacca ccaccttcaa gcggaagcac ttcagaccta cccccgacgc ctgcagagcc    1440
gcctacaact ggaagatggc cggcgaccct agatacgagg agagcctgca caacccctac    1500
cccgactaca gatggctgcg gaccgtgaaa accaccaagg agtccctggt gatcatcagc    1560
cctagcgtgg ccgatctgga cccctacgac agaagcctgc acagcagagt gttccctagc    1620
ggcaagtgca gcggcgtggc cgtgtccagc acctactgca gcaccaacca cgactacacc    1680
atctggatgc ccgagaaccc tagactgggc atgagctgcg acatcttcac caacagccgg    1740
ggcaagagag ccagcaaggg cagcgagacc tgcggcttcg tggacgagag aggcctgtac    1800
aagagcctga gggcgcctg caagctgaag ctgtgcggcg tgctgggcct gagactgatg    1860
gacggcacct gggtggccat gcagaccagc aacgagacca gtggtgccc tcctgaccag    1920
ctggtgaacc tgcacgactt ccggagcgat gagatcgagc acctggtggt ggaagagctg    1980
gtgcggaaga gagaggagtg cctggacgcc ctggagagca tcatgaccac caagagcgtg    2040
tccttccgga gactgagcca cctgagaaag ctggtgcccg ctttggcaa ggcctacaca    2100
atcttcaaca agaccctgat ggaggccgat gcccactaca gtctgtgcg gacctggaac    2160
gagatcctgc ctagcaaggg ctgcctgaga gtgggcggca gatgccaccc ccacgtgaac    2220
ggcgtgttct tcaacggcat catcctgggc cctgacggca cgtgctgat ccctgagatg    2280
cagagcagcc tgctgcagca gcacatggaa ctgctggaga gcagcgtgat ccccctggtg    2340
cacccccctgg ccgaccccag caccgtgttc aaggatggcg acgaggccga ggacttcgtg    2400
gaggtgcacc tgcccgatgt gcacaaccag gtgtccggcg tggacctggg cctgcccaac    2460
tggggcaagt acgtgctgct gagcgccgga gccctgaccg ccctgatgct gatcatcttc    2520
ctgatgacct gctgccggag ggtgaacaga agcgagccca cccagcacaa cctgagaggc    2580
accggcagag aggtgtccgt gacccccag agcggcaaga tcatcagcag ctgggagagc    2640
cacaagagcg gcggagagac cagactatga tttttatgcc cgggttttta tagctaatta    2700
gtcaaatgtg agttaatatt agtatactac attactaatt tattacatat tcatttatat    2760
caatctagta gcatttagct tttataaaac aatataactg aatagtacat actttactaa    2820
taagttataa ataagagata catatttata gtatttact ttctacactg aatataataa    2880
tataattata caaatataat tttaatact atatagtata taactgaaat aaaataccag    2940
tgtaatatag ttattataca tttataccac atcaaagatg agttataaca tcagtgtcac    3000
tgttagcaac agtagttata cgatgagtag ttactctcgt atggcgttag tatgtatgta    3060
tcttctagtt ttcttagtag gcattatagg aaacgtcaag cttataaggt tattaatggt    3120
atctagaaat atatctatta taccgtttct caacttggga atagccgatt tgctgtttgt    3180
gatattcata cctttataca ttatatacat actaagtaat ttccattggc attttggtaa    3240
agcactttgt aaaattagtt ctttctttt tacttctaac atgtttgcaa gtatattttt    3300
aataactgta ataagcgtat atagatatgt aaaaattacc cttcctggat ttacctataa    3360
atatgttaac attagaaata tgtacattac tatattttc atatggatta tttctattat    3420
actagggatt cctgctcttt actttagaaa tactatcgta acaaaaaata acgacacgct    3480
gtgtattaat cattatcatg ataatagaga aattgctgaa ttgatttaca aagttattat    3540
ctgtatcaga tttattttag gatacctact acctacgata attatactcg tatgctatac    3600
gttactgat                                                            3609
```

<210> SEQ ID NO 3
<211> LENGTH: 991
<212> TYPE: DNA
<213> ORGANISM: Artificial Sequence
<220> FEATURE:
<223> OTHER INFORMATION: vCP3006 C3 Right arm

<400> SEQUENCE: 3
gctttatgaa gaggaggatt tttacatttt aaaatatcgg caccgtgttc tagtaataat 60
tttaccattt ctatatcaga aatacttacg gctaaataca aagacgttga tagtatattt 120
acgttattgt atttgcattt tttaagtata taccttacta aatttatatc tctatacctt 180
atagctttat gcagttcatt tataagtctt ccattactca tttctggtaa tgaagtatta 240
tatatcatta tgatattatc tctattttat tctaataaaa accgttatca tgttatttat 300
tatttgttat aattatacta tttaataaat tataccaaat acttagatac ttattaatac 360
catcctagaa cttgtatttc ttgcccccta aacttggaca tgcactccat taggcgtttc 420
ttgttttcga catcgtcctc cttaacatat cctactgtta tgtgaggatt ccacggatta 480
tctactgtga tatcaccaaa cacgtccttc gaacagggta ccgcattcag cagaacattt 540
cttagggctc taagttcatc agatacctcc agtttcataa ctacagcgca tcctttcgct 600
cccaactgtt tagaggcgtt actctgagga aaacacatct cttctttaca gactatagaa 660
atagtctgta aatcttgatc agttatttgc tttttgaaat tttcaaatct atcacattga 720
tccatatttg ctattccaag agttatatga ggaaaaatat cacatcctgt catgtatttt 780
attgtaacat tattataatc tgtaacatca gtatctaacc taacgtcgta aaagttaaca 840
gatgcccagt tactataatc ccaaggaacc ttaacatcta atcccattaa aatagtatcc 900
tttctactat ttttttcatt ggcaagtatg tggcttagtt tacacaaaat tcctgccatt 960
ttgtaacgat agcgaagcaa tagcttgtat g 991

<210> SEQ ID NO 4
<211> LENGTH: 60
<212> TYPE: DNA
<213> ORGANISM: Artificial Sequence
<220> FEATURE:
<223> OTHER INFORMATION: I3L promoter

<400> SEQUENCE: 4
atgagataaa gtgaaaatat atatcattat attacaaagt acaattattt aggtttaatc 60

<210> SEQ ID NO 5
<211> LENGTH: 2667
<212> TYPE: DNA
<213> ORGANISM: Artificial Sequence
<220> FEATURE:
<223> OTHER INFORMATION: Synthetic codon-optimized rabies G gene

<400> SEQUENCE: 5
gctttatgaa gaggaggatt tttacatttt aaaatatcgg caccgtgttc tagtaataat 60
tttaccattt ctatatcaga aatacttacg gctaaataca aagacgttga tagtatattt 120
acgttattgt atttgcattt tttaagtata taccttacta aatttatatc tctatacctt 180
atagctttat gcagttcatt tataagtctt ccattactca tttctggtaa tgaagtatta 240
tatatcatta tgatattatc tctattttat tctaataaaa accgttatca tgttatttat 300
tatttgttat aattatacta tttaataaat tataccaaat acttagatac ttattaatac 360

```
catcctagaa cttgtatttc ttgcccccta aacttggaca tgcactccat taggcgtttc      420
ttgttttcga catcgtcctc cttaacatat cctactgtta tgtgaggatt ccacggatta      480
tctactgtga tatcaccaaa cacgtccttc gaacagggta ccgcattcag cagaacattt      540
cttagggctc taagttcatc agatacctcc agtttcataa ctacagcgca tcctttcgct      600
cccaactgtt tagaggcgtt actctgagga aaacacatct cttctttaca gactatagaa      660
atagtctgta aatcttgatc agttatttgc tttttgaaat tttcaaatct atcacattga      720
tccatatttg ctattccaag agttatatga ggaaaaatat cacatcctgt catgtatttt      780
attgtaacat tattataatc tgtaacatca gtatctaacc taacgtcgta aaagttaaca      840
gatgcccagt tactataatc ccaaggaacc ttaacatcta atcccattaa aatagtatcc      900
tttctactat ttttttcatt ggcaagtatg tggcttagtt tacacaaaat tcctgccatt      960
ttgtaacgat agcgaagcaa tagcttgtat gcttttatt tgattaacta gtcataaaaa      1020
tcgggatccc tcgagatgag ataaagtgaa aatatatatc attatattac aaagtacaat      1080
tatttaggtt taatcatggt gccccaggcc ctgctgttcg tgccctgct ggtgttcccc        1140 ctgtgcttcg gcaagttccc catctacacc atccccgaca agctgggccc ctggagcccc      1200
atcgacatcc accacctgag ctgccccaac aatctggtgg tggaggatga gggctgcacc      1260
aatctgagcg gcttcagcta catggagctg aaagtgggct acatcctggc catcaagatg      1320
aacggcttca cctgcaccgg cgtggtgacc gaggccgaga cctacaccaa ctttgtgggc      1380
tacgtgacca ccaccttcaa gcggaagcac ttcagaccta ccccgacgc ctgcagagcc       1440 gcctacaact ggaagatggc cggcgaccct agatacgagg agagcctgca caccccctac     1500
cccgactaca gatggctgcg gaccgtgaaa accaccaagg agtccctggt gatcatcagc      1560
cctagcgtgg ccgatctgga cccctacgac agaagcctgc acagcagagt gttccctagc     1620
ggcaagtgca gcggcgtggc cgtgtccagc acctactgca gcaccaacca cgactacacc      1680
atctggatgc ccgagaaccc tagactgggc atgagctgcg acatcttcac caacagccgg      1740
ggcaagagag ccagcaaggg cagcgagacc tgcggcttcg tggacgagag aggcctgtac     1800
aagagcctga gggcgcctg caagctgaag ctgtgcggcg tgctgggcct gagactgatg       1860
gacggcacct gggtggccat gcagaccagc aacgagacca agtggtgccc tcctgaccag     1920
ctggtgaacc tgcacgactt ccggagcgat gagatcgagc acctggtggt ggaagagctg      1980
gtgcggaaga gagaggagtg cctggacgcc ctggagagca tcatgaccac caagagcgtg      2040
tccttccgga gactgagcca cctgagaaag ctggtgcccg ctttggcaa ggcctacaca       2100 atcttcaaca agaccctgat ggaggccgat gcccactaca gtctgtgcg gacctggaac      2160 gagatcctgc ctagcaaggg ctgcctgaga gtgggcggca gatgccaccc ccacgtgaac      2220
ggcgtgttct tcaacggcat catcctgggc cctgacggca acgtgctgat ccctgagatg     2280
cagagcagcc tgctgcagca gcacatggaa ctgctggaga gcagcgtgat ccccctggtg     2340 cacccctgg ccgaccccag caccgtgttc aaggatggcg acgaggccga ggacttcgtg       2400
gaggtgcacc tgcccgatgt gcacaaccag gtgtccggcg tggacctggg cctgcccaac    2460
tggggcaagt acgtgctgct gagcgccgga gccctgaccg ccctgatgct gatcatcttc     2520
ctgatgacct gctgccggag ggtgaacaga agcgagccca cccagcacaa cctgagaggc     2580
accggcagag aggtgtccgt gaccccccag agcggcaaga tcatcagcag ctgggagagc     2640
cacaagagcg gcggagagac cagacta                                         2667
```

<210> SEQ ID NO 6
<211> LENGTH: 939
<212> TYPE: DNA
<213> ORGANISM: Artificial Sequence
<220> FEATURE:
<223> OTHER INFORMATION: vCP3006 C3 right arm

<400> SEQUENCE: 6

```
tttttatgcc cgggttttta tagctaatta gtcaaatgtg agttaatatt agtatactac      60
attactaatt tattacatat tcatttatat caatctagta gcatttagct tttataaaac    120
aatataactg aatagtacat actttactaa taagttataa ataagagata catatttata    180
gtattttact ttctcactg aatataataa tataattata caaatataat ttttaatact     240
atatagtata taactgaaat aaaataccag tgtaatatag ttattataca tttataccac    300
atcaaagatg agttataaca tcagtgtcac tgttagcaac agtagttata cgatgagtag    360
ttactctcgt atggcgttag tatgtatgta tcttctagtt ttcttagtag gcattatagg    420
aaacgtcaag cttataaggt tattaatggt atctagaaat atatctatta taccgtttct    480
caacttggga atagccgatt tgctgtttgt gatattcata cctttataca ttatatacat    540
actaagtaat ttccattggc attttggtaa agcactttgt aaaattagtt ctttctttt    600
tacttctaac atgtttgcaa gtatattttt aataactgta ataagcgtat atagatatgt    660
aaaaattacc cttcctggat ttacctataa atatgttaac attagaaata tgtacattac    720
tatattttc atatggatta tttctattat actagggatt cctgctcttt actttagaaa     780
tactatcgta acaaaaaata acgacacgct gtgtattaat cattatcatg ataatagaga    840
aattgctgaa ttgatttaca aagttattat ctgtatcaga tttattttag gatacctact    900
acctacgata attatactcg tatgctatac gttactgat                           939
```

<210> SEQ ID NO 7
<211> LENGTH: 2141
<212> TYPE: DNA
<213> ORGANISM: Artificial Sequence
<220> FEATURE:
<223> OTHER INFORMATION: Fragment of vCP3015 C6R to C6L

<400> SEQUENCE: 7

```
gttctaaagt tctttcctcc gaaggtatag aacaaagtat ttcttctaca tccttactat     60
ttattgcagc ttttaacagc ctatcacgta tcctattttt agtattggta gaacgtttta    120
gttctaaagt taaaatatta gacataattg gcatattgct tattccttgc atagttgagt    180
ctgtagatcg tttcagtata tcactgatta atgtactact gttatgatga aatatagaat    240
cgatattggc atttaactgt tttgttatac taagtctaga ttttaaatct tctagtaata    300
tgctatttaa tataaaagct tccacgtttt tgtatacatt tctttccata ttagtagcta    360
ctactaaatg attatcttct ttcatatctt gtagataaga tagactatct ttatctttat    420
tagtagaaaa tacttctggc catacatcgt taaatttttt tgttgttgtt agatataata    480
ttaaatatct agaggatcct attatttgtg gtaaaatgtt tatagagtaa aatgatctgg    540
ctattaaaca taggccagtt accatagaat gctgcttccc gttacagtgt tttaccataa    600
ccatagatct gcctgtattg ttgatacata taacagctgt aaatcctaaa aaattcctat    660
cataattatt aatattaggt aattcatttc catgtgaaag atagactaat tttatatcct    720
ttacctccaa ataattattt acatctctta aacaatctat tttaatatca ttaactggta    780
ttttataata tccagaaagg tttgaagggg ttgatggaat aagtctatta acatcgttaa    840
```

```
gtaaattatt aatatcatga atctttatta tattataccc ataagttaaa tttatattta        900
ctttctcatc atctgactta gttagtttgt aataaggtgt gtctgaaaaa attaaaaggt        960
aattcgttga atgaagctgt atttgctgta tcatttttat ctaattttgg agatttagca       1020
gtacttactt cattagaaga agaatctgcc agttcctgtc tattactgat atttcgtttc       1080
attattatat gatttatatt ttacttttc  aattatatat actcatttga ctagttaatc       1140
aataaaaaga attctcaaaa ttgaaaatat aaattacaa  ataaaatgg  aaggagtaca       1200 accattagat caaaatgttg gaaatacacc aggaagaaga tttcaaaaaa ataaagtatt       1260
attagtagca gcaataattc aaggtttagg attattatta tgttttacat atatatgttt       1320 acactttat  gcatctcaag taccacctca atatccacct atacaaagta taagagttca       1380
gtttacaaga tgtgaaaatg aaaaaggttg tattattaca tctccaagta aagatgaaac       1440
tatgaaagta caagataatt caataatcat aaattgtgat ggtttttact taattagttt       1500
aaaaggatat ttttcagaag aattatcatt atctttatat tatagaaaag gtagaggacc       1560
tttattttct ttatcaaaag taacatcagt tgattctatt ggagttgcat atttggcttt       1620
taaagataaa gtatatttta atgttacaac tcattctact agttataaag atatacaagt       1680
aaatggtggt gaattaatat taatacatca aaatcctggt ggattttgtg cttattaatt       1740
tttatcccgg gttttatag  ctaattagtc atttttcgta agtaagtatt tttatttaat       1800 acttttatt  gtacttatgt taaatataac tgatgataac aaaatccatt atgtattatt       1860
tataactgta atttctttag cgtagttaga tgtccaatct ctctcaaata catcggctat       1920 cttttagtg  agattttgat ctatgcagtt gaaacttatg aacgcgtgat gattaaaatg       1980
tgaaccgtcc aaatttgcag tcattatatg agcgtatcta ttatctacta tcatcatctt       2040
tgagttatta atatcatcta ctttagaatt gataggaaat atgaatacct ttgtagtaat       2100
atctatacta tctacaccta actcattaag acttttgata g                          2141
```

<210> SEQ ID NO 8
<211> LENGTH: 1148
<212> TYPE: DNA
<213> ORGANISM: Artificial Sequence
<220> FEATURE:
<223> OTHER INFORMATION: vCP3015 C6R

<400> SEQUENCE: 8

```
gttctaaagt tctttcctcc gaaggtatag aacaaagtat ttcttctaca tccttactat         60
ttattgcagc tttaacagc  ctatcacgta tcctatttt  agtattggta gaacgtttta        120
gttctaaagt taaatatta  gacataattg gcatattgct tattccttgc atagttgagt        180
ctgtagatcg tttcagtata tcactgatta atgtactact gttatgatga aatatagaat        240
cgatattggc atttaactgt tttgttatac taagtctaga ttttaaatct tctagtaata        300
tgctatttaa tataaaagct tccacgtttt tgtatacatt tctttccata ttagtagcta        360
ctactaaatg attatcttct ttcatatctt gtagataaga tagactatct ttatctttat        420
tagtagaaaa tacttctggc catacatcgt taaattttt  tgttgttgtt agatataata        480
ttaaatatct agaggatcct attatttgtg gtaaaatgtt tatagagtaa atgatctgg         540 ctattaaaca taggccagtt accatagaat gctgcttccc gttacagtgt tttaccataa        600
ccatagatct gcctgtattg ttgatacata taacagctgt aaatcctaaa aaattcctat        660
cataattatt aatattaggt aattcatttc catgtgaaag atagactaat tttatatcct        720
ttacctccaa ataattattt acatctctta aacaatctat tttaatatca ttaactggta        780
```

```
ttttataata tccagaaagg tttgaagggg ttgatggaat aagtctatta acatcgttaa      840
gtaaattatt aatatcatga atctttatta tattataccc ataagttaaa tttatattta      900
ctttctcatc atctgactta gttagtttgt aataaggtgt gtctgaaaaa attaaaaggt      960
aattcgttga atgaagctgt atttgctgta tcattttat ctaattttgg agatttagca     1020
gtacttactt cattagaaga agaatctgcc agttcctgtc tattactgat atttcgtttc     1080
attattatat gatttatatt ttactttttc aattatatat actcatttga ctagttaatc     1140
aataaaaa                                                              1148
```

<210> SEQ ID NO 9
<211> LENGTH: 36
<212> TYPE: DNA
<213> ORGANISM: Artificial Sequence
<220> FEATURE:
<223> OTHER INFORMATION: 42K promoter

<400> SEQUENCE: 9

```
attctcaaaa ttgaaaatat ataattacaa tataaa                                 36
```

<210> SEQ ID NO 10
<211> LENGTH: 549
<212> TYPE: DNA
<213> ORGANISM: Artificial Sequence
<220> FEATURE:
<223> OTHER INFORMATION: cOX40L

<400> SEQUENCE: 10

```
atggaaggag tacaaccatt agatcaaaat gttggaaata caccaggaag aagatttcaa       60
aaaaataaag tattattagt agcagcaata attcaaggtt taggattatt attatgtttt      120
acatatatat gtttacactt ttatgcatct caagtaccac tcaatatccc acctatacaa      180
agtataagag ttcagtttac aagatgtgaa atgaaaaag ttgtattat tacatctcca       240 agtaaagatg aaactatgaa agtacaagat aattcaataa tcataaattg tgatggtttt      300
tacttaatta gttaaaaagg atattttca gaagaattat cattatcttt atattataga      360
aaaggtagag gacctttatt ttctttatca aaagtaacat cagttgattc tattggagtt      420
gcatatttgg cttttaaaga taagtatat tttaatgtta caactcattc tactagttat      480
aaagatatac aagtaaatgg tggtgaatta atattaatac atcaaaatcc tggtggattt      540
tgtgcttat                                                              549
```

<210> SEQ ID NO 11
<211> LENGTH: 364
<212> TYPE: DNA
<213> ORGANISM: Artificial Sequence
<220> FEATURE:
<223> OTHER INFORMATION: vCP3015 C6L arm

<400> SEQUENCE: 11

```
gtaagtaagt attttatt aatacttttt attgtactta tgttaaatat aactgatgat       60
aacaaaatcc attatgtatt atttataact gtaattctt tagcgtagtt agatgtccaa      120
tctctctcaa atacatcggc tatcttttta gtgagatttt gatctatgca gttgaaactt      180
atgaacgcgt gatgattaaa atgtgaaccg tccaaatttg cagtcattat atgagcgtat      240
ctattatcta ctatcatcat ctttgagtta ttaaatatcat ctactttaga attgatagga      300
aatatgaata cctttgtagt aatatctata ctatctacac ctaactcatt aagacttttg      360
``` atag 364

<210> SEQ ID NO 12
<211> LENGTH: 183
<212> TYPE: PRT
<213> ORGANISM: Artificial Sequence
<220> FEATURE:
<223> OTHER INFORMATION: Predicted amino acid sequence of synthetic cOX40L

<400> SEQUENCE: 12

```
Met Glu Gly Val Gln Pro Leu Asp Gln Asn Val Gly Asn Thr Pro Gly
1               5                   10                  15

Arg Arg Phe Gln Lys Asn Lys Val Leu Leu Val Ala Ala Ile Ile Gln
            20                  25                  30

Gly Leu Gly Leu Leu Leu Cys Phe Thr Tyr Ile Cys Leu His Phe Tyr
        35                  40                  45

Ala Ser Gln Val Pro Pro Gln Tyr Pro Pro Ile Gln Ser Ile Arg Val
    50                  55                  60

Gln Phe Thr Arg Cys Glu Asn Glu Lys Gly Cys Ile Ile Thr Ser Pro
65                  70                  75                  80

Ser Lys Asp Glu Thr Met Lys Val Gln Asp Asn Ser Ile Ile Ile Asn
                85                  90                  95

Cys Asp Gly Phe Tyr Leu Ile Ser Leu Lys Gly Tyr Phe Ser Glu Glu
            100                 105                 110

Leu Ser Leu Ser Leu Tyr Tyr Arg Lys Gly Arg Gly Pro Leu Phe Ser
        115                 120                 125

Leu Ser Lys Val Thr Ser Val Asp Ser Ile Gly Val Ala Tyr Leu Ala
    130                 135                 140

Phe Lys Asp Lys Val Tyr Phe Asn Val Thr Thr His Ser Thr Ser Tyr
145                 150                 155                 160

Lys Asp Ile Gln Val Asn Gly Gly Glu Leu Ile Leu Ile His Gln Asn
                165                 170                 175

Pro Gly Gly Phe Cys Ala Tyr
            180
```

<210> SEQ ID NO 13
<211> LENGTH: 3279
<212> TYPE: DNA
<213> ORGANISM: Artificial Sequence
<220> FEATURE:
<223> OTHER INFORMATION: Fragment of vCP3015 C5 Right arm to Classic Rabies G

<400> SEQUENCE: 13

```
gctataaata tgcattggaa aaataatcca tttaaagaaa ggattcaaat actacaaaac     60
ctaagcgata atatgttaac taagcttatt cttaacgacg ctttaaatat acacaaataa    120
acataatttt tgtataacct aacaaataac taaaacataa aaataataaa aggaaatgta    180
atatcgtaat tattttactc aggaatgggg ttaaatattt atatcacgtg tatatctata    240
ctgttatcgt atactcttta caattactat tacgaatatg caagagataa taagattacg    300
tatttaagag aatcttgtca tgataattgg gtacgacata gtgataaatg ctatttcgca    360
tcgttacata aagtcagttg gaaagatgga tttgacagat gtaacttaat aggtgcaaaa    420
atgttaaata acagcattct atcggaagat aggataccag ttatattata caaaaatcac    480
tggttggata aaacagattc tgcaatattc gtaaaagatg aagattactg cgaatttgta    540
aactatgaca ataaaaagcc atttatctca acgacatcgt gtaattcttc catgttttat    600
```

```
gtatgtgttt cagatattat gagattacta taaacttttt gtatacttat attccgtaaa      660
ctatattaat catgaagaaa atgaaaaagt atagaagctg ttcacgagcg gttgttgaaa      720
acaacaaaat tatacattca agatggctta catatacgtc tgtgaggcta tcatggataa      780
tgacaatgca tctctaaata ggttttttgga caatggattc gaccctaaca cggaatatgg      840
tactctacaa tctcctcttg aaatggctgt aatgttcaag aataccgagg ctataaaaat      900
cttgatgagg tatggagcta aacctgtagt tactgaatgc acaacttctt gtctgcatga      960
tgcggtgttg agagacgact acaaaatagt gaaagatctg ttgaagaata actatgtaaa     1020
caatgttctt tacagcggag gctttactcc tttgtgtttg gcagcttacc ttaacaaagt     1080
taatttggtt aaacttctat tggctcattc ggcggatgta gatatttcaa acacggatcg     1140
gttaactcct ctacatatag ccgtatcaaa taaaaattta acaatggtta aacttctatt     1200
gaacaaaggt gctgatactg acttgctgga taacatggga cgtactcctt taatgatcgc     1260
tgtacaatct ggaaatattg aaatatgtag cacactactt aaaaaaaata aaatgtccag     1320
aactgggaaa aattgatctt gccagctgta attcatggta gaaaagaagt gctcaggcta     1380
cttttcaaca aaggagcaga tgtaaactac atctttgaaa gaaatggaaa atcatatact     1440
gttttggaat tgattaaaga aagttactct gagacacaaa agaggtagct gaagtggtac     1500
tctcaaaagc ttcccgggtt aattaattag ttattagaca aggtgaaaac gaaactattt     1560
gtagcttaat taattagagc ttctttattc tatacttaaa aagtgaaaat aaatacaaag     1620
gttcttgagg gttgtgttaa attgaaagcg agaaataatc ataaattatt tcattatcgc     1680
gatatccgtt aagtttgtat cgtaatggtt cctcaagctc tcctgtttgt acccettctg     1740 gttttttccgt tgtgttttgg aaaattccct atttacacaa tcccagacaa gcttggtccc     1800
tggagcccga ttgacataca tcacctcagc tgcccaaaca atttggtagt ggaggacgaa     1860
ggatgcacca acctgtcagg gttctcctac atggaactta aagttggata catcttagcc     1920
ataaaaatga acgggttcac ttgcacaggc gttgtgacgg aggctgaaac ctacactaac     1980
ttcgttggtt atgtcacaac cacgttcaaa agaaagcatt tccgcccaac accagatgca     2040
tgtagagccg cgtacaactg gaagatggcc ggtgaccccca gatatgaaga gtctctacac     2100
aatccgtacc ctgactaccg ctggcttcga actgtaaaaa ccaccaagga gtctctcgtt     2160
atcatatctc caagtgtagc agatttggac ccatatgaca gatcccttca ctcgagggtc     2220
ttccctagcg ggaagtgctc aggagtagcg gtgtcttcta cctactgctc cactaaccac     2280
gattacacca tttggatgcc cgagaatccg agactaggga tgtcttgtga cattttttacc     2340 aatagtagag ggaagagagc atccaaaggg agtgagactt gcggctttgt agatgaaaga     2400
ggcctatata agtctttaaa aggagcatgc aaactcaagt tatgtggagt tctaggactt     2460
agacttatgg atggaacatg ggtcgcgatg caaacatcaa atgaaaccaa atggtgccct     2520
cccgatcagt tggtgaacct gcacgacttt cgctcagacg aaaattgagca ccttgttgta     2580 gaggagttgg tcaggaagag agaggagtgt ctggatgcac tagagtccat catgacaacc     2640
aagtcagtga gtttcagacg tctcagtcat ttaagaaaac ttgtccctgg gtttggaaaa     2700
gcatatacca tattcaacaa gaccttgatg gaagccgatg ctcactacaa gtcagtcaga     2760
acttggaatg agatcctccc ttcaaaaggg tgtttaagag ttggggggag gtgtcatcct     2820
catgtgaacg gggtgttttt caatggtata atattaggac ctgacggcaa tgtcttaatc     2880
ccagagatgc aatcatccct cctccagcaa catatggagt tgttggaatc ctcggttatc     2940
```

```
cccccttgtgc acccccctggc agacccgtct accgttttca aggacggtga cgaggctgag    3000
gattttgttg aagttcacct tcccgatgtg cacaatcagg tctcaggagt tgacttgggt    3060
ctcccgaact gggggaagta tgtattactg agtgcagggg ccctgactgc cttgatgttg    3120 ataatttttcc tgatgacatg ttgtagaaga gtcaatcgat cagaacctac gcaacacaat    3180
ctcagaggga cagggaggga ggtgtcagtc actccccaaa gcgggaagat catatcttca    3240
tgggaatcac acaagagtgg gggtgagacc agactgtga                           3279

<210> SEQ ID NO 14
<211> LENGTH: 1508
<212> TYPE: DNA
<213> ORGANISM: Artificial Sequence
<220> FEATURE:
<223> OTHER INFORMATION: vCP3015 C5R

<400> SEQUENCE: 14
gctataaata tgcattggaa aaataatcca tttaaagaaa ggattcaaat actacaaaac     60
ctaagcgata atatgttaac taagcttatt cttaacgacg ctttaaatat acacaaataa    120
acataatttt tgtataacct aacaaataac taaaacataa aataataaa aggaaatgta    180 atatcgtaat tattttactc aggaatgggg ttaaatattt atatcacgtg tatatctata    240
ctgttatcgt atactcttta caattactat tacgaatatg caagagataa taagattacg    300
tatttaagag aatcttgtca tgataattgg gtacgacata gtgataaatg ctatttcgca    360
tcgttacata aagtcagttg aaagatgga tttgacagat gtaacttaat aggtgcaaaa    420
atgttaaata acagcattct atcggaagat aggataccag ttatattata caaaaatcac    480
tggttggata aaacagattc tgcaatattc gtaaagatg aagattactg cgaatttgta    540
aactatgaca ataaaaagcc atttatctca acgacatcgt gtaattcttc catgttttat    600
gtatgtgttt cagatattat gagattacta taaactttttt gtatacttat attccgtaaa    660
ctatattaat catgaagaaa atgaaaaagt atagaagctg ttcacgagcg gttgttgaaa    720
acaacaaaat tatacattca agatggctta catatacgtc tgtgaggcta tcatggataa    780
tgacaatgca tctctaaata ggttttttgga caatggattc gaccctaaca cggaatatgg    840
tactctacaa tctcctcttg aaatggctgt aatgttcaag aataccgagg ctataaaaat    900
cttgatgagg tatggagcta aacctgtagt tactgaatgc acaacttctt gtctgcatga    960
tgcggtgttg agagacgact acaaaatagt gaaagatctg ttgaagaata actatgtaaa    1020
caatgttctt tacagcggag gctttactcc tttgtgtttg gcagcttacc ttaacaaagt    1080
taatttggtt aaacttctat tggctcattc ggcggatgta gatatttcaa acacggatcg    1140
gttaactcct ctacatatag ccgtatcaaa taaaaattta acaatggtta aacttctatt    1200
gaacaaaggt gctgatactg acttgctgga taacatggga cgtactcctt taatgatcgc    1260
tgtacaatct ggaaatattg aaatatgtag cacactactt aaaaaaaata aaatgtccag    1320
aactgggaaa aattgatctt gccagctgta attcatggta gaaaagaagt gctcaggcta    1380
cttttcaaca aggagcagaa tgtaaactac atctttgaaa gaaatggaaa atcatatact    1440
gttttggaat tgattaaaga aagttactct gagacacaaa agaggtagct gaagtggtac    1500
tctcaaaa                                                             1508

<210> SEQ ID NO 15
<211> LENGTH: 124
<212> TYPE: DNA
<213> ORGANISM: Artificial Sequence
```

-continued

```
<220> FEATURE:
<223> OTHER INFORMATION: vCP3015 H6 promoter

<400> SEQUENCE: 15
ttctttattc tatacttaaa aagtgaaaat aaatacaaag gttcttgagg gttgtgttaa 60
attgaaagcg agaaataatc ataaattatt tcattatcgc gatatccgtt aagtttgtat 120
cgta 124

<210> SEQ ID NO 16
<211> LENGTH: 1572
<212> TYPE: DNA
<213> ORGANISM: Artificial Sequence
<220> FEATURE:
<223> OTHER INFORMATION: Classic rabies G gene (wild type)

<400> SEQUENCE: 16
atggttcctc aagctctcct gtttgtaccc cttctggttt ttccgttgtg ttttggaaaa 60
ttccctattt acacaatccc agacaagctt ggtccctgga gcccgattga catacatcac 120
ctcagctgcc caaacaattt ggtagtggag gacgaaggat gcaccaacct gtcagggttc 180
tcctacatgg aacttaaagt tggatacatc ttagccataa aatgaacgg gttcacttgc 240
acaggcgttg tgacggaggc tgaaacctac actaacttcg ttggttatgt cacaaccacg 300
ttcaaaagaa agcatttccg cccaacacca gatgcatgta gagccgcgta caactggaag 360
atggccggtg accccagata tgaagagtct ctacacaatc cgtaccctga ctaccgctgg 420
cttcgaactg taaaaaccac caaggagtct ctcgttatca tatctccaag tgtagcagat 480
ttggacccat atgacagatc ccttcactcg agggtcttcc ctagcgggaa gtgctcagga 540
gtagcggtgt cttctaccta ctgctccact aaccacgatt acaccatttg gatgcccgag 600
aatccgagac tagggatgtc ttgtgacatt tttaccaata gtagagggaa gagagcatcc 660
aaagggagtg agacttgcgg ctttgtagat gaaagaggcc tatataagtc tttaaaagga 720
gcatgcaaac tcaagttatg tggagttcta ggacttagac ttatggatgg aacatgggtc 780
gcgatgcaaa catcaaatga aaccaaatgg tgccctcccg atcagttggt gaacctgcac 840
gactttcgct cagacgaaat tgagcacctt gttgtagagg agttggtcag gaagagagag 900
gagtgtctgg atgcactaga gtccatcatg acaaccaagt cagtgagttt cagacgtctc 960
agtcatttaa gaaaacttgt ccctgggttt ggaaaagcat ataccatatt caacaagacc 1020
ttgatggaag ccgatgctca ctacaagtca gtcagaactt ggaatgagat cctcccttca 1080
aaagggtgtt taagagttgg ggggaggtgt catcctcatg tgaacggggt gtttttcaat 1140
ggtataatat taggacctga cggcaatgtc ttaatcccag agatgcaatc atccctcctc 1200
cagcaacata tggagttgtt ggaatcctcg gttatccccc ttgtgcaccc cctggcagac 1260
ccgtctaccg ttttcaagga cggtgacgag gctgaggatt ttgttgaagt tcaccttccc 1320
gatgtgcaca atcaggtctc aggagttgac ttgggtctcc cgaactgggg gaagtatgta 1380
ttactgagtg caggggccct gactgccttg atgttgataa ttttcctgat gacatgttgt 1440
agaagagtca atcgatcaga acctacgcaa cacaatctca gagggacagg gagggaggtg 1500
tcagtcactc cccaaagcgg gaagatcata tcttcatggg aatcacacaa gagtgggggt 1560
gagaccagac tg 1572

<210> SEQ ID NO 17
<211> LENGTH: 2141
<212> TYPE: DNA
```

<213> ORGANISM: Artificial Sequence
<220> FEATURE:
<223> OTHER INFORMATION: vCP3012 C6 Right arm to C6 Left arm

<400> SEQUENCE: 17

```
gttctaaagt tctttcctcc gaaggtatag aacaaagtat ttcttctaca tccttactat      60
ttattgcagc ttttaacagc ctatcacgta tcctatttt agtattggta gaacgtttta     120
gttctaaagt taaaatatta gacataattg gcatattgct tattccttgc atagttgagt     180
ctgtagatcg tttcagtata tcactgatta atgtactact gttatgatga aatatagaat     240
cgatattggc atttaactgt tttgttatac taagtctaga ttttaaatct tctagtaata     300
tgctatttaa tataaaagct tccacgtttt tgtatacatt tctttccata ttagtagcta     360
ctactaaatg attatcttct ttcatatctt gtagataaga tagactatct ttatctttat     420
tagtagaaaa tacttctggc catacatcgt taaattttt tgttgttgtt agatataata     480
ttaaatatct agaggatcct attatttgtg gtaaaatgtt tatagagtaa aatgatctgg     540
ctattaaaca taggccagtt accatagaat gctgcttccc gttacagtgt tttaccataa     600
ccatagatct gcctgtattg ttgatacata taacagctgt aaatcctaaa aaattcctat     660
cataattatt aatattaggt aattcatttc catgtgaaag atagactaat tttatatcct     720
ttacctccaa ataattattt acatctctta aacaatctat tttaatatca ttaactggta     780
ttttataata tccagaaagg tttgaagggg ttgatggaat aagtctatta acatcgttaa     840
gtaaattatt aatatcatga atctttatta tattataccc ataagttaaa tttatattta     900
ctttctcatc atctgactta gttagtttgt aataaggtgt gtctgaaaaa attaaaaggt     960
aattcgttga atgaagctgt atttgctgta tcatttttat ctaattttgg agatttagca    1020
gtacttactt cattagaaga agaatctgcc agttcctgtc tattactgat atttcgtttc    1080
attattatat gatttatatt ttacttttc aattatatat actcatttga ctagttaatc    1140
aataaaaga attctcaaaa ttgaaaatat ataattacaa tataaaatgg aaggagtaca    1200
accattagat caaaatgttg gaaatacacc aggaagaaga tttcaaaaaa ataaagtatt    1260
attagtagca gcaataattc aaggtttagg attattatta tgttttacat atatatgttt    1320
acactttat gcatctcaag taccacctca atatccacct atacaaagta taagagttca    1380
gtttacaaga tgtgaaaatg aaaaaggttg tattattaca tctccaagta aagatgaaac    1440
tatgaaagta caagataatt caataatcat aaattgtgat ggttttact taattagttt    1500
aaaaggatat ttttcagaag aattatcatt atctttatat tatagaaaag gtagaggacc    1560
tttatttct ttatcaaaag taacatcagt tgattctatt ggagttgcat atttggcttt    1620
taaagataaa gtatattta atgttacaac tcattctact agttataaag atatacaagt    1680
aaatggtggt gaattaatat taatacatca aaatcctggt ggattttgtg cttattaatt    1740
tttatcccgg ttttatag ctaattagtc attttcgta agtaagtatt tttatttaat    1800
acttttatt gtacttatgt taaatataac tgatgataac aaaatccatt atgtattatt    1860
tataactgta atttctttag cgtagttaga tgtccaatct ctctcaaata catcggctat    1920
cttttagtg agattttgat ctatgcagtt gaaacttatg aacgcgtgat gattaaaatg    1980
tgaaccgtcc aaatttgcag tcattatatg agcgtatcta ttatctacta tcatcatctt    2040
tgagttatta atatcatcta ctttagaatt gataggaaat atgaataacct ttgtagtaat    2100
atctatacta tctacaccta actcattaag acttttgata g                       2141
```

<210> SEQ ID NO 18
<211> LENGTH: 1148
<212> TYPE: DNA
<213> ORGANISM: Artificial Sequence
<220> FEATURE:
<223> OTHER INFORMATION: vCP3012 C6R arm

<400> SEQUENCE: 18

```
gttctaaagt tctttcctcc gaaggtatag aacaaagtat tcttctaca tccttactat      60
ttattgcagc ttttaacagc ctatcacgta tcctattttt agtattggta gaacgtttta    120
gttctaaagt taaaatatta gacataattg gcatattgct tattccttgc atagttgagt    180
ctgtagatcg tttcagtata tcactgatta atgtactact gttatgatga atatagaat    240
cgatattggc atttaactgt tttgttatac taagtctaga ttttaaatct tctagtaata    300
tgctatttaa tataaaagct tccacgtttt tgtatacatt tctttccata ttagtagcta    360
ctactaaatg attatcttct ttcatatctt gtagataaga tagactatct ttatctttat    420
tagtagaaaa tacttctggc catacatcgt taaattttt tgttgttgtt agatataata     480
ttaaatatct agaggatcct attatttgtg gtaaaatgtt tatagagtaa aatgatctgg    540
ctattaaaca taggccagtt accatagaat gctgcttccc gttacagtgt tttaccataa    600
ccatagatct gcctgtattg ttgatacata taacagctgt aaatcctaaa aaattcctat    660
cataattatt aatattaggt aattcatttc catgtgaaag atagactaat tttatatcct    720
ttacctccaa ataattattt acatctctta aacaatctat tttaatatca ttaactggta    780
ttttataata tccagaaagg tttgaagggg ttgatggaat aagtctatta acatcgttaa    840
gtaaattatt aatatcatga atctttatta tattataccc ataagttaaa tttatattta    900
cttctctcatc atctgactta gttagtttgt aataaggtgt gtctgaaaaa attaaaaggt    960
aattcgttga atgaagctgt atttgctgta tcatttttat ctaattttgg agatttagca   1020
gtacttactt cattagaaga agaatctgcc agttcctgtc tattactgat atttcgtttc   1080
attattatat gatttatatt ttacttttc aattatatat actcatttga ctagttaatc   1140
aataaaaa                                                            1148
```

<210> SEQ ID NO 19
<211> LENGTH: 365
<212> TYPE: DNA
<213> ORGANISM: Artificial Sequence
<220> FEATURE:
<223> OTHER INFORMATION: vCP3012 C6L arm

<400> SEQUENCE: 19

```
cgtaagtaag tattttatt taatactttt tattgtactt atgttaaata taactgatga      60
taacaaaatc cattatgtat tatttataac tgtaatttct ttagcgtagt tagatgtcca   120
atctctctca aatacatcgg ctatcttttt agtgagattt tgatctatgc agttgaaact   180
tatgaacgcg tgatgattaa aatgtgaacc gtccaaattt gcagtcatta tatgagcgta   240
tctattatct actatcatca tctttgagtt attaatatca tctactttag aattgatagg   300
aaatatgaat acctttgtag taatatctat actatctaca cctaactcat taagacttttt   360
gatag                                                               365
```

<210> SEQ ID NO 20
<211> LENGTH: 4089
<212> TYPE: DNA
<213> ORGANISM: Artificial Sequence
<220> FEATURE:

<223> OTHER INFORMATION: vCP3012 C3R arm to C3L arm

<400> SEQUENCE: 20

| | | | | | |
|---|---|---|---|---|---|
| tgtaatgggg | ttttacctaa | atcatcttgt | tcgtttatag | gcactccgtg | atttataagt | 60 |
| aacgctatta | tatcgtaact | acaattattt | ttaagtgcct | ttatgagata | ctgtttatgc | 120 |
| aaaaataaac | ttttatctat | tttaatacta | ttatctaaca | atatcctaat | taaatctata | 180 |
| ttcttatact | ttatagcgta | atgtaacgga | gtttcaaaat | ttctagtttg | tatattaaga | 240 |
| tcaatattaa | aatctataaa | tattttatac | atatcatcag | atatcttatc | atacagtaca | 300 |
| tcgtaataat | ttagaaagaa | tctattacaa | ttaacacctt | ttttttaataa | atatctagtt | 360 |
| aatgacttat | tgtttctata | tacagaaata | tataacggac | tatttccaga | atgtatctgt | 420 |
| tctatgtcag | cgccagaatc | tattagtagt | ttagcaattt | ctgtattatc | taaactagca | 480 |
| gctttatgaa | gaggaggatt | tttacattt | aaaatatcgg | caccgtgttc | tagtaataat | 540 |
| tttaccattt | ctatatcaga | aatacttacg | gctaaatacaa | aagacgttga | tagtatattt | 600 |
| acgttattgt | atttgcattt | tttaagtata | taccttacta | aatttatatc | tctataccttt | 660 |
| atagctttat | gcagttcatt | tataagtctt | ccattactca | tttctggtaa | tgaagtatta | 720 |
| tatatcatta | tgatattatc | tctattttat | tctaataaaa | accgttatca | tgttatttat | 780 |
| tatttgttat | aattatacta | tttaataaat | tataccaaat | acttagatac | ttattaatac | 840 |
| catcctagaa | cttgtatttc | ttgcccccta | aacttggaca | tgcactccat | taggcgtttc | 900 |
| ttgttttcga | catcgtcctc | cttaacatat | cctactgtta | tgtgaggatt | ccacggatta | 960 |
| tctactgtga | tatcaccaaa | cacgtccttc | gaacagggta | ccgcattcag | cagaacattt | 1020 |
| cttagggctc | taagttcatc | agatacctcc | agtttcataa | ctacagcgca | tcctttcgct | 1080 |
| cccaactgtt | tagaggcgtt | actctgagga | aaacacatct | cttctttaca | gactatagaa | 1140 |
| atagtctgta | aatcttgatc | agttatttgc | ttttgaaat | tttcaaatct | atcacattga | 1200 |
| tccatatttg | ctattccaag | agttatatga | ggaaaaatat | cacatcctgt | catgtatttt | 1260 |
| attgtaacat | tattataatc | tgtaacatca | gtatctaacc | taacgtcgta | aaagttaaca | 1320 |
| gatgcccagt | tactataatc | ccaaggaacc | ttaacatcta | atcccattaa | aatagtatcc | 1380 |
| tttctactat | tttttcatt | ggcaagtatg | tggcttagtt | tacacaaaat | tcctgccatt | 1440 |
| ttgtaacgat | agcgaagcaa | tagcttgtat | gcttttatt | tgattaacta | gtcataaaaa | 1500 |
| tcgggatccc | tcgagatgag | ataaagtgaa | aatatatatc | attatattac | aaagtacaat | 1560 |
| tatttaggtt | taatcatggt | gccccaggcc | ctgctgttcg | tgccctgct | ggtgttcccc | 1620 |
| ctgtgcttcg | gcaagttccc | catctacacc | atccccgaca | agctgggccc | ctggagcccc | 1680 |
| atcgacatcc | accacctgag | ctgccccaac | aatctggtgg | tggaggatga | gggctgcacc | 1740 |
| aatctgagcg | gcttcagcta | catggagctg | aaagtgggct | acatcctggc | catcaagatg | 1800 |
| aacggcttca | cctgcaccgg | cgtggtgacc | gaggccgaga | cctacaccaa | ctttgtgggc | 1860 |
| tacgtgacca | ccaccttcaa | gcggaagcac | ttcagaccta | cccccgacgc | ctgcagagcc | 1920 |
| gcctacaact | ggaagatggc | cggcgaccct | agatacgagg | agagcctgca | caacccctac | 1980 |
| cccgactaca | gatggctgcg | gaccgtgaaa | accaccaagg | agtccctggt | gatcatcagc | 2040 |
| cctagcgtgg | ccgatctgga | cccctacgac | agaagcctgc | acagcagagt | gttccctagc | 2100 |
| ggcaagtgca | gcggcgtggc | cgtgtccagc | acctactgca | gcaccaacca | cgactacacc | 2160 |
| atctggatgc | ccgagaaccc | tagactgggc | atgagctgcg | acatcttcac | caacagccgg | 2220 |
| ggcaagagag | ccagcaaggg | cagcgagacc | tgcggcttcg | tggacgagag | aggcctgtac | 2280 |

-continued

```
aagagcctga agggcgcctg caagctgaag ctgtgcggcg tgctgggcct gagactgatg    2340
gacggcacct gggtggccat gcagaccagc aacgagacca gtggtgccc tcctgaccag     2400 ctggtgaacc tgcacgactt ccggagcgat gagatcgagc acctggtggt ggaagagctg    2460
gtgcggaaga gagaggagtg cctggacgcc tggagagca tcatgaccac caagagcgtg    2520
tccttccgga gactgagcca cctgagaaag ctggtgcccg gctttggcaa ggcctacaca    2580
atcttcaaca agaccctgat ggaggccgat gcccactaca gtctgtgcg gacctggaac    2640 gagatcctgc ctagcaaggg ctgcctgaga gtgggcggca gatgccaccc ccacgtgaac    2700
ggcgtgttct tcaacggcat catcctgggc cctgacggca cgtgctgat ccctgagatg     2760 cagagcagcc tgctgcagca gcacatggaa ctgctggaga gcagcgtgat ccccctggtg    2820 cacccctgg ccgaccccag caccgtgttc aaggatggcg acgaggccga ggacttcgtg     2880
gaggtgcacc tgcccgatgt gcacaaccag gtgtccggcg tggacctggg cctgcccaac    2940
tggggcaagt acgtgctgct gagcgccgga gccctgaccg ccctgatgct gatcatcttc    3000
ctgatgacct gctgccggag ggtgaacaga agcgagccca cccagcacaa cctgagaggc    3060
accggcagag aggtgtccgt gacccccag agcggcaaga tcatcagcag ctgggagagc     3120
cacaagagcg gcggagagac cagactatga ttttatgcc cgggttttta tagctaatta     3180
gtcaaatgtg agttaatatt agtatactac attactaatt tattacatat tcatttatat    3240
caatctagta gcatttagct tttataaaac aatataactg aatagtacat actttactaa    3300
taagttataa ataagagata catatttata gtattttact ttctacactg aatataataa    3360
tataattata caaatataat ttttaatact atatagtata taactgaaat aaaataccag    3420
tgtaatatag ttattataca tttataccac atcaaagatg agttataaca tcagtgtcac    3480
tgttagcaac agtagttata cgatgagtag ttactctcgt atggcgttag tatgtatgta    3540
tcttctagtt ttcttagtag gcattatagg aaacgtcaag cttataaggt tattaatggt    3600
atctagaaat atatctatta taccgtttct caacttggga atagccgatt tgctgtttgt    3660
gatattcata cctttataca ttatatacat actaagtaat ttccattggc attttggtaa    3720
agcactttgt aaaattagtt cttctttttt tacttctaac atgtttgcaa gtatattttt    3780
aataactgta ataagcgtat atagatatgt aaaaattacc cttcctggat ttacctataa    3840
atatgttaac attagaaata tgtacattac tatattttc atatggatta tttctattat    3900
actagggatt cctgctcttt actttagaaa tactatcgta acaaaaaata acgacacgct    3960
gtgtattaat cattatcatg ataatagaga aattgctgaa ttgatttaca aagttattat    4020
ctgtatcaga tttattttag gatacctact acctacgata attatactcg tatgctatac    4080
gttactgat                                                            4089
```

<210> SEQ ID NO 21
<211> LENGTH: 1471
<212> TYPE: DNA
<213> ORGANISM: Artificial Sequence
<220> FEATURE:
<223> OTHER INFORMATION: vCP3012 C3R arm

<400> SEQUENCE: 21

```
tgtaatgggg ttttacctaa atcatcttgt tcgtttatag gcactccgtg atttataagt     60
aacgctatta tatcgtaact acaattattt ttaagtgcct ttatgagata ctgtttatgc    120
aaaaataaac tttatctat tttaatacta ttatctaaca atatcctaat taaatctata    180
```

-continued

```
ttcttatact ttatagcgta atgtaacgga gtttcaaaat ttctagtttg tatattaaga        240
tcaatattaa aatctataaa tattttatac atatcatcag atatcttatc atacagtaca        300
tcgtaataat ttagaaagaa tctattacaa ttaacacctt tttttaataa atatctagtt        360
aatgacttat tgtttctata tacagaaata tataacggac tatttccaga atgtatctgt        420
tctatgtcag cgccagaatc tattagtagt ttagcaattt ctgtattatc taaactagca        480 gcttatgaa gaggaggatt tttacatttt aaaatatcgg caccgtgttc tagtaataat         540
tttaccattt ctatatcaga aatacttacg gctaaataca aagacgttga tagtatattt        600
acgttattgt atttgcattt tttaagtata taccttacta aatttatatc tctataccct        660
atagctttat gcagttcatt tataagtctt ccattactca tttctggtaa tgaagtatta        720
tatatcatta tgatattatc tctattttat tctaataaaa accgttatca tgttatttat        780
tatttgttat aattatacta tttaataaat tataccaaat acttagatac ttattaatac        840
catcctagaa cttgtatttc ttgccccta aacttggaca tgcactccat taggcgtttc         900
ttgttttcga catcgtcctc cttaacatat cctactgtta tgtgaggatt ccacggatta       960
tctactgtga tatcaccaaa cacgtccttc gaacagggta ccgcattcag cagaacattt      1020
cttagggctc taagttcatc agatacctcc agtttcataa ctacagcgca tcctttcgct      1080
cccaactgtt tagaggcgtt actctgagga aaacacatct cttctttaca gactatagaa       1140
atagtctgta atcttgatc agttatttgc tttttgaaat tttcaaatct atcacattga        1200
tccatatttg ctattccaag agttatatga ggaaaaatat cacatcctgt catgtatttt       1260
attgtaacat tattataatc tgtaacatca gtatctaacc taacgtcgta aaagttaaca       1320
gatgcccagt tactataatc ccaaggaacc ttaacatcta atcccattaa aatagtatcc       1380
tttctactat ttttttcatt ggcaagtatg tggcttagtt tacacaaaat tcctgccatt       1440
ttgtaacgat agcgaagcaa tagcttgtat g                                       1471
```

<210> SEQ ID NO 22
<211> LENGTH: 907
<212> TYPE: DNA
<213> ORGANISM: Artificial Sequence
<220> FEATURE:
<223> OTHER INFORMATION: vCP3012 C3R arm

<400> SEQUENCE: 22

```
caaatgtgag ttaatattag tatactacat tactaattta ttacatattc atttatatca         60
atctagtagc atttagcttt tataaaacaa tataactgaa tagtacatac tttactaata        120
agttataaat aagagataca tatttatagt attttacttt ctacactgaa tataataata       180
taattataca aatataattt ttaatactat atagtatata actgaaataa ataccagtg        240 taatatagtt attatacatt ataccacat caaagatgag ttataacatc agtgtcactg        300
ttagcaacag tagttatacg atgagtagtt actctcgtat ggcgttagta tgtatgtatc       360
ttctagtttt cttagtaggc attataggaa acgtcaagct tataaggtta ttaatggtat       420
ctagaaatat atctattata ccgtttctca acttgggaat agccgatttg ctgtttgtga       480
tattcatacc tttatacatt atatacatac taagtaattt ccattggcat tttggtaaag      540
cactttgtaa aattagttct ttcttttta cttctaacat gtttgcaagt atattttaa        600 taactgtaat aagcgtatat agatatgtaa aaattcccct tcctggattt acctataaat       660
atgttaacat tagaaatatg tacattacta tattttcat atggattatt tctattatac       720
tagggattcc tgctctttac tttagaaata ctatcgtaac aaaaaataac gacacgctgt       780
```

| | |
|---|---|
| gtattaatca ttatcatgat aatagagaaa ttgctgaatt gatttacaaa gttattatct | 840 |
| gtatcagatt tattttagga tacctactac ctacgataat tatactcgta tgctatacgt | 900 |
| tactgat | 907 |

<210> SEQ ID NO 23
<211> LENGTH: 3279
<212> TYPE: DNA
<213> ORGANISM: Artificial Sequence
<220> FEATURE:
<223> OTHER INFORMATION: Fragment of vCP3012 - rabies virus G and flanking regions

<400> SEQUENCE: 23

| | |
|---|---|
| gctataaata tgcattggaa aaataatcca tttaaagaaa ggattcaaat actacaaaac | 60 |
| ctaagcgata atatgttaac taagcttatt cttaacgacg ctttaaatat acacaaataa | 120 |
| acataatttt tgtataacct aacaaataac taaaacataa aaataataaa aggaaatgta | 180 |
| atatcgtaat tattttactc aggaatgggg ttaaatattt atatcacgtg tatatctata | 240 |
| ctgttatcgt atactcttta caattactat tacgaatatg caagagataa taagattacg | 300 |
| tatttaagag aatcttgtca tgataattgg gtacgacata gtgataaatg ctatttcgca | 360 |
| tcgttacata aagtcagttg gaaagatgga tttgacagat gtaacttaat aggtgcaaaa | 420 |
| atgttaaata acagcattct atcggaagat aggataccag ttatattata caaaaatcac | 480 |
| tggttggata aaacagattc tgcaatattc gtaaagatg aagattactg cgaatttgta | 540 |
| aactatgaca ataaaaagcc atttatctca acgacatcgt gtaattcttc catgttttat | 600 |
| gtatgtgttt cagatattat gagattacta taaacttttt gtatacttat attccgtaaa | 660 |
| ctatattaat catgaagaaa atgaaaaagt atagaagctg ttcacgagcg gttgttgaaa | 720 |
| acaacaaaat tatacattca agatggctta catatacgtc tgtgaggcta tcatggataa | 780 |
| tgacaatgca tctctaaata ggttttttgga caatggattc gaccctaaca cggaatatgg | 840 |
| tactctacaa tctcctcttg aaatggctgt aatgttcaag aataccgagg ctataaaaat | 900 |
| cttgatgagg tatggagcta aacctgtagt tactgaatgc acaacttctt gtctgcatga | 960 |
| tgcggtgttg agagacgact acaaaatagt gaaagatctg ttgaagaata actatgtaaa | 1020 |
| caatgttctt tacagcggag gctttactcc tttgtgtttg gcagcttacc ttaacaaagt | 1080 |
| taatttggtt aaacttctat tggctcattc ggcggatgta gatatttcaa acacggatcg | 1140 |
| gttaactcct ctacatatag ccgtatcaaa taaaaattta acaatggtta aacttctatt | 1200 |
| gaacaaaggt gctgatactg acttgctgga taacatggga cgtactcctt taatgatcgc | 1260 |
| tgtacaatct ggaaatattg aaatatgtag cacactactt aaaaaaaata aaatgtccag | 1320 |
| aactgggaaa aattgatctt gccagctgta attcatggta gaaaagaagt gctcaggcta | 1380 |
| cttttcaaca aaggagcaga tgtaaactac atctttgaaa gaaatggaaa atcatatact | 1440 |
| gttttggaat tgattaaaga aagttactct gagacacaaa agaggtagct gaagtggtac | 1500 |
| tctcaaaagc ttcccgggtt aattaattag ttattagaca aggtgaaaac gaaactattt | 1560 |
| gtagcttaat taattagagc ttcttttattc tatacttaaa aagtgaaaat aaatacaaag | 1620 |
| gttcttgagg gttgtgttaa attgaaagcg agaaataatc ataaattatt tcattatcgc | 1680 |
| gatatccgtt aagtttgtat cgtaatggtt cctcaagctc tcctgtttgt accccttctg | 1740 |
| gttttttccgt tgtgttttgg aaaattccct atttacacaa tcccagacaa gcttggtccc | 1800 |
| tggagcccga ttgacataca tcacctcagc tgcccaaaca atttggtagt ggaggacgaa | 1860 |

```
ggatgcacca acctgtcagg gttctcctac atggaactta aagttggata catcttagcc    1920
ataaaaatga acgggttcac ttgcacaggc gttgtgacgg aggctgaaac ctacactaac    1980
ttcgttggtt atgtcacaac cacgttcaaa agaaagcatt tccgcccaac accagatgca    2040
tgtagagccg cgtacaactg gaagatggcc ggtgacccca gatatgaaga gtctctacac    2100
aatccgtacc ctgactaccg ctggcttcga actgtaaaaa ccaccaagga gtctctcgtt    2160
atcatatctc caagtgtagc agatttggac ccatatgaca gatcccttca ctcgagggtc    2220
ttccctagcg ggaagtgctc aggagtagcg gtgtcttcta cctactgctc cactaaccac    2280
gattacacca tttggatgcc cgagaatccg agactaggga tgtcttgtga catttttacc    2340
aatagtagag ggaagagagc atccaaaggg agtgagactt gcggctttgt agatgaaaga    2400
ggcctatata agtctttaaa aggagcatgc aaactcaagt tatgtggagt tctaggactt    2460
agacttatgg atggaacatg ggtcgcgatg caaacatcaa atgaaaccaa atggtgccct    2520
cccgatcagt tggtgaacct gcacgacttt cgctcagacg aaattgagca ccttgttgta    2580
gaggagttgg tcaggaagag agaggagtgt ctggatgcac tagagtccat catgacaacc    2640
aagtcagtga gtttcagacg tctcagtcat ttaagaaaac ttgtccctgg gtttggaaaa    2700
gcatatacca tattcaacaa gaccttgatg gaagccgatg ctcactacaa gtcagtcaga    2760
acttggaatg agatcctccc ttcaaaaggg tgtttaagag ttgggggggag gtgtcatcct    2820 catgtgaacg gggtgttttt caatggtata atattaggac ctgacggcaa tgtcttaatc    2880
ccagagatgc aatcatccct cctccagcaa catatggagt tgttggaatc ctcggttatc    2940
ccccttgtgc accccctggc agacccgtct accgttttca aggacggtga cgaggctgag    3000
gattttgttg aagttcacct tcccgatgtg cacaatcagg tctcaggagt tgacttgggt    3060
ctcccgaact gggggaagta tgtattactg agtgcagggg ccctgactgc cttgatgttg    3120 ataatttttcc tgatgacatg ttgtagaaga gtcaatcgat cagaacctac gcaacacaat    3180
ctcagaggga caggagggga ggtgtcagtc actccccaaa gcgggaagat catatcttca    3240
tgggaatcac acaagagtgg gggtgagacc agactgtga                          3279
```

<210> SEQ ID NO 24
<211> LENGTH: 3279
<212> TYPE: DNA
<213> ORGANISM: Artificial Sequence
<220> FEATURE:
<223> OTHER INFORMATION: vCP3012 C5R arm

<400> SEQUENCE: 24

```
gctataaata tgcattggaa aaataatcca tttaaagaaa ggattcaaat actacaaaac     60
ctaagcgata atatgttaac taagcttatt cttaacgacg ctttaaatat acacaaataa    120
acataatttt tgtataacct aacaaataac taaaacataa aaataataaa aggaaatgta    180
atatcgtaat tattttactc aggaatgggg ttaaatattt atatcacgtg tatatctata    240
ctgttatcgt atactctta caattactat tacgaatatg caagagataa taagattacg    300
tatttaagag aatcttgtca tgataattgg gtacgacata gtgataaatg ctatttcgca    360
tcgttacata aagtcagttg gaaagatgga tttgacagat gtaacttaat aggtgcaaaa    420
atgttaaata acagcattct atcggaagat aggataccag ttatattata caaaaatcac    480
tggttggata aaacgagttc tgcaatattc gtaaagatg aagattactg cgaatttgta    540
aactatgaca ataaaaagcc attatctca acgacatcgt gtaattcttc catgttttat    600
```

```
gtatgtgttt cagatattat gagattacta taaactttt gtatacttat attccgtaaa    660
ctatattaat catgaagaaa atgaaaaagt atagaagctg ttcacgagcg gttgttgaaa    720
acaacaaaat tatacattca agatggctta catatacgtc tgtgaggcta tcatggataa    780
tgacaatgca tctctaaata ggttttgga caatggattc gaccctaaca cggaatatgg    840
tactctacaa tctcctcttg aaatggctgt aatgttcaag aataccgagg ctataaaaat    900
cttgatgagg tatggagcta aacctgtagt tactgaatgc acaacttctt gtctgcatga    960
tgcggtgttg agagacgact acaaaatagt gaaagatctg ttgaagaata actatgtaaa   1020
caatgttctt tacagcggag ctttactcc tttgtgtttg gcagcttacc ttaacaaagt   1080
taatttggtt aaacttctat tggctcattc ggcggatgta gatatttcaa acacggatcg   1140
gttaactcct ctacatatag ccgtatcaaa taaaaattta acaatggtta aacttctatt   1200
gaacaaaggt gctgatactg acttgctgga taacatggga cgtactcctt taatgatcgc   1260
tgtacaatct ggaaatattg aaatatgtag cacactactt aaaaaaaata aaatgtccag   1320
aactgggaaa aattgatctt gccagctgta attcatggta gaaaagaagt gctcaggcta   1380
cttttcaaca aaggagcaga tgtaaactac atctttgaaa gaaatggaaa atcatatact   1440
gttttggaat tgattaaaga aagttactct gagacacaaa agaggtagct gaagtggtac   1500
tctcaaaagc ttcccgggtt aattaattag ttattagaca aggtgaaaac gaaactattt   1560
gtagcttaat taattagagc ttcttattc tatacttaaa aagtgaaaat aaatacaaag   1620
gttcttgagg gttgtgttaa attgaaagcg agaaataatc ataaattatt tcattatcgc   1680
gatatccgtt aagtttgtat cgtaatggtt cctcaagctc tcctgtttgt accccttctg   1740 gttttttccgt tgtgttttgg aaaattccct atttacacaa tcccagacaa gcttggtccc   1800
tggagcccga ttgacataca tcacctcagc tgcccaaaca atttggtagt ggaggacgaa   1860
ggatgcacca acctgtcagg gttctcctac atggaactta aagttggata catcttagcc   1920
ataaaaatga acgggttcac ttgcacaggc gttgtgacgg aggctgaaac ctacactaac   1980
ttcgttggtt atgtcacaac cacgttcaaa agaaagcatt tccgcccaac accagatgca   2040
tgtagagccg cgtacaactg gaagatggcc ggtgacccca gatatgaaga gtctctacac   2100
aatccgtacc ctgactaccg ctggcttcga actgtaaaaa ccaccaagga gtctctcgtt   2160
atcatatctc caagtgtagc agatttggac ccatatgaca gatcccttca ctcgagggtc   2220
ttccctagcg ggaagtgctc aggagtagcg gtgtcttcta cctactgctc cactaaccac   2280
gattacacca tttggatgcc cgagaatccg agactaggga tgtcttgtga cattttttacc   2340 aatagtagag ggaagagagc atccaaaggg agtgagactt gcggctttgt agatgaaaga   2400
ggcctatata agtctttaaa aggagcatgc aaactcaagt tatgtggagt tctaggactt   2460
agacttatgg atggaacatg ggtcgcgatg caaacatcaa atgaaaccaa atggtgccct   2520
cccgatcagt tggtgaacct gcacgacttt cgctcagacg aaattgagca ccttgttgta   2580
gaggagttgg tcaggaagag agaggagtgt ctggatgcac tagagtccat catgacaacc   2640
aagtcagtga gtttcagacg tctcagtcat ttaagaaaac ttgtccctgg gtttggaaaa   2700
gcatatacca tattcaacaa gaccttgatg gaagccgatg ctcactacaa gtcagtcaga   2760
acttggaatg agatcctccc ttcaaagggg tgtttaagag ttgggggggag gtgtcatcct   2820 catgtgaacg gggtgttttt caatggtata atattaggac ctgacggcaa tgtcttaatc   2880
ccagagatgc aatcatccct cctccagcaa catatggagt tgttggaatc ctcggttatc   2940
ccccttgtgc accccctggc agacccgtct accgttttca aggacggtga cgaggctgag   3000
```
gattttgttg aagttcacct tcccgatgtg cacaatcagg tctcaggagt tgacttgggt    3060
ctcccgaact gggggaagta tgtattactg agtgcagggg ccctgactgc cttgatgttg    3120
ataattttcc tgatgacatg ttgtagaaga gtcaatcgat cagaacctac gcaacacaat    3180
ctcagaggga cagggaggga ggtgtcagtc actccccaaa gcgggaagat catatcttca    3240
tgggaatcac acaagagtgg gggtgagacc agactgtga                          3279

<210> SEQ ID NO 25
<211> LENGTH: 26
<212> TYPE: DNA
<213> ORGANISM: Artificial Sequence
<220> FEATURE:
<223> OTHER INFORMATION: C5R.1R primer

<400> SEQUENCE: 25
ctcttgcata ttcgtaatag taattg                                        26

<210> SEQ ID NO 26
<211> LENGTH: 25
<212> TYPE: DNA
<213> ORGANISM: Artificial Sequence
<220> FEATURE:
<223> OTHER INFORMATION: C5R.1F primer

<400> SEQUENCE: 26
attctatcgg aagataggat accag                                         25

<210> SEQ ID NO 27
<211> LENGTH: 25
<212> TYPE: DNA
<213> ORGANISM: Artificial Sequence
<220> FEATURE:
<223> OTHER INFORMATION: C5R.2R primer

<400> SEQUENCE: 27
tcaacaaccg ctcgtgaaca gcttc                                         25

<210> SEQ ID NO 28
<211> LENGTH: 26
<212> TYPE: DNA
<213> ORGANISM: Artificial Sequence
<220> FEATURE:
<223> OTHER INFORMATION: C5R.2F primer

<400> SEQUENCE: 28
atgcacaact tcttgtctgc atgatg                                        26

<210> SEQ ID NO 29
<211> LENGTH: 26
<212> TYPE: DNA
<213> ORGANISM: Artificial Sequence
<220> FEATURE:
<223> OTHER INFORMATION: C5R.3R primer

<400> SEQUENCE: 29
tacggctata tgtagaggag ttaacc                                        26

<210> SEQ ID NO 30
<211> LENGTH: 25
<212> TYPE: DNA
<213> ORGANISM: Artificial Sequence
<220> FEATURE:
<223> OTHER INFORMATION: C5R.3F primer

<400> SEQUENCE: 30
ctctgagaca caaaagaggt agctg                                    25

<210> SEQ ID NO 31
<211> LENGTH: 25
<212> TYPE: DNA
<213> ORGANISM: Artificial Sequence
<220> FEATURE:
<223> OTHER INFORMATION: C5L.1F primer

<400> SEQUENCE: 31
catcatgagc aacgcgttag tatat                                    25

<210> SEQ ID NO 32
<211> LENGTH: 21
<212> TYPE: DNA
<213> ORGANISM: Artificial Sequence
<220> FEATURE:
<223> OTHER INFORMATION: C5L.1R primer

<400> SEQUENCE: 32
ttagaaatta tgcattttag a                                        21

<210> SEQ ID NO 33
<211> LENGTH: 25
<212> TYPE: DNA
<213> ORGANISM: Artificial Sequence
<220> FEATURE:
<223> OTHER INFORMATION: C5L.2R primer

<400> SEQUENCE: 33
ggagatacct ttagatatgg atctg                                    25

<210> SEQ ID NO 34
<211> LENGTH: 25
<212> TYPE: DNA
<213> ORGANISM: Artificial Sequence
<220> FEATURE:
<223> OTHER INFORMATION: C5L.3R primer

<400> SEQUENCE: 34
ttgtaaccat agtatatctt agcgc                                    25

<210> SEQ ID NO 35
<211> LENGTH: 25
<212> TYPE: DNA
<213> ORGANISM: Artificial Sequence
<220> FEATURE:
<223> OTHER INFORMATION: 7634CXL-F primer

<400> SEQUENCE: 35
gttctcgtag gagagaacta ttgac                                    25

<210> SEQ ID NO 36
<211> LENGTH: 27
<212> TYPE: DNA
<213> ORGANISM: Artificial Sequence
<220> FEATURE:
<223> OTHER INFORMATION: 7635CXL-R primer

<400> SEQUENCE: 36
cgtcttcagc tgtaaacaaa tataatg                                  27

<210> SEQ ID NO 37
<211> LENGTH: 25

```
<212> TYPE: DNA
<213> ORGANISM: Artificial Sequence
<220> FEATURE:
<223> OTHER INFORMATION: CP65.1F primer

<400> SEQUENCE: 37
atggttcctc aggctctcct gtttg                                       25

<210> SEQ ID NO 38
<211> LENGTH: 25
<212> TYPE: DNA
<213> ORGANISM: Artificial Sequence
<220> FEATURE:
<223> OTHER INFORMATION: CP65.1R primer

<400> SEQUENCE: 38
tcacagtctg gtctcacccc cactc                                       25

<210> SEQ ID NO 39
<211> LENGTH: 20
<212> TYPE: DNA
<213> ORGANISM: Artificial Sequence
<220> FEATURE:
<223> OTHER INFORMATION: CP65.2R primer

<400> SEQUENCE: 39
gacccatgtt ccatccataa                                             20

<210> SEQ ID NO 40
<211> LENGTH: 22
<212> TYPE: DNA
<213> ORGANISM: Artificial Sequence
<220> FEATURE:
<223> OTHER INFORMATION: CP65.3F primer

<400> SEQUENCE: 40
gtctcacccc cactcttgtg tg                                          22

<210> SEQ ID NO 41
<211> LENGTH: 20
<212> TYPE: DNA
<213> ORGANISM: Artificial Sequence
<220> FEATURE:
<223> OTHER INFORMATION: CP65.4F primer

<400> SEQUENCE: 41
gaaaacggta gacgggtctg                                             20

<210> SEQ ID NO 42
<211> LENGTH: 23
<212> TYPE: DNA
<213> ORGANISM: Artificial Sequence
<220> FEATURE:
<223> OTHER INFORMATION: C3R.1F primer

<400> SEQUENCE: 42
catagcttta tgtaaaggag tat                                         23

<210> SEQ ID NO 43
<211> LENGTH: 20
<212> TYPE: DNA
<213> ORGANISM: Artificial Sequence
<220> FEATURE:
<223> OTHER INFORMATION: C3R.2F primer

<400> SEQUENCE: 43
```

-continued tgtaatgggg ttttacctaa                                                        20

<210> SEQ ID NO 44
<211> LENGTH: 22
<212> TYPE: DNA
<213> ORGANISM: Artificial Sequence
<220> FEATURE:
<223> OTHER INFORMATION: C3R.3F primer

<400> SEQUENCE: 44
gctttatgaa gaggaggatt tt                                                     22

<210> SEQ ID NO 45
<211> LENGTH: 20
<212> TYPE: DNA
<213> ORGANISM: Artificial Sequence
<220> FEATURE:
<223> OTHER INFORMATION: C3R.4F primer

<400> SEQUENCE: 45
gcattcagca gaacatttct                                                        20

<210> SEQ ID NO 46
<211> LENGTH: 20
<212> TYPE: DNA
<213> ORGANISM: Artificial Sequence
<220> FEATURE:
<223> OTHER INFORMATION: C3L.1F primer

<400> SEQUENCE: 46
tagttactct cgtatggcgt                                                        20

<210> SEQ ID NO 47
<211> LENGTH: 21
<212> TYPE: DNA
<213> ORGANISM: Artificial Sequence
<220> FEATURE:
<223> OTHER INFORMATION: C3L.1R primer

<400> SEQUENCE: 47
atcagtaacg tatagcatac g                                                      21

<210> SEQ ID NO 48
<211> LENGTH: 25
<212> TYPE: DNA
<213> ORGANISM: Artificial Sequence
<220> FEATURE:
<223> OTHER INFORMATION: C3L.2R primer

<400> SEQUENCE: 48
tacatatttc taatgttaac atatt                                                  25

<210> SEQ ID NO 49
<211> LENGTH: 20
<212> TYPE: DNA
<213> ORGANISM: Artificial Sequence
<220> FEATURE:
<223> OTHER INFORMATION: I3L.1F primer

<400> SEQUENCE: 49
ggatccctcg agatgagata                                                        20

<210> SEQ ID NO 50
<211> LENGTH: 25
<212> TYPE: DNA
<213> ORGANISM: Artificial Sequence
<220> FEATURE:
<223> OTHER INFORMATION: RabG.PF primer

<400> SEQUENCE: 50
atagcttgta tgcttttat ttgat                                    25

<210> SEQ ID NO 51
<211> LENGTH: 25
<212> TYPE: DNA
<213> ORGANISM: Artificial Sequence
<220> FEATURE:
<223> OTHER INFORMATION: RabG.PR primer

<400> SEQUENCE: 51
gaacagcagg gcctggggca ccatg                                   25

<210> SEQ ID NO 52
<211> LENGTH: 20
<212> TYPE: DNA
<213> ORGANISM: Artificial Sequence
<220> FEATURE:
<223> OTHER INFORMATION: RabG.1F primer

<400> SEQUENCE: 52
gtgaaaacca ccaaggagtc                                         20

<210> SEQ ID NO 53
<211> LENGTH: 20
<212> TYPE: DNA
<213> ORGANISM: Artificial Sequence
<220> FEATURE:
<223> OTHER INFORMATION: RabG.1R primer

<400> SEQUENCE: 53
ttctgttcac cctccggcag                                         20

<210> SEQ ID NO 54
<211> LENGTH: 25
<212> TYPE: DNA
<213> ORGANISM: Artificial Sequence
<220> FEATURE:
<223> OTHER INFORMATION: RabG.2R primer

<400> SEQUENCE: 54
tggtgaagat gtcgcagctc atgcc                                   25

<210> SEQ ID NO 55
<211> LENGTH: 20
<212> TYPE: DNA
<213> ORGANISM: Artificial Sequence
<220> FEATURE:
<223> OTHER INFORMATION: RabG.2F primer

<400> SEQUENCE: 55
accaccaaga gcgtgtcctt                                         20

<210> SEQ ID NO 56
<211> LENGTH: 22
<212> TYPE: DNA
<213> ORGANISM: Artificial Sequence
<220> FEATURE:
<223> OTHER INFORMATION: RabG.3F primer

<400> SEQUENCE: 56
ttcctgatga cctgctgccg ga                                      22

<210> SEQ ID NO 57
<211> LENGTH: 20
<212> TYPE: DNA
<213> ORGANISM: Artificial Sequence
<220> FEATURE:
<223> OTHER INFORMATION: C6R.1F primer

<400> SEQUENCE: 57
gttctaaagt tctttcctcc                                               20

<210> SEQ ID NO 58
<211> LENGTH: 23
<212> TYPE: DNA
<213> ORGANISM: Artificial Sequence
<220> FEATURE:
<223> OTHER INFORMATION: C6R.2F primer

<400> SEQUENCE: 58
tctttcatat cttgtagata aga                                           23

<210> SEQ ID NO 59
<211> LENGTH: 20
<212> TYPE: DNA
<213> ORGANISM: Artificial Sequence
<220> FEATURE:
<223> OTHER INFORMATION: C6R.3F primer

<400> SEQUENCE: 59
tgaaggggtt gatggaataa                                               20

<210> SEQ ID NO 60
<211> LENGTH: 25
<212> TYPE: DNA
<213> ORGANISM: Artificial Sequence
<220> FEATURE:
<223> OTHER INFORMATION: C6L.1R primer

<400> SEQUENCE: 60
ctatcaaaag tcttaatgag ttagg                                         25

<210> SEQ ID NO 61
<211> LENGTH: 25
<212> TYPE: DNA
<213> ORGANISM: Artificial Sequence
<220> FEATURE:
<223> OTHER INFORMATION: OX40L.1F primer

<400> SEQUENCE: 61
atggaaggag tacaaccatt agatc                                         25

<210> SEQ ID NO 62
<211> LENGTH: 25
<212> TYPE: DNA
<213> ORGANISM: Artificial Sequence
<220> FEATURE:
<223> OTHER INFORMATION: C5R.1R primer

<400> SEQUENCE: 62
ttaataagca caaatccac cagga                                          25

<210> SEQ ID NO 63
<211> LENGTH: 183
<212> TYPE: PRT
<213> ORGANISM: Felis catus

<400> SEQUENCE: 63

```
Met Glu Gly Val Gln Pro Leu Asp Glu Asn Val Gly Asn Ala Pro Gly
1               5                   10                  15

Arg Arg Phe Gln Ser Asn Lys Leu Leu Leu Val Thr Ala Val Ile Gln
            20                  25                  30

Gly Leu Gly Leu Leu Cys Phe Thr Tyr Ile Cys Leu His Phe Tyr
        35                  40                  45

Ala Ser Gln Val Pro Pro Gln Tyr Pro Pro Ile Gln Ser Ile Lys Val
    50                  55                  60

Gln Phe Thr Lys Cys Gly Asn Gly Thr Gly Cys Ile Ile Thr Ser Pro
65                  70                  75                  80

Asn Lys Asp Glu Thr Met Lys Val Gln Asp Asn Ser Ile Ile Ile Asn
                85                  90                  95

Cys Asp Gly Phe Tyr Leu Ile Ser Leu Lys Gly Tyr Phe Ser Glu Glu
                100                 105                 110

Leu Ser Leu Ser Leu Tyr Tyr Arg Lys Gly Arg Lys Pro Leu Phe Ser
            115                 120                 125

Leu Ser Lys Val Lys Ser Val Asp Ser Ile Gly Val Ala His Leu Ala
        130                 135                 140

Phe Lys Asp Lys Val Tyr Phe Asn Val Thr Thr His Asn Thr Ser Tyr
145                 150                 155                 160

Lys Asp Ile Gln Val Asn Gly Gly Glu Leu Ile Val Ile Leu Gln Asn
                165                 170                 175

Pro Gly Gly Phe Cys Val Leu
                180

<210> SEQ ID NO 64
<211> LENGTH: 183
<212> TYPE: PRT
<213> ORGANISM: Equus caballus

<400> SEQUENCE: 64

Met Glu Gly Val Gln Pro Leu Glu Glu Asn Val Gly Asn Thr Pro Gly
1               5                   10                  15

Arg Arg Phe Gln Arg Asn Lys Leu Leu Leu Val Thr Ser Ile Ile Gln
            20                  25                  30

Gly Leu Gly Leu Leu Cys Leu Thr Tyr Val Cys Leu His Phe Tyr
        35                  40                  45

Thr Ser Gln Val Pro Ser Gln Tyr Pro Pro Ile Gln Ser Ile Arg Val
    50                  55                  60

Gln Phe Thr Ser Cys Glu Asn Glu Lys Gly Phe Ile Ile Thr Ser Pro
65                  70                  75                  80

Asn Gln Asp Glu Ile Met Lys Val Gln Asp Asn Ser Ile Ile Ile Asn
                85                  90                  95

Cys Asp Gly Phe Tyr Leu Ile Ser Leu Lys Gly Tyr Phe Ser Gln Glu
                100                 105                 110

Leu Ser Leu Ser Leu His Tyr Arg Lys Gly Arg Glu Pro Leu Ser Ser
            115                 120                 125

Leu Ser Lys Val Arg Ser Val Asn Ser Ile Met Val Ala Tyr Leu Ala
        130                 135                 140

Phe Lys Asp Lys Val Tyr Leu Asn Val Thr Thr His Asn Thr Ser Cys
145                 150                 155                 160

Asp Asp Ile Gln Val Asn Gly Gly Glu Leu Ile Leu Ile His Gln Asn
                165                 170                 175

Pro Gly Gly Phe Cys Ala Tyr
```

180

<210> SEQ ID NO 65
<211> LENGTH: 182
<212> TYPE: PRT
<213> ORGANISM: Bos taurus

<400> SEQUENCE: 65

Met Glu Gly Val Gln Pro Leu Asp Glu Asn Val Gly Asn Val Pro Gly
1               5                   10                  15

Arg Arg Phe Leu Arg Asn Lys Leu Leu Leu Val Ala Ser Ile Ile Gln
                20                  25                  30

Gly Leu Gly Leu Leu Cys Leu Thr Tyr Ile Cys Leu His Phe Tyr
            35                  40                  45

Ala Gln Val Pro Ser Gln Tyr Pro Pro Ile Gln Ser Ile Arg Val Gln
        50                  55                  60

Phe Thr Lys Cys Glu Asn Glu Asn Gly Phe Ile Ile Thr Ser Pro Asp
65                  70                  75                  80

Ala Asp Gly Thr Met Lys Val Gln Asn Asn Ser Ile Ile Thr Cys
                85                  90                  95

Asp Gly Phe Tyr Leu Ile Ser Leu Lys Gly Tyr Phe Ser Gln Glu Leu
            100                 105                 110

Ser Leu Arg Leu Leu Tyr Arg Lys Gly Arg Glu Pro Leu Phe Ser Leu
        115                 120                 125

Asn Met Val Lys Ile Val Asp Ser Val Thr Val Ala Tyr Leu Arg Phe
130                 135                 140

Lys Asp Lys Val Tyr Leu Asn Met Thr Thr Gln Asn Ala Ser Cys Glu
145                 150                 155                 160

Asp Ile Gln Val Asn Gly Gly Glu Leu Ile Leu Ile His Gln Asn Pro
                165                 170                 175

Gly Gly Phe Cys Val Tyr
            180

<210> SEQ ID NO 66
<211> LENGTH: 182
<212> TYPE: PRT
<213> ORGANISM: sus scrofa

<400> SEQUENCE: 66

Met Glu Gly Val Gln Pro Leu Asp Glu Asn Val Gly Asn Ala Pro Gly
1               5                   10                  15

Arg Arg Leu Leu Arg Asn Lys Leu Leu Leu Val Ala Ser Val Ile Gln
                20                  25                  30

Gly Leu Gly Leu Leu Cys Leu Thr Tyr Ile Cys Leu His Leu Tyr
            35                  40                  45

Ala Gln Val Pro Ser Gln Tyr Pro Pro Ile Gln Ser Ile Lys Val Gln
        50                  55                  60

Phe Thr Lys Cys Glu Asn Asp Asn Gly Phe Ile Ile Thr Pro Ser Ser
65                  70                  75                  80

Lys Asp Gly Thr Met Lys Val Gln Asn Asn Ser Ile Ile Ile Asn Cys
                85                  90                  95

Asp Gly Phe Tyr Leu Ile Ser Leu Lys Gly Tyr Phe Ser Gln Glu Leu
            100                 105                 110

Ser Leu Met Leu Gln Tyr Arg Lys Gly Arg Lys Pro Leu Phe Ser Leu
        115                 120                 125

Asn Lys Val Lys Ser Val Asp Ser Val Thr Val Ala Asp Leu Ala Phe

```
                    130                 135                 140
Lys Asp Lys Val Phe Leu Asn Val Thr Thr His Ser Ala Ser Cys Glu
145                 150                 155                 160

Asp Ile Gln Val Asn Gly Gly Glu Leu Ile Leu Ile His Gln Asn Pro
                165                 170                 175

Gly Gly Phe Cys Val Tyr
            180

<210> SEQ ID NO 67
<211> LENGTH: 183
<212> TYPE: PRT
<213> ORGANISM: pan troglodytes

<400> SEQUENCE: 67

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Val Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 68
<211> LENGTH: 5049
<212> TYPE: DNA
<213> ORGANISM: Artificial Sequence
<220> FEATURE:
<223> OTHER INFORMATION: Plasmid p397-cOX40L (pC6 42Kp cOX40L)

<400> SEQUENCE: 68
ggaaattgta acgttaata ttttgttaaa attcgcgtta aattttgtt aaatcagctc      60 attttttaac caataggccg aaatcggcaa atcccttat aaatcaaaag aatagaccga    120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta atcggaacc ctaaagggag    300 cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
```

```
cacacccgcc gcgcttaatg cgccgctaca gggcgcgtcg cgccattcgc cattcaggct    480
gcgcaactgt tgggaagggc gatcggtgcg ggcctcttcg ctattacgcc agctggcgaa    540 aggggatgt gctgcaaggc gattaagttg ggtaacgcca gggttttccc agtcacgacg    600
ttgtaaaacg acggccagtg aattgtaata cgactcacta gggcgaat tgggtacctt     660 cataaataca agtttgatta aacttaagtt gttctaaagt tctttcctcc gaaggtatag    720
aacaaagtat ttcttctaca tccttactat ttattgcagc ttttaacagc ctatcacgta    780
tcctattttt agtattggta gaacgtttta gttctaaagt taaaatatta gacataattg    840
gcatattgct tattccttgc atagttgagt ctgtagatcg tttcagtata tcactgatta    900
atgtactact gttatgatga aatatagaat cgatattggc atttaactgt tttgttatac    960
taagtctaga ttttaaatct tctagtaata tgctatttaa tataaaagct tccacgtttt   1020
tgtatacatt tctttccata ttagtagcta ctactaaatg attatcttct ttcatatctt   1080
gtagataaga tagactatct ttatctttat tagtagaaaa tacttctggc catacatcgt   1140 taaattttt tgttgttgtt agatataata ttaaatatct agaggatcct attatttgtg    1200
gtaaaatgtt tatagagtaa aatgatctgg ctattaaaca taggccagtt accatagaat   1260
gctgcttccc gttacagtgt tttaccataa ccatagatct gcctgtattg ttgatacata   1320
taacagctgt aaatcctaaa aaattcctat cataattatt aatattaggt aattcatttc   1380
catgtgaaag atagactaat tttatatcct ttacctccaa ataattattt acatctctta   1440
aacaatctat tttaatatca ttaactggta ttttataata tccagaaagg tttgaagggg   1500
ttgatggaat aagtctatta acatcgttaa gtaaattatt aatatcatga atctttatta   1560
tattataccc ataagttaaa tttatattta ctttctcatc atctgactta gttagtttgt   1620
aataaggtgt gtctgaaaaa attaaaaggt aattcgttga atgaagctgt atttgctgta   1680
tcatttttat ctaattttgg agatttagca gtacttactt cattagaaga agaatctgcc   1740
agttcctgtc tattactgat atttcgtttc attattatat gatttatatt ttacttttttc   1800 aattatatat actcatttga ctagttaatc aataaaaaga attctcaaaa ttgaaaatat   1860
ataattacaa tataaaatgg aaggagtaca accattagat caaaatgttg gaaatacacc   1920
aggaagaaga tttcaaaaaa ataaagtatt attagtagca gcaataattc aaggtttagg   1980
attattatta tgttttacat atatatgttt acacttttat gcatctcaag taccacctca   2040
atatccacct atacaaagta taagagttca gtttacaaga tgtgaaaatg aaaaaggttg   2100
tattattaca tctccaagta aagatgaaac tatgaaagta caagataatt caataatcat   2160
aaattgtgat ggttttttact taattagttt aaaaggatat ttttcagaag aattatcatt   2220
atctttatat tatagaaaag gtagaggacc tttattttct ttatcaaaag taacatcagt   2280
tgattctatt ggagttgcat atttggcttt taaagataaa gtatattta atgttacaac   2340 tcattctact agttataaag atatacaagt aaatggtggt gaattaatat taatacatca   2400
aaatcctggt ggattttgtg cttattaatt tttatcccgg gttttatag ctaattagtc    2460 attttttcgta agtaagtatt tttatttaat acttttttatt gtacttatgt taaatataac   2520
tgatgataac aaaatccatt atgtattatt tataactgta atttctttag cgtagttaga   2580
tgtccaatct ctctcaaata catcggctat cttttttagtg agattttgat ctatgcagtt   2640
gaaacttatg aacgcgtgat gattaaaatg tgaaccgtcc aaatttgcag tcattatatg   2700
agcgtatcta ttatctacta tcatcatctt tgagttatta atatcatcta ctttagaatt   2760
gataggaaat atgaatacct ttgtagtaat atctatacta tctacaccta actcattaag   2820
```

```
acttttgata ggcggccgcg agctccagct tttgttccct ttagtgaggg ttaattccga    2880
gcttggcgta atcatggtca tagctgtttc ctgtgtgaaa ttgttatccg ctcacaattc    2940
cacacaacat acgagccgga agcataaagt gtaaagcctg gggtgcctaa tgagtgagct    3000
aactcacatt aattgcgttg cgctcactgc ccgctttcca gtcgggaaac ctgtcgtgcc    3060
agctgcatta atgaatcggc caacgcgcgg ggagaggcgg tttgcgtatt gggcgctctt    3120
ccgcttcctc gctcactgac tcgctgcgct cggtcgttcg gctgcggcga gcggtatcag    3180
ctcactcaaa ggcggtaata cggttatcca cagaatcagg ggataacgca ggaaagaaca    3240
tgtgagcaaa aggccagcaa aaggccagga accgtaaaaa ggccgcgttg ctggcgtttt    3300
tccataggct ccgcccccct gacgagcatc acaaaaatcg acgctcaagt cagaggtggc    3360
gaaacccgac aggactataa agataccagg cgtttccccc tggaagctcc ctcgtgcgct    3420
ctcctgttcc gaccctgccg cttaccggat acctgtccgc ctttctccct cgggaagcg    3480 tggcgctttc tcatagctca cgctgtaggt atctcagttc ggtgtaggtc gttcgctcca    3540
agctgggctg tgtgcacgaa ccccccgttc agcccgaccg ctgcgcctta tccggtaact    3600
atcgtcttga gtccaacccg gtaagacacg acttatcgcc actggcagca gccactggta    3660
acaggattag cagagcgagg tatgtaggcg gtgctacaga gttcttgaag tggtggccta    3720
actacggcta cactagaagg acagtatttg gtatctgcgc tctgctgaag ccagttacct    3780
tcggaaaaag agttggtagc tcttgatccg gcaaacaaac caccgctggt agcggtggtt    3840
tttttgtttg caagcagcag attacgcgca gaaaaaaagg atctcaagaa gatcctttga    3900
tcttttctac ggggtctgac gctcagtgga acgaaaactc acgttaaggg attttggtca    3960
tgagattatc aaaaaggatc ttcacctaga tccttttaaa ttaaaaatga agttttaaat    4020
caatctaaag tatatatgag taaacttggt ctgacagtta ccaatgctta atcagtgagg    4080
cacctatctc agcgatctgt ctatttcgtt catccatagt tgcctgactc cccgtcgtgt    4140
agataactac gatacgggag ggcttaccat ctggccccag tgctgcaatg ataccgcgag    4200
acccacgctc accggctcca gatttatcag caataaacca gccagccgga agggccgagc    4260
gcagaagtgg tcctgcaact ttatccgcct ccatccagtc tattaattgt tgccgggaag    4320
ctagagtaag tagttcgcca gttaatagtt tgcgcaacgt tgttgccatt gctacaggca    4380
tcgtggtgtc acgctcgtcg tttggtatgg cttcattcag ctccggttcc caacgatcaa    4440
ggcgagttac atgatccccc atgttgtgca aaaaagcggt tagctccttc ggtcctccga    4500
tcgttgtcag aagtaagttg gccgcagtgt tatcactcat ggttatggca gcactgcata    4560
attctcttac tgtcatgcca tccgtaagat gcttttctgt gactggtgag tactcaacca    4620
agtcattctg agaatagtgt atgcggcgac cgagttgctc ttgcccggcg tcaatacggg    4680
ataataccgc gccacatagc agaactttaa aagtgctcat cattggaaaa cgttcttcgg    4740
ggcgaaaact ctcaaggatc ttaccgctgt tgagatccag ttcgatgtaa cccactcgtg    4800
cacccaactg atcttcagca tcttttactt tcaccagcgt ttctgggtga gcaaaaacag    4860
gaaggcaaaa tgccgcaaaa aagggaataa gggcgacacg gaaatgttga atactcatac    4920
tcttcctttt tcaatattat tgaagcattt atcagggtta ttgtctcatg agcggataca    4980
tatttgaatg tatttagaaa aataaacaaa taggggttcc gcgcacattt ccccgaaaag    5040
tgccacctg                                                            5049
```

<210> SEQ ID NO 69

<211> LENGTH: 7865
<212> TYPE: DNA
<213> ORGANISM: Artificial Sequence
<220> FEATURE:
<223> OTHER INFORMATION: Plasmid p397-Syn Rabies G (pC3 I3Lp Syn Rabies G)

<400> SEQUENCE: 69

| | | | | | |
|---|---|---|---|---|---|
| agcttggcgt | aatcatggtc | atagctgttt | cctgtgtgaa | attgttatcc | gctcacaatt | 60 |
| ccacacaaca | tacgagccgg | aagcataaag | tgtaaagcct | ggggtgccta | atgagtgagc | 120 |
| taactcacat | taattgcgtt | gcgctcactg | cccgctttcc | agtcgggaaa | cctgtcgtgc | 180 |
| cagctgcatt | aatgaatcgg | ccaacgcgcg | gggagaggcg | gtttgcgtat | tgggcgctct | 240 |
| tccgcttcct | cgctcactga | ctcgctgcgc | tcggtcgttc | ggctgcggcg | agcggtatca | 300 |
| gctcactcaa | aggcggtaat | acggttatcc | acagaatcag | gggataacgc | aggaaagaac | 360 |
| atgtgagcaa | aaggccagca | aaaggccagg | aaccgtaaaa | aggccgcgtt | gctggcgttt | 420 |
| ttccataggc | tccgcccccc | tgacgagcat | cacaaaaatc | gacgctcaag | tcagaggtgg | 480 |
| cgaaacccga | caggactata | aagataccag | gcgtttcccc | ctggaagctc | cctcgtgcgc | 540 |
| tctcctgttc | cgaccctgcc | gcttaccgga | tacctgtccg | cctttctccc | ttcgggaagc | 600 |
| gtggcgcttt | ctcatagctc | acgctgtagg | tatctcagtt | cggtgtaggt | cgttcgctcc | 660 |
| aagctgggct | gtgtgcacga | accccccgtt | cagcccgacc | gctgcgcctt | atccggtaac | 720 |
| tatcgtcttg | agtccaaccc | ggtaagacac | gacttatcgc | cactggcagc | agccactggt | 780 |
| aacaggatta | gcagagcgag | gtatgtaggc | ggtgctacag | agttcttgaa | gtggtggcct | 840 |
| aactacggct | acactagaag | gacagtattt | ggtatctgcg | ctctgctgaa | gccagttacc | 900 |
| ttcggaaaaa | gagttggtag | ctcttgatcc | ggcaaacaaa | ccaccgctgg | tagcggtggt | 960 |
| ttttttgttt | gcaagcagca | gattacgcgc | agaaaaaaag | gatctcaaga | agatcctttg | 1020 |
| atcttttcta | cggggtctga | cgctcagtgg | aacgaaaact | cacgttaagg | gattttggtc | 1080 |
| atgagattat | caaaaaggat | cttcacctag | atccttttaa | attaaaaatg | aagttttaaa | 1140 |
| tcaatctaaa | gtatatatga | gtaaacttgg | tctgacagtt | accaatgctt | aatcagtgag | 1200 |
| gcacctatct | cagcgatctg | tctatttcgt | tcatccatag | ttgcctgact | ccccgtcgtg | 1260 |
| tagataacta | cgatacggga | gggcttacca | tctggcccca | gtgctgcaat | gataccgcga | 1320 |
| gacccacgct | caccggctcc | agatttatca | gcaataaacc | agccagccgg | aagggccgag | 1380 |
| cgcagaagtg | gtcctgcaac | tttatccgcc | tccatccagt | ctattaattg | ttgccgggaa | 1440 |
| gctagagtaa | gtagttcgcc | agttaatagt | ttgcgcaacg | ttgttgccat | tgctacaggc | 1500 |
| atcgtggtgt | cacgctcgtc | gtttggtatg | gcttcattca | gctccggttc | ccaacgatca | 1560 |
| aggcgagtta | catgatcccc | catgttgtgc | aaaaaagcgg | ttagctcctt | cggtcctccg | 1620 |
| atcgttgtca | gaagtaagtt | ggccgcagtg | ttatcactca | tggttatggc | agcactgcat | 1680 |
| aattctctta | ctgtcatgcc | atccgtaaga | tgcttttctg | tgactggtga | gtactcaacc | 1740 |
| aagtcattct | gagaatagtg | tatgcggcga | ccgagttgct | cttgcccggc | gtcaatacgg | 1800 |
| gataataccg | cgccacatag | cagaacttta | aaagtgctca | tcattggaaa | acgttcttcg | 1860 |
| gggcgaaaac | tctcaaggat | cttaccgctg | ttgagatcca | gttcgatgta | acccactcgt | 1920 |
| gcacccaact | gatcttcagc | atcttttact | ttcaccagcg | tttctgggtg | agcaaaaaca | 1980 |
| ggaaggcaaa | atgccgcaaa | aaagggaata | agggcgacac | ggaaatgttg | aatactcata | 2040 |
| ctcttccttt | ttcaatatta | ttgaagcatt | tatcagggtt | attgtctcat | gagcggatac | 2100 |

```
atatttgaat gtatttagaa aaataaacaa atagggttc  cgcgcacatt tccccgaaaa    2160
gtgccacctg acgtctaaga aaccattatt atcatgacat taacctataa aaataggcgt    2220
atcacgaggc cctttcgtct cgcgcgtttc ggtgatgacg gtgaaaacct ctgacacatg    2280
cagctcccgg agacggtcac agcttgtctg taagcggatg ccgggagcag acaagcccgt    2340
cagggcgcgt cagcgggtgt tggcgggtgt cggggctggc ttaactatgc ggcatcagag    2400
cagattgtac tgagagtgca ccatatgcgg tgtgaaatac cgcacagatg cgtaaggaga    2460
aaataccgca tcaggcgcca ttcgccattc aggctgcgca actgttggga agggcgatcg    2520
gtgcgggcct cttcgctatt acgccagctg gcgaaagggg gatgtgctgc aaggcgatta    2580
agttgggtaa cgccagggtt ttcccagtca cgacgttgta aaacgacggc cagtgaatta    2640
attcgagctc tttatactac tgggttacaa cagctggtga taacagaatg taaatcatta    2700
ttacttaata gttccattat tatatgtttg atatctatag gtaacctacc tattattcct    2760
agattcttac tctcttttac agctttaact attagctgat gtctatgaaa agctaatgat    2820
ttatttttcc gtattaattc cctatatata cgtatacatg caggtatctt attaactcta    2880
ggattagtta cgaactttac cataagatct atgttattgt caagaaagat attaaaagaa    2940
tatatagaat ttaactttat atgtgttata acatctagtt cttttttcgca tgattctttt    3000 atagatagta gtcttttatt actgtttata tgttccatgt ttactataaa accttctgaa    3060
ttagctattt caggattttt agatatttct aacatcattt tagatattat cataatagct    3120
atcttgtcat ctaaaaagct aacacaagtt agaggcgtat taccgtgatt atttagagaa    3180
ttatagtcgg cgttataaga taaaagtaat tttatattat taaaactatt agataacata    3240
gctttatgta aaggagtatt tccagataac ttagctttag catttacgta agcaccgtgg    3300
tcaagtaaga gtttaacaaa ttctgttttc atagaactaa ctgccatgta tagaggagtg    3360
aaacctttat gattatagac gtttacatag caaccatata ataagatcgc attcagtata    3420
ttaatatctt tcatttctat agctatgtga ataacatgtt tatctaatcc taccaacttt    3480
gtatcagtac cgtacttcag taataagttt actatagttt tgttttttaga tgcaacagct    3540 atatttagaa cggtatctat atgattatta accacattaa cattagatcc tctttctaaa    3600
agtgtctttg ttgtttcgat atcgttacgt gaaacagcgt aatgtaaggg actgcccata    3660
cagtcatcta ttacgtttat atcagctcct agatttaaca gaagtgctgt tacatctttt    3720
cttctattaa ttaccgaatg atgtaatggg gttttaccta aatcatcttg ttcgtttata    3780
ggcactccgt gatttataag taacgctatt atatcgtaac tacaattatt tttaagtgcc    3840
tttatgagat actgtttatg caaaaataaa cttttatcta ttttaatact attatctaac    3900
aatatcctaa ttaaatctat attcttatac tttatagcgt aatgtaacgg agtttcaaaa    3960
tttctagttt gtatattaag atcaatatta aaatctataa atattttata catatcatca    4020
gatatcttat catacagtac atcgtaataa tttagaaaga atctattaca attaacacct    4080
ttttttaata aatatctagt taatgactta ttgtttctat atacagaaat atataacgga    4140
ctatttccag aatgtatctg ttctatgtca gcgccagaat ctattagtag tttagcaatt    4200
tctgtattat ctaaactagc agctttatga agaggaggat ttttacattt taaaatatcg    4260
gcaccgtgtt ctagtaataa ttttaccatt tctatatcag aaatacttac ggctaaatac    4320
aaagacgttg atagtatatt tacgttattg tatttgcatt ttttaagtat ataccttact    4380
aaatttatat ctctataccct tatagcttta tgcagttcat ttataagtct tccattactc    4440
atttctggta atgaagtatt atatatcatt atgatattat ctctattta  ttctaataaa    4500
```

```
aaccgttatc atgttattta ttatttgtta taattatact atttaataaa ttataccaaa    4560
tacttagata cttattaata ccatcctaga acttgtattt cttgccccct aaacttggac    4620
atgcactcca ttaggcgttt cttgttttcg acatcgtcct ccttaacata tcctactgtt    4680
atgtgaggat tccacggatt atctactgtg atatcaccaa acacgtcctt cgaacagggt    4740
accgcattca gcagaacatt tcttagggct ctaagttcat cagatacctc cagtttcata    4800
actacagcgc atcctttcgc tcccaactgt ttagaggcgt tactctgagg aaaacacatc    4860
tcttctttac agactataga aatagtctgt aaatcttgat cagttatttg cttttttgaaa   4920 ttttcaaatc tatcacattg atccatattt gctattccaa gagttatatg aggaaaaata    4980
tcacatcctg tcatgtattt tattgtaaca ttattataat ctgtaacatc agtatctaac    5040
ctaacgtcgt aaaagttaac agatgcccag ttactataat cccaaggaac cttaacatct    5100
aatcccatta aaatagtatc ctttctacta ttttttttcat tggcaagtat gtggcttagt    5160
ttacacaaaa ttcctgccat tttgtaacga tagcgaagca atagcttgta tgcttttttat   5220 ttgattaact agtcataaaa atcgggatcc ctcgagatga gataaagtga aaatatatat    5280
cattatatta caaagtacaa ttatttaggt ttaatcatgg tgccccaggc cctgctgttc    5340
gtgcccctgc tggtgttccc cctgtgcttc ggcaagttcc ccatctacac catccccgac    5400
aagctgggcc cctggagccc catcgacatc caccacctga ctgccccaa caatctggtg     5460 gtggaggatg agggctgcac caatctgagc ggcttcagct acatggagct gaaagtgggc    5520
tacatcctgg ccatcaagat gaacggcttc acctgcaccg cgtggtgac cgaggccgag     5580 acctacacca actttgtggg ctacgtgacc accaccttca gcggaagca cttcagacct     5640 accccccgacg cctgcagagc cgcctacaac tggaagatgg ccggcgaccc tagatacgag   5700
gagagcctgc acaaccccta ccccgactac agatggctgc ggaccgtgaa aaccaccaag    5760
gagtccctgg tgatcatcag ccctagcgtg gccgatctgg accccctacga cagaagcctg   5820 cacagcagag tgttccctag cggcaagtgc agcggcgtgg ccgtgtccag cacctactgc    5880
agcaccaacc acgactacac catctggatg cccgagaacc ctagactggg catgagctgc    5940
gacatcttca ccaacagccg gggcaagaga ccagcaagg gcagcgagac ctgcggcttc     6000
gtggacgaga gaggcctgta caagagcctg aagggcgcct gcaagctgaa gctgtgcggc    6060
gtgctgggcc tgagactgat ggacggcacc tgggtggcca tgcagaccag caacgagacc    6120
aagtggtgcc ctcctgacca gctggtgaac ctgcacgact ccggagcga tgagatcgag     6180 cacctggtgg tggaagagct ggtgcggaag agagaggagt gcctgacgc cctggagagc     6240 atcatgacca ccaagagcgt gtccttccgg agactgagcc acctgagaaa gctggtgccc    6300
ggctttggca aggcctacac aatcttcaac aagaccctga tggaggccga tgcccactac    6360
aagtctgtgc ggacctggaa cgagatcctg cctagcaagg gctgcctgag agtgggcggc    6420
agatgccacc cccacgtgaa cggcgtgttc ttcaacggca tcatcctggg ccctgacggc    6480
aacgtgctga tccctgagat gcagagcagc ctgctgcagc agcacatgga actgctggag    6540
agcagcgtga tcccctggt gcacccctg gccgacccca gcaccgtgtt caaggatggc      6600
gacgaggccg aggacttcgt ggaggtgcac ctgcccgatg tgcacaacca ggtgtccggc    6660
gtggacctgg gcctgcccaa ctggggcaag tacgtgctgc tgagcgccgg agccctgacc    6720
gccctgatgt tgatcatctt cctgatgacc tgctgccgga gggtgaacag aagcgagccc    6780
acccagcaca acctgagagg caccggcaga gaggtgtccg tgacccccca gagcggcaag    6840
```

```
atcatcagca gctgggagag ccacaagagc ggcggagaga ccagactatg attttttatgc    6900
ccgggttttt atagctaatt agtcaaatgt gagttaatat tagtatacta cattactaat    6960
ttattacata ttcatttata tcaatctagt agcatttagc ttttataaaa caatataact    7020
gaatagtaca tactttacta ataagttata aataagagat acatatttat agtattttac    7080
tttctacact gaatataata ataataattat acaaatataa tttttaatac tatatagtat    7140
ataactgaaa taaatacca gtgtaatata gttattatac atttatacca catcaaagat    7200
gagttataac atcagtgtca ctgttagcaa cagtagttat acgatgagta gttactctcg    7260
tatggcgtta gtatgtatgt atcttctagt tttcttagta ggcattatag gaaacgtcaa    7320
gcttataagg ttattaatgg tatctagaaa tatatctatt ataccgtttc tcaacttggg    7380
aatagccgat ttgctgtttg tgatattcat acctttatac attatataca tactaagtaa    7440
tttccattgg cattttggta aagcactttg taaaattagt tctttctttt ttacttctaa    7500
catgttttgca agtatatttt taataactgt aataagcgta tatagatatg taaaaattac    7560
ccttcctgga tttacctata aatatgttaa cattagaaat atgtacatta ctatattttt    7620
catatggatt atttctatta tactagggat tcctgctctt tactttagaa atactatcgt    7680
aacaaaaaat aacgacacgc tgtgtattaa tcattatcat gataatagag aaattgctga    7740
attgatttac aaagttatta tctgtatcag atttattta ggatacctac tacctacgat    7800
aattatactc gtatgctata cgttactgat ctacagaact aacaatgcat gtcgacgcgg    7860
ccgca                                                                7865
```

<210> SEQ ID NO 70
<211> LENGTH: 235
<212> TYPE: PRT
<213> ORGANISM: Gallus gallus

<400> SEQUENCE: 70

```
Met Met Val Cys Ala Ser Ala Ser Thr Lys Gln Ala Arg Pro Ala Gly
1               5                   10                  15

Asp Cys Gly Pro Pro Val Leu Leu Val Pro Ala Leu Leu Val Glu Met
            20                  25                  30

Glu Gly Gln Pro Asp Thr Glu Leu Lys Lys His Thr Asp Gln Lys Asp
        35                  40                  45

Cys Glu Lys Glu Pro Ala Gly Met Arg Ser Asp Glu Trp Arg Gly
    50                  55                  60

Trp Gln Lys Gly Gln Ala Lys Arg Asn Thr Leu Tyr Leu Val Ser Ala
65                  70                  75                  80

Ala Thr Gln Trp Ile Leu Leu Ala Cys Leu Ile Tyr Leu Gly Thr
                85                  90                  95

Asp Ser Leu Gln Leu Trp Thr Pro His Ser Asp Lys Val Lys Trp Thr
            100                 105                 110

Tyr Ile Arg Tyr Thr Gly Gln Ser Ile Ala Gly Val Ala Met Asn Leu
        115                 120                 125

Ser Ala Glu Phe Thr Ser Ile Pro Val Ile Asn Gly Ser Ile Met Ile
    130                 135                 140

Pro Cys Asp Gly Leu Tyr Val Val Ser Leu Lys Gly Val Leu Ser Pro
145                 150                 155                 160

Asp Leu Glu Lys Ser Ser Leu Lys Leu Met Met Lys Asn Thr Glu Ser
                165                 170                 175

Lys Asn Ala Ala Pro Leu Trp Glu Arg Asp Val Gln Asn Ser Ser Asn
            180                 185                 190
```

```
Ala Val Asp Leu Ile Thr Met Leu Tyr Leu Phe Ala Gln Asn Asn Ile
        195                 200                 205

Ile Leu Ser Thr Ser Ser Asn Ala Thr Ile Gln Cys Leu Thr Phe Ser
        210                 215                 220

Leu Val Leu Leu Asn Pro Val Phe Cys Asn Pro
225                 230                 235

<210> SEQ ID NO 71
<211> LENGTH: 181
<212> TYPE: PRT
<213> ORGANISM: Ovis aries

<400> SEQUENCE: 71

Met Glu Gly Val Gln Pro Leu Asp Glu Asn Val Gly Asn Ala Pro Gly
1               5                   10                  15

Arg Arg Phe Leu Arg Asn Lys Leu Leu Val Ala Ser Ile Ile Gln
            20                  25                  30

Gly Leu Gly Leu Leu Cys Leu Thr Tyr Ile Cys Leu His Phe Tyr
        35                  40                  45

Ala Gln Val Pro Ser Gln Tyr Pro Pro Ile Gln Ser Ile Arg Val Arg
50                  55                  60

Phe Thr Cys Glu Asn Glu Asn Gly Phe Ile Ile Thr Ser Pro Asp Ala
65                  70                  75                  80

Asp Gly Thr Met Lys Val Gln Asn Asn Ser Ile Ile Ile Thr Cys Asp
                85                  90                  95

Gly Phe Tyr Leu Ile Ser Leu Lys Gly Tyr Phe Ser Gln Lys Leu Ser
            100                 105                 110

Leu Arg Leu Leu Tyr Arg Lys Gly Arg Glu Pro Leu Phe Ser Leu Asn
            115                 120                 125

Met Val Lys Ile Val Asp Ser Val Thr Val Ala Tyr Leu Arg Phe Lys
            130                 135                 140

Asp Lys Val Tyr Leu Asn Val Thr Thr Gln Asn Ala Ser Cys Glu Asp
145                 150                 155                 160

Ile Gln Val Asn Gly Gly Glu Leu Ile Leu Ile His Gln Asn Pro Gly
                165                 170                 175

Gly Phe Cys Val Tyr
            180
```

RECOMBINANT POXVIRAL VECTORS EXPRESSING BOTH RABIES AND OX40 PROTEINS, AND VACCINES MADE THEREFROM

CROSS-REFERENCE TO OTHER APPLICATIONS

This application is a continuation of, and claims benefit of, U.S. patent application Ser. No. 13/767,603, filed Aug. 12, 2015, which claims priority to U.S. provisional patent application 61/598,610, which was filed on Feb. 14, 2012, and is herein incorporated by reference in its entirety.

FIELD OF THE INVENTION

The present invention relates generally to viral vaccines and methods of using the same. More particularly, the present invention relates to viral vectors which may comprise one or more genetic adjuvants, resulting in enhanced immune response to an antigen expressed by a gene in a vector, advantageously a viral vector.

BACKGROUND

Rabies is a disease that can occur in all warm-blooded species and is caused by rabies virus. Infection with rabies virus followed by the outbreak of the clinical features in nearly all instances results in death of the infected species. Rabies virus is a non-segmented negative-stranded RNA virus of the Rhabdoviridae family. Rabies virus virions are composed of two major structural components: a nucleocapsid or ribonucleoprotein (RNP), and an envelope in the form of a bilayer membrane surrounding the RNP core. The infectious component of all Rhabdoviruses is the RNP core which consists of the RNA genome encapsidated by the nucleocapsid (N) protein in combination with two minor proteins, i.e. RNA-dependent RNA-polymerase (L) and phosphoprotein (P). The membrane surrounding the RNP core consists of two proteins: a trans-membrane glycoprotein (G) and a matrix (M) protein located at the inner site of the membrane.

The G protein, also referred to as spike protein, is responsible for cell attachment and membrane fusion in rabies virus and additionally is the main target for the host immune system. The amino acid region at position 330 to 340 (referred to as antigenic site III) of the G protein has been identified to be responsible for the virulence of the virus, in particular the Arg residue at position 333. All rabies virus strains have this virulence determining antigenic site III in common.

Conventional Rabies Vaccines for companion animals comprise inactivated rabies plus adjuvants, which are well-known in the art, are diverse in nature. Adjuvants may, for example, consist of water-insoluble inorganic salts, liposomes, micelles or emulsions, i.e. Freund's adjuvant. Other adjuvants may be found in Vogel and Powell, 1995, mentioned supra. Although there is no single mechanism of adjuvant action, an essential characteristic is their ability to significantly increase the immune response to a vaccine antigen as compared to the response induced by the vaccine antigen alone (Nossal, 1999, supra; Vogel and Powell, 1995, supra). In this regard, some adjuvants are more effective at augmenting humoral immune responses; other adjuvants are more effective at increasing cell-mediated immune responses (Vogel and Powell, 1995, supra); and yet another group of adjuvants increase both humoral and cell-mediated immune responses against vaccine antigens (Vogel and Powell, 1995, supra). In sum, adjuvants generally appear to exert their effects in at least one of five ways: 1) facilitate antigen uptake, transport and presentation in the lymph nodes, 2) prolong antigen presentation, 3) signal pathogen-recognition receptors (PRRs) expressed on innate immune cells, 4) cause damage or stress to cells, which signals an immune response, and 5) induce a preferential Th1 or Th2 response (Schijns V E et al. 2007). The immunogenicity of antigens may also be enhanced by the use of genetic adjuvants, such as ligands for receptor residing on immune cell membranes. Genetic adjuvants for DNA vaccines have been reviewed (see, e.g., Calarota & Weiner, Expert Rev Vaccines. 2004 August; 3(4 Suppl): S 135-49, Calarota & Weiner, Immunol Rev. 2004 June; 199:84-99 and Kutzler & Weiner, J Clin Invest. 2004 November; 1 14(9):1241-4), however genetic adjuvants for viral vaccines, especially for poxvirus-based viral vaccines, remain less well-studied.

Several members of tumor necrosis factor superfamily (TNFSF) and their corresponding receptors (TNFRSF) have been shown to provide critical costimulatory signals for immune response (Watts T H. Annu Rev Immunol 2005; 23:23-68). OX40 Ligand (OX40L), also known as gp34, CD252, CD134L or TNFSF4, is a member of the TNF superfamily. Human OX40L shares 46% amino acid sequence identity with its mouse counterpart. Similar to other TNF superfamily members, membrane-bound OX40 Ligand exists as a homotrimer. OX40L binds to OX40 (CD134), a member of the TNF receptor superfamily. OX40 is expressed on activated T cells, while its ligand, OX40L is induced on activated antigen-presenting cells (APCs), such as B cells, and dendritic cells (DCs) [Watts T H. 2005 supra, Sugamura K, et al., Nat Rev Immunol 2004; 4(6):420-31]. OX40-OX40L interaction can promote proliferation, differentiation, and especially survival of CD4+ T cells (Rogers P R, et al., Immunity 2001; 15(3):445-55; Song J, et al., Nat Immunol 2004; 5(2):150-8). Ligation of OX40 has been shown to enhance ex vivo human CD8+ T cell recall responses against viruses, including HIV-1, Epstein-Barr virus (EBV), and influenza virus (Serghides L, et al., J Immunol. 2005; 175(10):6368-77;). Co-immunization of mice with OX40L-expressing canarypox and HIV-1 canarypox vaccine, vCP1452, augmented HIV-1 specific CD8+ T cell responses in terms of frequency and cytokine expression (Liu J. et al., Vaccine. 2009; 275077-5084). However, OX40L did not enhance antibody responses elicited by the HIV-1 canarypox vaccine, suggesting that, canarypox vectors expressing OX40L can enhance the cellular but not humoral immunogenicity of HIV-1 canarypox vaccines. Liu J. et al., 2009, supra).

In the instant disclosure, the OX40L is co-expressed together with rabies G by the same recombinant as opposed to previous works by Serghides L, et al., 2005, supra, where adenovirus-expressed OX40L was used in combination with influenza peptides in an in vitro studies or the work described by Liu J. et al., 2009, where OX40L-expressing canarypox and HIV-1 expressing canarypox were co-administered. Surprisingly, this co-expression of OX40L resulted in 2- to 3-fold increase in peak anti-rabies neutralizing antibody titers as opposed to absence of improvement in humoral immunogenicity in the work reported by Liu J. et al., 2009, supra.

A genetically-adjuvanted Rabies vaccine for companion animals would be highly desirable, as it could avoid or reduce the negative consequences currently associated with conventional chemically adjuvanted vaccines (e.g. injection site reactions, discomfort, pain, non-specific immune responses, increased cancer risk etc.). For example, in cats, vaccine-associated sarcomas have been reported to develop in association with administration of some adjuvanted vaccines. Thus, there is a need for an effective and safe viral vaccine, especially with respect to expression of a target antigen, epitope, immunogen, peptide or polypeptide of interest in an amount sufficient to elicit a protective response.

SUMMARY OF THE INVENTION

An object of this invention can be any one or all of providing recombinant vectors or viruses as well as methods for making such viruses, and providing compositions and/or vaccines as well as methods for treatment and prophylaxis of infection.

The invention provides a recombinant vector, such as a recombinant virus, e.g., a recombinant poxvirus, that contains and expresses at least one exogenous nucleic acid molecule and, the at least one exogenous nucleic acid molecule may comprise a nucleic acid molecule encoding an immunogen or epitope of interest from Rabies, such as Rabies G.

The invention also encompasses the multitude of antigens that have been successfully expressed in vivo in an animal host, to elicit an immunological and/or protective immunological response, using a poxvirus or other suitable viral expression vector, including adenovirus, adeno-associated virus (AAV), paramyxovirus, Marek's disease virus (MDV), Newcastle disease virus, (NDV), infectious bursal disease virus (IBDV), infectious bronchitis virus (IBV), etc. Examples include, but are not limited to canine distemper virus, foot-and-mouth disease virus (FMDV, U.S. Pat. No. 7,527,960 to Merial), influenza (U.S. Pat. No. 7,384,642, U.S. Pat. No. 7,910,112, U.S. Pat. No. 6,713,068, and U.S. Pat. No. 7,507,416, each to Merial), bluetongue virus (BTV, U.S. Pat. No. 7,862,821 to Merial), porcine circovirus type II (PCV2, U.S. Pat. No. 6,497,883 to Merial), nipah virus (U.S. Pat. No. 7,803,612 to Merial), hendra virus, west nile virus (WNV, U.S. Pat. No. 7,740,863 to Merial), feline leukemia virus (FeLV, U.S. Pat. No. 7,582,302 to Merial), canine *leishmania* (U.S. Pat. No. 7,794,736 to Merial), feline calicivirus (FCV, U.S. Pat. No. 6,914,134 to Merial), feline infectious peritonitis virus (FIPV, U.S. Pat. No. 6,096,535 to Merial), feline immunodeficiency virus (FIV), African horse sickness virus (AHSV, US2010/0119546A1 to Merial) and vesicular stomatitis virus (U.S. Pat. No. 8,008,268 to Merial), the disclosure of each document herein incorporated by reference in its entirety.

In particular, the present invention provides a recombinant vector, such as a recombinant virus, e.g., a recombinant poxvirus, that contains and expresses at least one exogenous nucleic acid molecule and, the at least one exogenous nucleic acid molecule may comprise any suitable antigen, including Rabies G polypeptides and/or variants or fragments thereof.

The invention provides a recombinant vector, such as a recombinant poxvirus that contains a first polynucleotide encoding a Rabies G polypeptide and/or variant or fragment thereof and a second polynucleotide encoding a TNFα Receptor-binding polypeptide and/or variant or fragment thereof.

The invention further provides compositions or vaccine comprising such an expression vector or the expression product(s) of such an expression vector.

The invention further provides methods for inducing an immunological (or immunogenic) or protective response against Rabies, as well as methods for preventing or treating Rabies or disease state(s) caused by Rabies, comprising administering the expression vector or an expression product of the expression vector, or a composition comprising the expression vector, or a composition comprising an expression product of the expression vector.

The invention also relates to expression products from the virus as well as antibodies generated from the expression products or the expression thereof in vivo and uses for such products and antibodies, e.g., in diagnostic applications.

Kits comprising at least one Rabies polypeptide or fragment or variant thereof and instructions for use are also provided.

The invention is also based, in part, on the unexpected and surprising result that poxviral vectors co-expressing in vivo in an animal host genes encoding antigens from pathogens, including but not limited to rabies, and a TNFα R ligand genetic adjuvant, including but not limited to OX40L, can elicit in the animal a long-lasting protective immunity against rabies. In particular, the OX40L may be homologous to the species being vaccinated, for example, canine OX40L (cOX40L) may be effectively combined with rabies G in a canine vaccine against rabies.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIGS. 7A-7C provide the sequence of vCP3006 covering the flanking C3 arms, the I3L promoter as well as the synthetic rabies G (complete sequence is as set forth in SEQ ID NO:2);

FIG. 8 presents the predicted amino acid sequence of synthetic codon-optimized rabies virus glycoprotein G (SEQ ID NO:1);

FIG. 10 is a schematic representation of genomic organization of vCP3015, carrying classic Rabies virus G at the C5 site and cOX40L at the C6 site;

FIGS. 15A-15B is the sequence of vCP3015 covering the flanking C6 arms, the 42K promoter as well as the synthetic cOX40L (collectively as set forth in SEQ ID NO:7)

FIG. 16 is the predicted amino acid sequence of synthetic cOX40L (SEQ ID NO:12, 63, 64, 65, 66, OR 67);

FIGS. 18A-18B is the sequence of vCP3015 covering the flanking C5 arm, the H6 promoter as well as the classical rabies virus G (collectively as set forth in SEQ ID NO:13)

FIG. 19 is the predicted amino acid sequence of classical rabies virus G (SEQ ID NO:1). The predicted amino acid sequences of classical G and codon-optimized G (SEQ ID NO:1) are 100% identical;

FIG. 21 depicts separation of PmeI digested genomic DNA on gel electrophoresis and Southern blot hybridization using classical rabies virus G probe;

FIG. 22 depicts separation of BamHI digested genomic DNA on gel electrophoresis and Southern blot hybridization using synthetic rabies virus G probe.

FIG. 23 depicts separation of NruI digested genomic DNA on gel electrophoresis and Southern blot hybridization using classical rabies virus G probe;

FIG. 24 is a Western blot analysis of vCP3012. A band corresponding to rabies virus G was detectable in infected cell pellet;

FIG. 25 a schematic drawing of vCP3012 C6 region showing primer locations

FIG. 26 presents the sequence of vCP3012 covering the flanking C6 arms, the 42K promoter as well as the synthetic cOX40L (collectively as set forth in SEQ ID NO:17);

FIGS. 28A-28C present the sequence of vCP3012 covering the flanking C3 arms, the I3L promoter as well as the synthetic rabies G (collectively as set forth in SEQ ID NO:20);

FIG. 29 presents a schematic diagram of a fragment of vCP3012, from C5R to C5L (i.e. rabies virus G and flanking regions);

FIGS. 30A-30B present the sequence of vCP3012 from C5R to C5L encompassing the rabies G gene (collectively as set forth in SEQ ID NO:23). The predicted amino acids of classical rabies virus G (SEQ ID NO:1) and synthetic rabies virus G (SEQ ID NO:1) are 100% identical and are the same as described for vCP3006 or vCP3015;

FIG. 36 is a description of SEQ ID NOs:1-24, 63-67;

FIG. 37 is a description of SEQ ID NOs:25-62;

FIG. 38 presents an amino acid sequence alignment of SEQ ID NOs:12, 63-67 (i.e. selected OX40L peptides). The accompanying table indicates percent identity among the sequences.

DETAILED DESCRIPTION OF THE INVENTION

Figure 1:
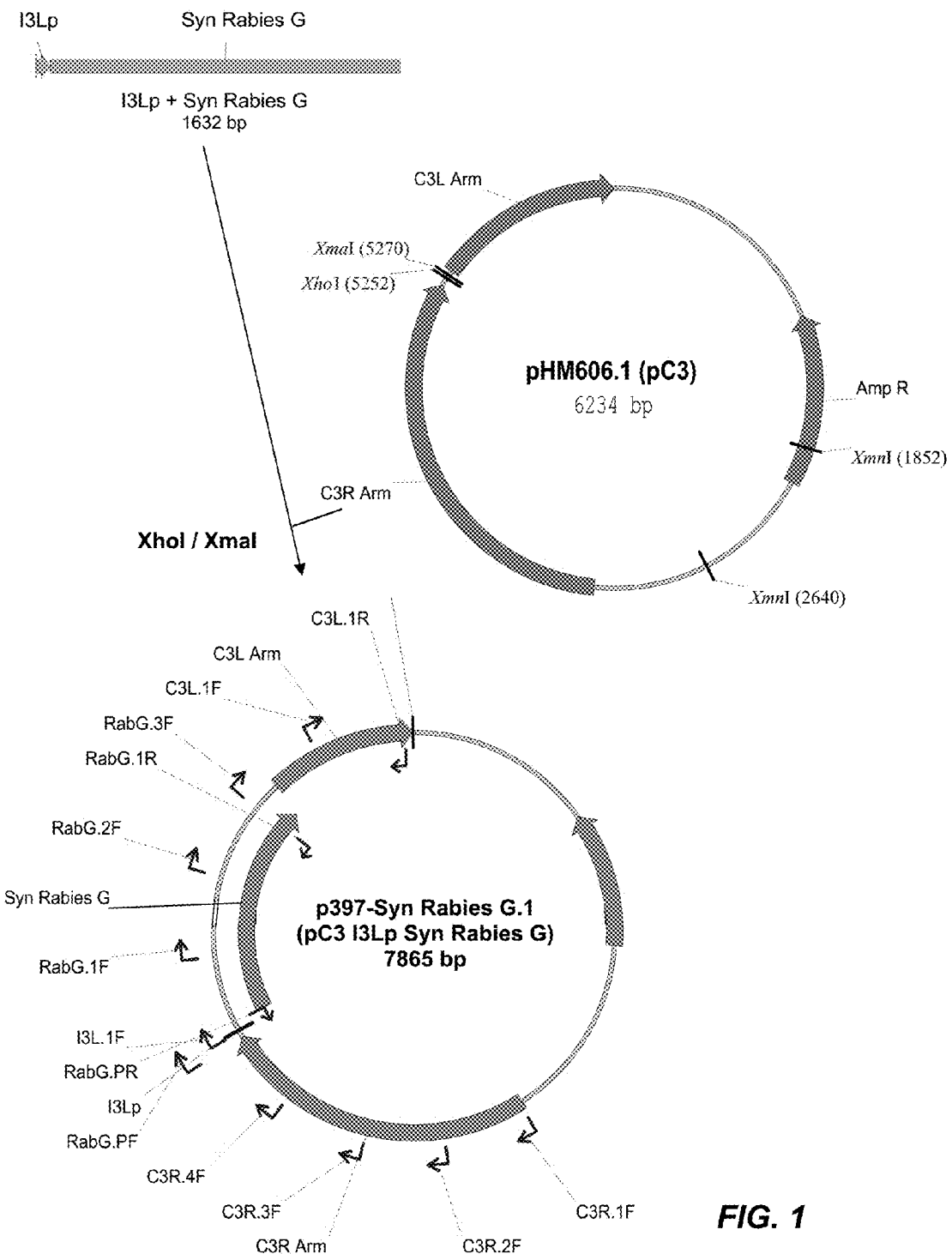
FIG. 1 provides a schematic for the Construction of donor plasmid p397-Syn Rabies G. Location of sequencing primers used to verify the sequence of the flanking C3 arms as well as the synthetic rabies G are shown.

Compositions comprising an expression vector comprising a polynucleotide encoding a Rabies polypeptide and fragments and variants thereof that elicit an immunogenic response in an animal are provided. The expression vector comprising the polynucleotide encoding Rabies polypeptide or fragments or variants may be formulated into vaccines or pharmaceutical compositions and used to elicit or stimulate a protective response in an animal. In one embodiment the Rabies polypeptide is a Rabies G polypeptide or active fragment or variant thereof.

Compositions comprising an expression vector comprising a polynucleotide encoding a Rabies G polypeptide or active fragments or variants thereof and a polynucleotide encoding an OX40L polypeptide or active fragments or variants thereof are provided. In particular, the OX40L is a canine OX40L (cOX40L).

It is recognized that the polypeptides of the invention may be full length polypeptides or active fragments or variants thereof. By "active fragments" or "active variants" is intended that the fragments or variants retain the antigenic nature of the polypeptide. Thus, the present invention encompasses any Rabies polypeptide, antigen, epitope or immunogen that elicits an immunogenic response in an animal. The Rabies polypeptide, antigen, epitope or immunogen may be any Rabies polypeptide, antigen, epitope or immunogen, such as, but not limited to, a protein, peptide or fragment or variant thereof, that elicits, induces or stimulates a response in an animal, such as an avian.

A particular Rabies polypeptide of interest is Rabies glycoprotein (G). Rabies G refers to a type of glycoprotein found on the surface of the Rabies virus. It is an antigenic glycoprotein and is responsible for binding the virus to the cell that is being infected. It is recognized that precursors of any of these antigens can be used.

The antigenic polypeptides of the invention are capable of protecting against Rabies. That is, they are capable of stimulating an immune response in an animal. By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "Rabies G polypeptide or polynucleotide" refers to any native or optimized Rabies G polypeptide or polynucleotide, and their derivatives and variants.

The term "OX40L polypeptide or polynucleotide" refers to any native or optimized OX40L polypeptide or polynucleotide, and their derivatives and variants.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Compositions

The present invention relates to a Rabies vaccine or composition which may comprise a recombinant or expression vector comprising a polynucleotide encoding a Rabies polypeptide, antigen, epitope or immunogen and a pharmaceutically or veterinarily acceptable carrier, excipient, or vehicle. The Rabies polypeptide, antigen, epitope or immunogen may be any Rabies polypeptide, antigen, epitope or immunogen, such as, but not limited to, a protein, peptide or fragment thereof, that elicits, induces or stimulates a response in an animal.

The present invention relates to a Rabies vaccine or composition which may comprise a recombinant or expression vector comprising a polynucleotide encoding a Rabies G polypeptide and a pharmaceutically or veterinarily acceptable carrier, excipient, or vehicle. In one embodiment, the expression vector may further comprise a polynucleotide encoding an OX40L polypeptide.

In another embodiment, the pharmaceutically or veterinarily acceptable carrier, excipient, or vehicle may be a water-in-oil emulsion. In yet another embodiment, the water-in-oil emulsion may be a water/oil/water (W/O/W) triple emulsion. In yet another embodiment, the pharmaceutically or veterinarily acceptable carrier, excipient, or vehicle may be an oil-in-water emulsion.

In an embodiment, the Rabies polypeptide, antigen or fragment or variant thereof comprises a Rabies G polypeptide or fragment or variant thereof. In an aspect of this embodiment, the Rabies G polypeptide or fragment or variant thereof is a recombinant polypeptide produced by a Rabies G gene. In another aspect of this embodiment, the Rabies G gene has at least 70% identity to the sequence as set forth in SEQ ID NO: 5 or 16. In another aspect of this embodiment, the Rabies G polypeptide or fragment or variant thereof has at least 80% identity to the sequence as set forth in SEQ ID NO:1.

In another embodiment, the OX40L polypeptide, antigen or fragment or variant is a recombinant polypeptide produced by an OX40L gene. In another aspect of this embodiment, the OX40L gene has at least 70% identity to the sequence as set forth in SEQ ID NO:10. In another aspect of this embodiment, the OX40L polypeptide or fragment or variant thereof has at least 80% identity to the sequence as set forth in SEQ ID NO:12, 63, 64, 65, 66, OR 67.

In another embodiment the present invention provides for a novel, genetically-adjuvanted rabies vaccine, for non-sole use in companion animals such as cats, dogs, and ferrets, which comprises a recombinant poxvirus vector, which contains and expresses Rabies G and OX40L. In another embodiment, the vector may comprise a recombinant canarypox. In another embodiment, the rabies surface glycoprotein gene may encode the rabies glycoprotein G, having the sequence as set forth in SEQ ID NO:1, and the OX40L has the sequence as set forth in SEQ ID NO:12, 63, 64, 65, 66, OR 67.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of a Rabies polypeptide. A polynucleotide encoding a fragment of a Rabies polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999; PCT/US2004/022605) can be used in the practice of the invention.

The term “nucleic acid” and “polynucleotide” refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term “gene” is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

As regards variations of the OX40L, a “functional fragment or variant of OX40L” is defined herein as a peptide that adjuvants/augments the immune response elicited by an immunogenic peptide via the same mechanism, and to a comparable extent, as compared to the OX40L of the present disclosure. For example, if a feline OX40L, when co-expressed with rabies G in a canine host results in an immune response against rabies that is greater than that elicited by a rabies G expression vector alone, and the feline OX40L is acting via the same mechanism (e.g. binding TNF receptor), then the feline OX40L would be considered to be a "functional fragment or variant" of the canine OX40L exemplified herein. Likewise, polymorphic versions of canine OX40L that are capable of augmenting an immune response are also "function fragments or variants" of cOX40L. Finally, if a truncated version of an OX40L adjuvants/augments an immune response to a comparable extent as the corresponding full-length OX40L, the truncated version is considered to be a "functional fragment or variant of OX40L".

The invention further comprises a complementary strand to a polynucleotide encoding a Rabies antigen, epitope or immunogen or to a polynucleotide encoding an OX40L antigen, epitope or immunogen. The complementary strand can be polymeric and of any length, and can contain deoxyribonucleotides, ribonucleotides, and analogs in any combination.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a partially purified polypeptide preparation is one in which the polypeptide is more enriched than the polypeptide is in its natural environment. That is the polypeptide is separated from cellular components. By "substantially purified" is intended that such that at least 60%, at least 70%, at least 80%, at least 90%, at least 95%, or at least 98%, or more of the cellular components or materials have been removed. Likewise, a polypeptide may be partially purified. By "partially purified" is intended that less than 60% of the cellular components or material is removed. The same applies to polynucleotides. The polypeptides disclosed herein can be purified by any of the means known in the art.

Moreover, homologs of Rabies G polypeptides and homologs of OX40L polypeptides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. For example, analogs, orthologs, and paralogs of a wild-type Rabies polypeptide can differ from the wild-type Rabies polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type Rabies polypeptide or polynucleotide sequences, and will exhibit a similar function.

In another aspect, the present invention provides a polypeptide having at least 70%, at least 75%, at least 80%, at least 85%, at least 90%, at least 95%, 96%, 97%, 98% or 99% sequence identity to a polypeptide having a sequence as set forth in SEQ ID NO:1. In yet another aspect, the present invention provides fragments and variants of the Rabies polypeptides or OX40L polypeptides identified above (SEQ ID NO:1 or 12, 63-67) which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO:1 or 12, 63-67.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the Rabies polypeptide or OX40L primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

An immunogenic fragment of a Rabies polypeptide or OX40L polypeptide includes at least 8, 10, 13, 14, 15, or 20 consecutive amino acids, at least 21 amino acids, at least 23 amino acids, at least 25 amino acids, or at least 30 amino acids of a Rabies G polypeptide having a sequence as set forth in SEQ ID NO:1, or variants thereof, or of an OX40L polypeptide having a sequence as set forth in SEQ ID NO:12, 63, 64, 65, 66, OR 67, or variants thereof.

In another aspect, the present invention provides a polynucleotide encoding a Rabies G polypeptide, such as a polynucleotide encoding a polypeptide having a sequence as set forth in SEQ ID NO:5 or 16. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO:1, or a conservative variant, an allelic variant, a homolog or an immunogenic fragment comprising at least eight or at least ten consecutive amino acids of one of these polypeptides, or a combination of these polypeptides.

In yet another aspect, the present invention provides a polynucleotide encoding an OX40L polypeptide, such as a polynucleotide encoding a polypeptide having a sequence as set forth in SEQ ID NO:12, 63, 64, 65, 66, OR 67. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO:12, 63, 64, 65, 66, OR 67, or a conservative variant, an allelic variant, a homolog or an immunogenic fragment comprising at least eight or at least ten consecutive amino acids of one of these polypeptides, or a combination of these polypeptides.

In another aspect, the present invention provides a polynucleotide having a nucleotide sequence as set forth in SEQ ID NO:5, 10, or 16, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO:5, 10, or 16, or a variant thereof.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for Rabies G polypeptides or OX40L polypeptides, the DNA sequence of the Rabies G gene or OX40L gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of Rabies G protein or OX40L protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the Rabies G polypeptide or the OX40L polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

Hybridization reactions can be performed under conditions of different "stringency." Conditions that increase stringency of a hybridization reaction are well known. See for example, "Molecular Cloning: A Laboratory Manual", second edition (Sambrook et al., 1989).

The invention further encompasses the Rabies polynucleotide or OX40L polynucleotide or both contained in a vector molecule or an expression vector and operably linked to a promoter element and optionally to an enhancer.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a Rabies G polypeptide, antigen, epitope or immunogen or an OX40L polypeptide are advantageously present in an inventive vector. In minimum manner, this comprises an initiation codon (ATG), a stop codon and a promoter, and optionally also a polyadenylation sequence for certain vectors such as plasmid and certain viral vectors, e.g., viral vectors other than poxviruses. When the polynucleotide encodes a polypeptide fragment, e.g. a Rabies G polypeptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to preparations comprising vectors, such as expression vectors, e.g., therapeutic compositions. The preparations can comprise one or more vectors, e.g., expression vectors, such as in vivo expression vectors, comprising and expressing one or more Rabies G or OX40L polypeptides, antigens, epitopes or immunogens. In one embodiment, the vector contains and expresses a polynucleotide that comprises a polynucleotide coding for and/or expressing a Rabies G antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of a Rabies G polypeptide, antigen, epitope or immunogen (e.g., hemagglutinin, neuraminidase, nucleoprotein) or a fragment thereof.

According to another embodiment, the vector or vectors in the preparation comprise, or consist essentially of, or consist of polynucleotide(s) encoding one or more proteins or fragment(s) of a Rabies G polypeptide, antigen, epitope or immunogen, or an OX40L polypeptide, antigen, epitope or immunogen, or a combination thereof. In another embodiment, the preparation comprises one, two, or more vectors comprising polynucleotides encoding and expressing, advantageously in vivo, a Rabies G polypeptide, antigen, fusion protein or an epitope thereof. The invention is also directed at mixtures of vectors that comprise polynucleotides encoding and expressing different a Rabies G polypeptides, antigens, epitopes, fusion protein, or immunogens, e.g., a Rabies G polypeptide, antigen, epitope or immunogen from different species such as, but not limited to, humans, pigs, cows or cattle, dogs, cats, and avian.

According to a yet further embodiment of the invention, the expression vector is a plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846, 946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding a Rabies G polypeptide, antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig.

In more general terms, the promoter has either a viral, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

As to the polyadenylation signal (polyA) for the plasmids and viral vectors other than poxviruses, use can be made of the poly(A) signal of the bovine growth hormone (bGH) gene (see U.S. Pat. No. 5,122,458), or the poly(A) signal of the rabbit (3-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Methods of Use and Article of Manufacture

The present invention includes the following method embodiments. In an embodiment, a method of vaccinating an animal comprising administering a composition comprising a vector comprising a polynucleotide encoding a Rabies G polypeptide or fragment or variant thereof and a pharmaceutical or veterinarily acceptable carrier, excipient, or vehicle to an animal is disclosed. In one aspect of this embodiment, the animal is an avian, an equine, a canine, a feline, a ferret, a seal, or a porcine.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

In the present invention a recombinant viral vector is used to express a Rabies coding sequence or fragments thereof encoding a Rabies polypeptide or fragment or variant thereof. Specifically, the viral vector can express a Rabies sequence, more specifically a Rabies G gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. No. 5,505,941, U.S. Pat. No. 5,494,807), raccoonpox virus, swinepox virus, etc.], adenovirus (e.g., human adenovirus, canine adenovirus), herpesvirus (e.g. canine herpesvirus, feline herpesvirus, bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The Rabies polypeptide, antigen, epitope or immunogen may be a Rabies G. For example, the poxvirus vector comprising the Rabies G may be vectors as described in U.S. Pat. No. 5,756,102. The Rabies G polypeptide or antigen of the invention to be expressed is inserted under the control of a specific poxvirus promoter, e.g., the vaccinia promoter 7.5 kDa (Cochran et al., 1985), the vaccinia promoter I3L (Riviere et al., 1992), the vaccinia promoter G (Shida, 1986), the cowpox promoter ATI (Funahashi et al., 1988), the vaccinia promoter H6 (Taylor et al., 1988b; Guo et al., 1989; Perkus et al., 1989), inter alia.

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

In one aspect of the prime-boost protocol or regime of the invention, a prime-boost protocol may comprise the administration of a composition comprising a recombinant viral vector that contains and expresses a Rabies G polypeptide, antigen and/or variants or fragments thereof in vivo followed by the administration of a recombinant Rabies G polypeptide or antigen of the invention. Likewise, a prime-boost protocol may comprise the administration of a composition comprising a Rabies G antigen of the invention followed by the administration of a recombinant viral vector that contains and expresses a Rabies G polypeptide or antigen and/or variants or fragments thereof in vivo. It is further noted that both the primary and the secondary administrations may comprise the recombinant viral vector that contains and expresses a Rabies G polypeptide of the invention. Thus, the recombinant Rabies viral vector of the invention may be administered in any order with a recombinant Rabies antigen or alternatively may be used alone as both the primary and secondary compositions.

In another aspect of the prime-boost protocol of the invention, a composition comprising a recombinant viral vector that contains and expresses a Rabies G polypeptide, antigen and/or variants or fragments thereof in vivo of the invention is administered followed by the administration of an inactivated viral composition or vaccine comprising the Rabies polypeptide or antigen. Likewise, a prime-boost protocol may comprise the administration of an inactivated viral composition or vaccine followed by the administration of a recombinant viral vector that contains and expresses a Rabies G polypeptide, antigen and/or variants or fragments thereof in vivo of the invention.

In yet another aspect of the prime-boost protocol of the invention, the prime-boost protocol comprises at least one prime-administration of a recombinant viral vector-based composition of the invention and at least one boost-administration of a plasmid-based composition of the invention. Likewise, the primes-boost may comprise at least one prime-administration of at least one prime-administration of a plasmid-based composition of the invention and at least one boost-administration of a recombinant viral-vector based composition of the invention.

The dose volume of compositions for target species that are mammals, e.g., the dose volume of dog compositions, based on viral vectors, e.g., non-poxvirus-viral-vector-based compositions, is generally between about 0.1 to about 2.0 ml, between about 0.1 to about 1.0 ml, and between about 0.5 ml to about 1.0 ml.

The efficacy of the vaccines may be tested after the last immunization by challenging animals, such as dog, with a virulent strain of Rabies. In general, animals are anesthetized and 1.0 ml challenge material is administered via IM injection (0.5 ml into each frontalis and/or masseter muscle). The target dose is about 3.8 log $10LD_{50}$/ml, and a challenge back titration in mice is performed to verify the actual inoculated dose. Seven days prior to challenge dogs are acclimated to individual cages and maintained in individual cages until the end of the study. Animals are fed a commercially available diet and be provided with water ad libitum. SAS® software V9.1 Enterprise Guide may be used for producing a randomization table for housing. On D0, the challenge strain may be prepared by diluting the initial challenge suspension stock 1:100 in PBS+2% fetal calf serum. The diluted challenge material may be placed in a sterile, sealed and capped vial, labeled accordingly and kept on ice until used. The morning before challenge, it is advisable to administer analgesic/antiinflammatory, for example, firocoxib 5 mg/kg (calculated dose in half tablet increments) if the animals are dogs. Animals should observed daily for at least 30 days post-challenge for mortality or for progressive neurological signs indicative of rabies infection. Animals with progressive neurological signs will be humanely euthanized according to accepted procedures. Core brain samples will be harvested immediately after death or euthanasia from all animals. Blood collection after challenge may be collected at time of euthanasia under anesthesia, via intracardiac stick. Blood may be processed for serum, divided into two aliquots (2-3 ml/each) and the serum stored frozen (~−20° C.) until testing. A core sample from the medulla oblongata may be collected from all animals that die or are euthanized during the post-challenge period and any surviving animals euthanized at study termination. Samples may be shipped fresh on ice or frozen on dry ice to the testing facility. Serum rabies antibody titer may be quantified using a Rapid Fluorescent Focus Inhibition Test (RFFIT) or a Fluorescent Antibody Virus Neutralization (FAVN) Assay, and brain tissue from the study animals may be subjected to direct immunofluorescent staining of anti-rabies monoclonal antibody.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetjet or Vitajet apparatus (Bioject, Oreg., USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment. In an advantageous embodiment, the animal is a dog, ferret or seal.

In one embodiment, the invention provides for the administration of a therapeutically effective amount of a formulation for the delivery and expression of a Rabies antigen or epitope in a target cell. Determination of the therapeutically effective amount is routine experimentation for one of ordinary skill in the art. In one embodiment, the formulation comprises an expression vector comprising a polynucleotide that expresses a Rabies antigen or epitope and a pharmaceutically or veterinarily acceptable carrier, vehicle or excipient. In another embodiment, the pharmaceutically or veterinarily acceptable carrier, vehicle or excipient facilitates transfection or infection and/or improves preservation of the vector or protein in a host.

Another embodiment of the invention is a kit for performing a method of eliciting or inducing an immunological or protective response against Rabies in an animal comprising a recombinant Rabies G immunological composition or vaccine and instructions for performing the method of delivery in an effective amount for eliciting an immune response in the animal.

In an embodiment, the subject matter disclosed herein is directed to a kit for performing a method of eliciting or inducing an immune response which may comprise any one of the recombinant Rabies compositions or vaccines, inactivated Rabies compositions or vaccines, recombinant Rabies viral compositions or vaccines, or plasmid-based Rabies compositions or vaccines, and instructions for performing the method, Another embodiment of the invention is a kit for performing a method of inducing an immunological or protective response against Rabies in an animal comprising a composition or vaccine comprising a Rabies polypeptide or antigen of the invention and a recombinant Rabies viral composition or vaccine, and instructions for performing the method of delivery in an effective amount for eliciting an immune response in the animal.

Another embodiment of the invention is a kit for performing a method of inducing an immunological or protective response against Rabies in an animal comprising a composition or vaccine comprising a recombinant Rabies viral vector of the invention and an inactivated Rabies immunological composition or vaccine, and instructions for performing the method of delivery in an effective amount for eliciting an immune response in the animal.

Another embodiment of the invention is a kit for performing a method of inducing an immunological or protective response against Rabies in an animal comprising a composition or vaccine comprising a recombinant Rabies viral vector of the invention and a plasmid-based Rabies composition or vaccine, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

In one embodiment, the invention provides for the administration of a therapeutically effective amount of a formulation for the delivery and expression of a Rabies G polypeptide or antigen or epitope in a target cell. Determination of the therapeutically effective amount is routine experimentation for one of ordinary skill in the art. In one embodiment, the formulation comprises an expression vector comprising a polynucleotide that expresses a Rabies G polypeptide or antigen or epitope and a pharmaceutically or veterinarily acceptable carrier, vehicle or excipient. In another embodiment, the pharmaceutically or veterinarily acceptable carrier, vehicle or excipient facilitates transfection or infection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

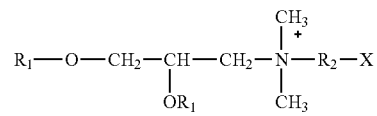

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

When DOPE is present, the DMRIE:DOPE molar ratio is advantageously about 95: about 5 to about 5: about 95, more advantageously about 1: about 1, e.g., 1:1.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are preferably formed by basic units having the following formula:

$$----C-(CH_2)_{\overline{x}}-C-(CH_2)_{\overline{y}}-$$
$$\begin{array}{cc} R_1 & R_2 \\ | & | \\ COOH & COOH \end{array}$$

in which:
R1 and R2, which can be the same or different, represent H or CH3
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

Other cytokines that may be used in the present invention include, but are not limited to, granulocyte colony stimulating factor (G-CSF), granulocyte/macrophage colony stimulating factor (GM-CSF), interferon α (IFNγ), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a canine cytokine for preparations to be administered to canine).

The invention will now be further described by way of the following non-limiting examples.

Example 1—Construction of Recombinant vCP3006, Expressing Four Copies of Rabies Virus Glycoprotein An ALVAC recombinant virus was produced in which a synthetic Rabies G gene has been inserted into the C3 loci (2 copies) in the background of vCP65a carrying a classic Rabies virus G in the C5 loci (2 copies).

Summary.

A synthetic codon-optimized Rabies virus G (SEQ ID NO:1) was inserted into the C3 loci of a parental canarypox virus (ALVAC CP65a [as fully described in U.S. Pat. No. 5,843,456, to Virogenetics], having a titer of 6.1×10E7 pfu/mL, resuspended in 1 mL Tris pH9 buffer). Parental ALVAC, which was used to produce the CP65a, was deposited on Nov. 14, 1996 under the terms of the Budapest Treaty with the ATCC, accession number VR-2547. Thus, a skilled person in the art is fully expected to be able to make and use the CP65a of U.S. Pat. No. 5,843,456, or a reasonable/functional substitute thereof. The protein sequence of the codon-optimized rabies virus G was 100% identical to GenBank ACR15154.1 (SEQ ID NO:1). The donor plasmid comprised synthetic Rabies G gene (SEQ ID NO:5) and I3L promoter (SEQ ID NO:4) in C3 loci plasmid (p397-Syn Rabies G, FIG. 1). The donor plasmid was made by taking a ~1.6 kb XhoI-XmaI with I3L-Synthetic Rabies G PCR fragment and cloning it into pHM606.1 (pC3), generating p397-Syn Rabies G (pC3 I3Lp Syn Rabies G, FIG. 1). In vitro recombination was carried out in primary chicken embryo fibroblast (1° CEF) cells.

Generation of Recombinant vCP3006.

Figure 2:
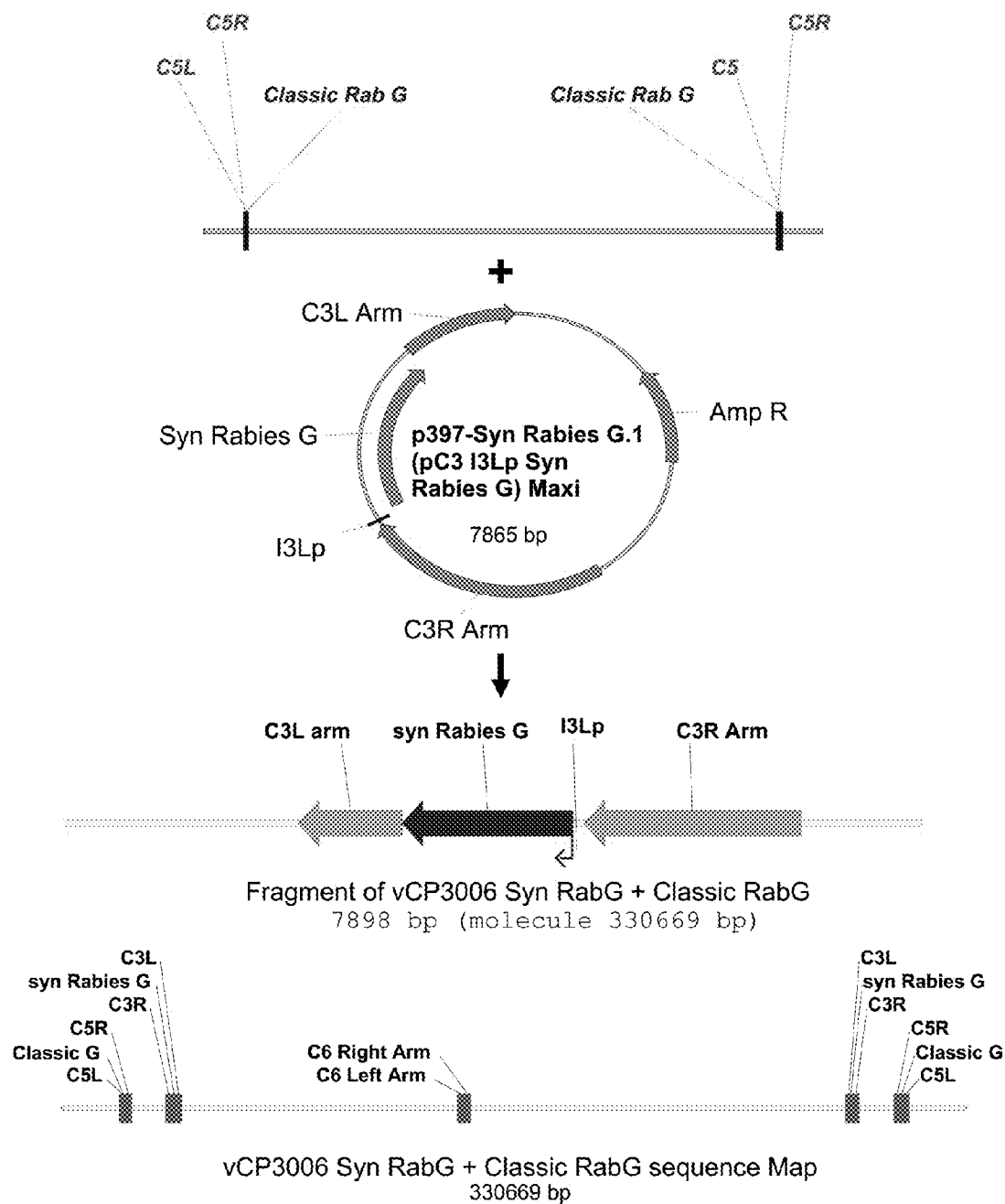
FIG. 2 provides a schematic representation of genomic organization of vCP3006, carrying synthetic Rabies G at C3 site and classic Rabies G at C5 site.

To initiate an in vitro recombination (IVR), first 1° CEF cells were transfected with 20 μg of Not I-digested plasmid p397-Syn Rabies G using FuGENE-6® reagent (Roche). The transfected cells were subsequently infected with ALVAC CP65a Stock at MOI of 10. After 24 hr, the transfected-infected cells were harvested, sonicated and used for recombinant virus screening. Recombinant plaques were screened based on the plaque lift hybridization method using a 140 base pair (bp) unique I3L probe (FIG. &) labeled with North2South Biotin Random Prime Labeling Kit (Thermo Scientific#17075) and detected with North2South Chemiluminescent Hybridization and Detection Kit (Thermo Scientific#17097). After five sequential rounds of plaque purification, a recombinant designated as vCP3066.4.1.3.1.1.3 was generated. A single plaque was selected from the 6$^{th}$ round of plaque purification and expanded to P1 (1×T25), P2 (1 well in a 6-well plate), P3 (1 well in a 6-well plate), P4 (1×T75 flask), and P5. Infected cells from P5 roller bottles were harvested and concentrated to produce vCP3006 stock. A schematic representation of vCP3006 generation is shown in FIG. 2.

Analysis of vCP3006.

Verification of genetic purity was done on the P5 stock using synthetic Rabies G and C3 site probes for hybridization. For Southern blot hybridization, genomic DNA was extracted from vCP3006 P5, digested with Xba I, Hind III, and BamHI, and separated by agarose electrophoresis. The digested genomic DNA was transferred to nylon membrane and subjected to Southern blot analysis by probing with a synthetic Rabies G specific probe. Primers RabG.1F (SEQ ID NO:52) and RabG.1R (SEQ ID NO:53) were used to amplify the synthetic Rabies G-specific probe.

Western Blot.

Primary CEF cells were infected with P5 stock at MOI of 4.5 and incubated at 37° C. for 24 hrs. For comparison of the G expression level, cells were also infected with the parental vCP65a using the same multiplicity of infection. The cells and culture supernatant were then harvested. Sample proteins were separated on a 10% SDS-PAGE gel, transferred to PVDF membrane. The membrane was incubated with mouse anti-Rabies G MAb (Chemicon #MAB8727) at a dilution of 1:500 followed by alkaline phosphatase conjugated anti-Mouse antibody.

Sequence Analysis.

A more detailed analysis of the P5 stock genomic DNA was performed by PCR amplification and sequence analysis of the flanking arms of the C3 locus and the synthetic Rabies G insert. Primers C3R.3F (SEQ ID NO:44) and C3L.1R (SEQ ID NO:47), located in the arms of the C3 locus in the ALVAC genome, were used to amplify the entire C3L-Syn Rabies G-C3R fragment (SEQ ID NO:2), and primers shown in FIG. 37 were then used to sequence the fragment.

Results.

Figure 3:
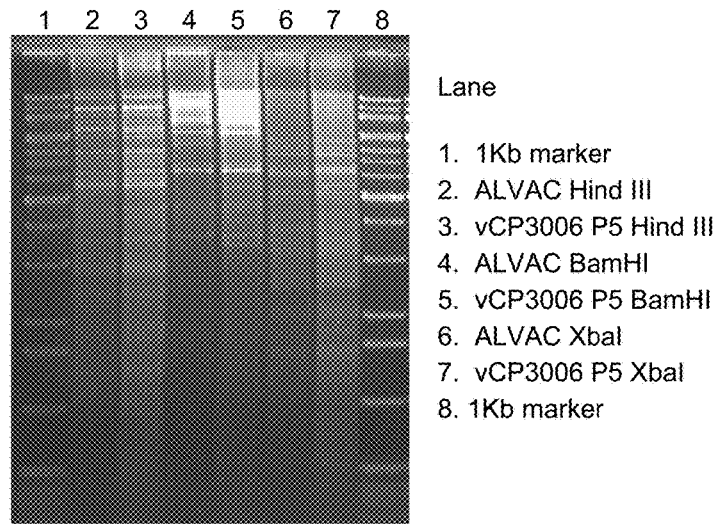
FIG. 3 is an image of genomic DNA isolated from wild type ALVAC and vCP3006, which had been digested with HindIII, BamHI or XbaI, and separated using agarose gel electrophoresis.
Figure 4:
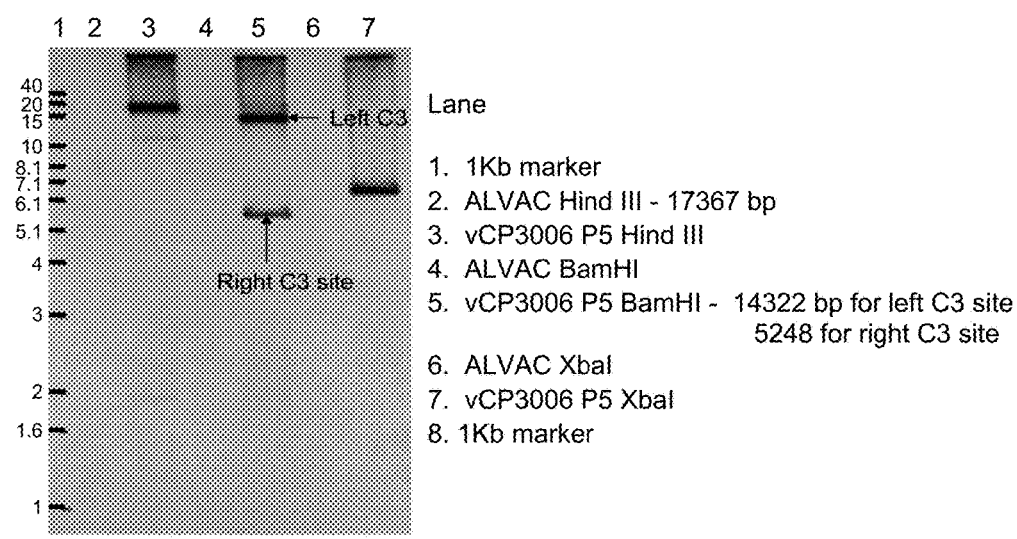
FIG. 4 presents a Southern Blot of the gel depicted in FIG. 3 (genomic DNA from wt ALVAC and vCP3006), which had been hybridized with a synthetic Rabies G-specific probe.

The homogeneity of the P5 stock of vCP3006 was confirmed by hybridization as 100% positive for the synthetic Rabies G and 100% negative for the C3 site. The titer of the P5 stock vCP3006 virus was $1.88 \times 10^9$ pfu/ml. The genomic integrity of recombinant vCP3006 was also verified by Southern blot analysis after separation of restriction enzyme digested genomic DNA in a gel electrophoresis (FIG. 3). Southern blot analysis using synthetic Rabies G specific probe revealed bands of expected sizes (14322 bp and 5248 bp BamHI, 17367 bp HindIII, and 6293 bp XbaI; FIG. 4), demonstrating the correct insertion of synthetic Rabies G into the C3 loci. The two bands on lane 5 (FIG. 4) also confirms insertion of synthetic rabies G into both sites of C3 (14322 bp for left C3 site and 5248 bp for right C3 site).

Figure 5:
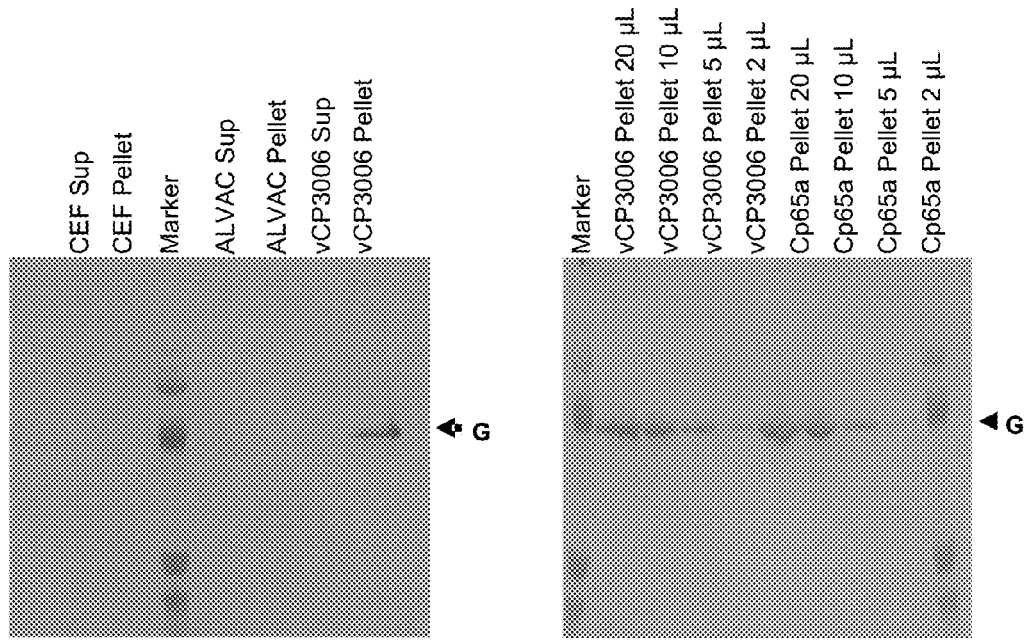
FIG. 5 presents a Western blot analysis of vCP3006 expression. A band corresponding to rabies virus G could only be detected in vCP3006 infected cell pellet (left). Different amounts of infected cell samples from cells infected with similar MOI of vCP3006 or vCP65a were loaded for comparison of G protein expression (right)
Figure 6:
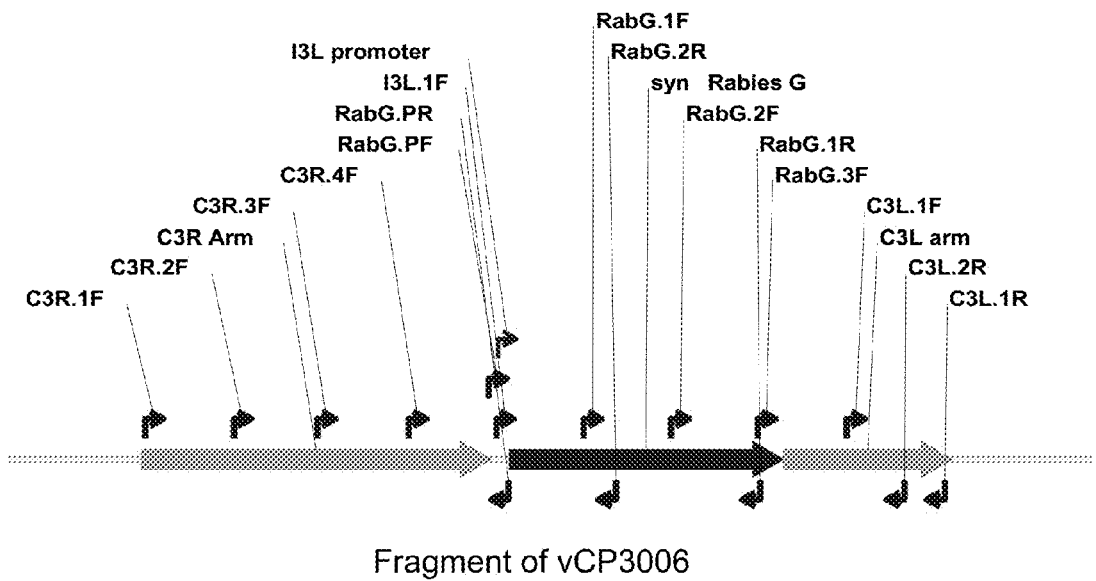
FIG. 6 provides a schematic drawing of vCP3006 C3 region showing primer locations.

For expression analysis of rabies virus G, primary CEF cells were infected with P5 stock of vCP3006 or vCP65a at MOI of 4.5. Supernatant as well as infected cell samples were processed and subjected to Western blot analysis. As shown in FIG. 5, rabies virus G was detectable in infected cell pellet, but not in supernatant samples, suggesting that G is not incorporated to ALVAC virions at a detectable level (FIG. 5 left). As the anti-rabies monoclonal recognizes both the classical G and the additional codon-optimized G in vCP3006, an attempt was done to compare the amount of G expressed vCP65a to that of vCP3006. For this purpose, cells were infected at similar MOI and different amounts of the total cell lysates were subjected to Western blot analysis (FIG. 5, right). Comparing the respective lanes loaded with 2 µl of cell lysates, it appears that the G band from vCP3006 is more abundant than the respective lane of vCP65a. This suggests that, vCP3006 expresses more G than does vCP65a. A PCR product covering flanking arms of the C3 locus and the synthetic Rabies G insert was sequenced using primers shown in FIG. 6 (full descriptions of which are presented in FIG. 37). The sequence analysis demonstrated that the sequences of the synthetic Rabies G and C3L and C3R regions were as expected (FIGS. 7A-7C), and the entire C3L to C3R fragment has the sequence as set forth in SEQ ID NO: 2. The predicted synthetic Rabies G peptide sequence is presented in FIG. 8 (SEQ ID NO:1), and is identical to the wild type Rabies G peptide sequence.

Example 2—Construction of Recombinant vCP3015, Co-Expressing Rabies Virus Glycoprotein and OX40L Summary.

Figure 9:
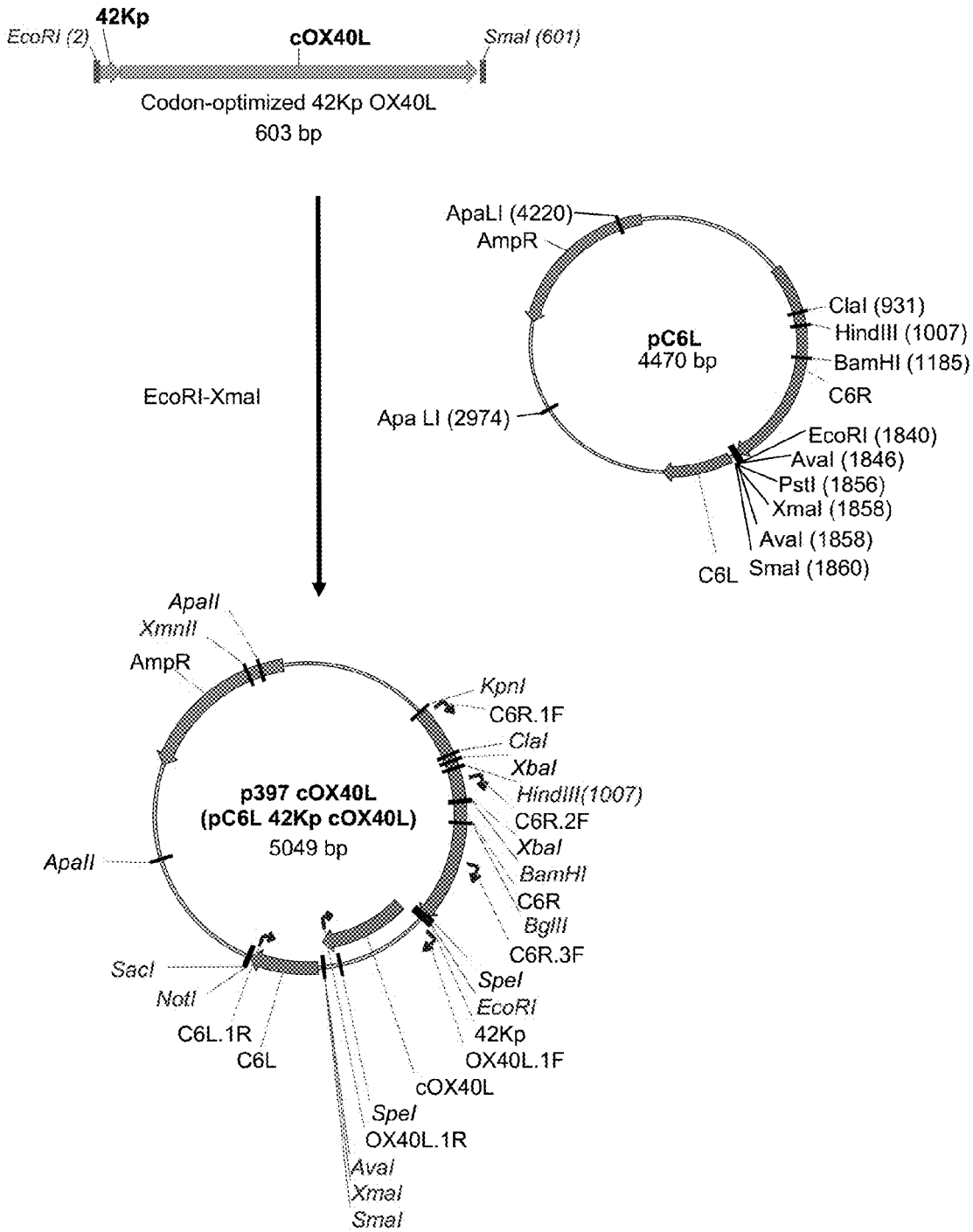
FIG. 9 is a schematic cloning diagram of donor plasmid p397-cOX40L.

Generation and characterization ALVAC recombinant in which a canine OX40 ligand (cOX40L) has been inserted into the C6 locus (one copy) in the background of vCP65a carrying a classic Rabies virus G in the C5 loci (2 copies). A codon-optimized synthetic canine OX40 Ligand (cOX40L, tumor necrosis factor ligand superfamily member 4-like) was inserted into the C6 locus of parental virus ALVAC CP65a (titer 6.1×10e7 pfu/mL, resuspended in 1 mL Tris pH9 buffer). The donor plasmid was p397-cOX40L (pC6 42 Kp cOX40L) a synthetic cOX40L with 42K promoter in C6 locus, and was produced by taking a ~0.6 kb EcoRI-XmaI synthetic canine OX40L fragment with 42K promoter and cloning into pC6L (FIG. 9). In vitro recombination was carried out in primary 1° CEF cells, according to procedure disclosed in Example 1. Screening of recombinant plaques was essentially done as described under Example 1 using a 551 bp cOX40L-specific probe. After four sequential rounds of plaque purification, the recombinant designated as vCP3015.9.2.1.2 was generated. Single plaques were selected from the 4th round of plaque purification, and expanded to obtain P1 (T-25 flask), P2 (T-75 flask) and P3 (4 roller bottles) of vCP3015.9.2.1.2. P3 was harvested, infected CEFs pelleted, and supernatant removed. The infected CEFs were resuspended in 1 mM Tris, pH 9.0, sonicated, and concentrated to produce virus stock of vCP3015. A schematic representation of vCP3015 generation is shown in FIG. 10.

Analysis of vCP3015.

Genomic DNA from P3 of vCP3015 was extracted, digested with NruI, and run in duplicate on a 0.8% agarose gel. The NruI digested genomic DNA was transferred to nylon membrane and Southern Blot analysis was essentially performed as described under Example 1 by probing either with cOX40L or classic Rabies G probes. PCR primers OX40L.1F (SEQ ID NO:61) and OX40L.1R (SEQ ID NO:62) were used to amplify a cOX40L probe, and primers CP65.2R (SEQ ID NO:39) and C5R.3F (SEQ ID NO:30) were used to amplify classical rabies virus G probe.

Western Blot.

Primary CEF cells were infected with P3 stock of vCP3015 at MOI of 10 and incubated at 37° C. for 26 hrs. The cells and culture supernatant were then harvested. Sample proteins were separated on a 10% SDS-PAGE gel, transferred to PVDF membrane, and probed with a monoclonal anti-Rabies G antibody (Chemicon #MAB8727) at a dilution of 1:500 followed by alkaline phosphatase conjugated anti-Mouse antibody.

Sequence Analysis.

For the classic Rabies G at the C5 site, a detailed analysis of the P3 stock genomic DNA was performed by PCR amplification and sequence analysis of the C5 locus containing the classic Rabies G insert. Primers 7635CXL.R (SEQ ID NO:35) and 7635CXL.F (SEQ ID NO:36), located at the end of the arms of the C5 locus were used to amplify the entire C5R-classic Rabies G-05L fragment. The fragment was then sequenced using the primers listed in FIG. 37. For cOX40L at C6, a detailed analysis of the P3 stock genomic DNA was performed by PCR amplification and sequence analysis of the C6 locus containing the cOX40L insert. Primers C6R.1F (SEQ ID NO:57) and C6L.1R (SEQ ID NO:60), located at the end of the arms of the C6 locus were used to amplify the entire C6R-cOX40L-C6L fragment. The fragment was sequenced using the primers listed in FIG. 37.

Results.

Figure 11:
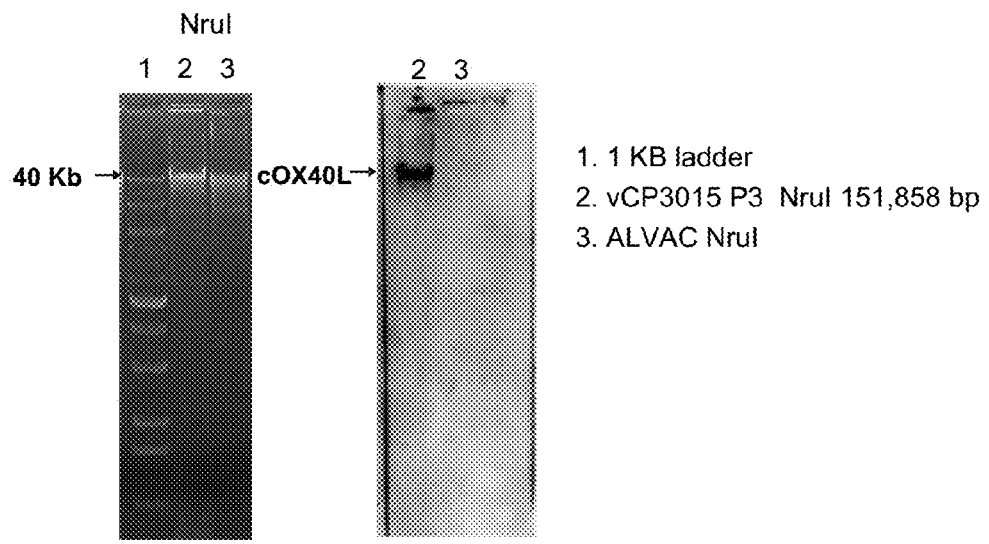
FIG. 11 is an agarose gel image presenting the separation of NruI digested genomic DNA on gel electrophoresis (right) and Southern blot hybridization using cOX40L probe.
Figure 12:
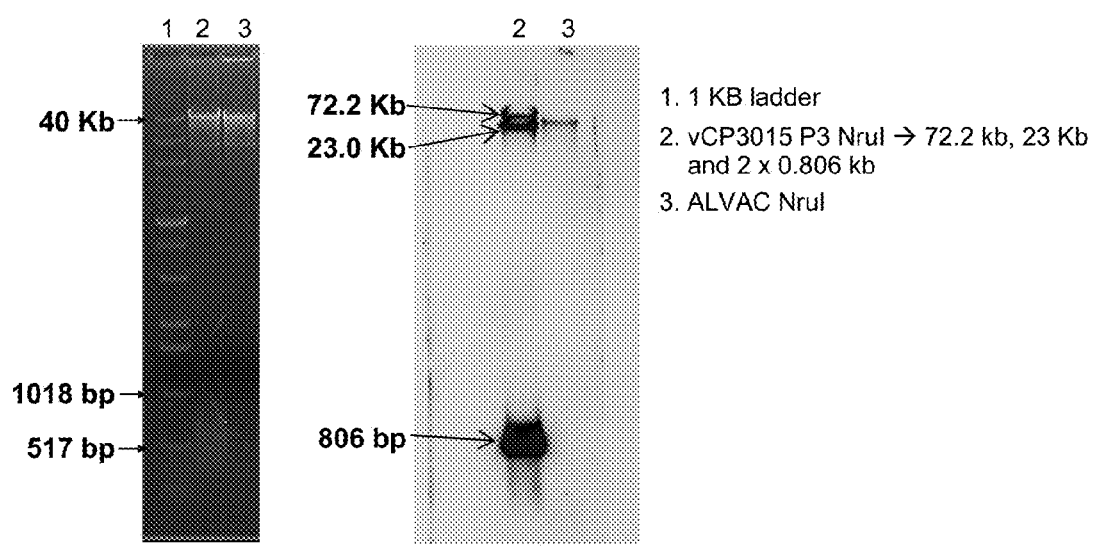
FIG. 12 is an agarose gel image presenting separation of NruI digested genomic DNA (left) and Southern blot hybridization using classical rabies virus G probe (right). This probe spans both the Classic Rabies G protein and 389 bp of the C5 right arm, because of the 389 bp probe-binding there is a weak hybridization signal with the parental ALVAC genome, (lane 3), but with a band size different from that of vCP3015.

The homogeneity of the P3 stock of vCP3015 was confirmed by hybridization as 100% positive for the cOX40L insert and 100% negative for the empty C6 site. The titer of the P3 stock vCP3015 virus was 8.5×10^9 pfu/ml. The genomic integrity of recombinant vCP3015 was also verified by Southern blot. For cOX40L, the probe detected a 151,858 bp fragment (FIG. 11) and for classic Rabies G, the probe detected a 72,175 bp fragment for the left C5 site, a 23,014 bp fragment for the right C5 site, and an 806 bp fragment for both C5 sites (FIG. 12).

Figure 13:
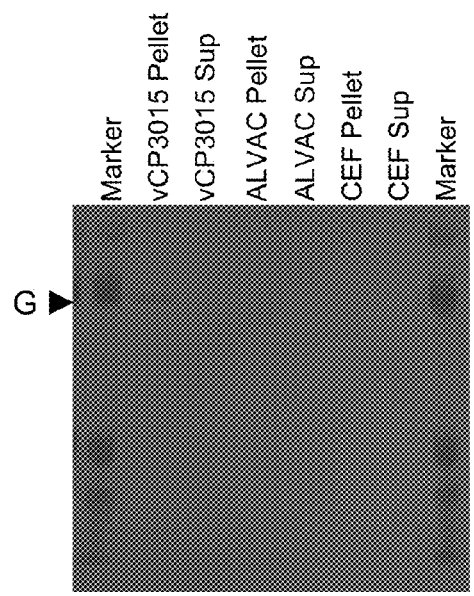
FIG. 13 is a Western blot analysis of vCP3015. A band corresponding to rabies virus G could only be detected in the pellet from cells infected with vCP3015.
Figure 14:
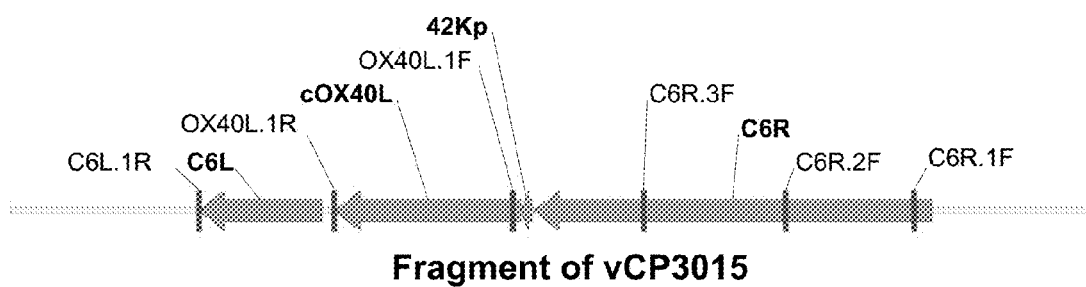
FIG. 14 is s schematic drawing of the vCP3015 C6 region showing primer locations.
Figure 17:
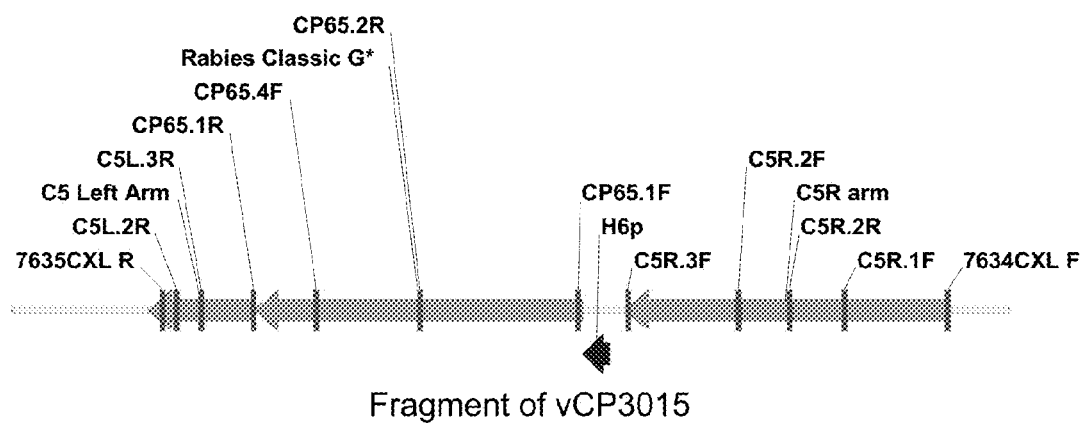
FIG. 17 a schematic drawing of vCP3015 C5 region showing primer locations.
Figure 20:
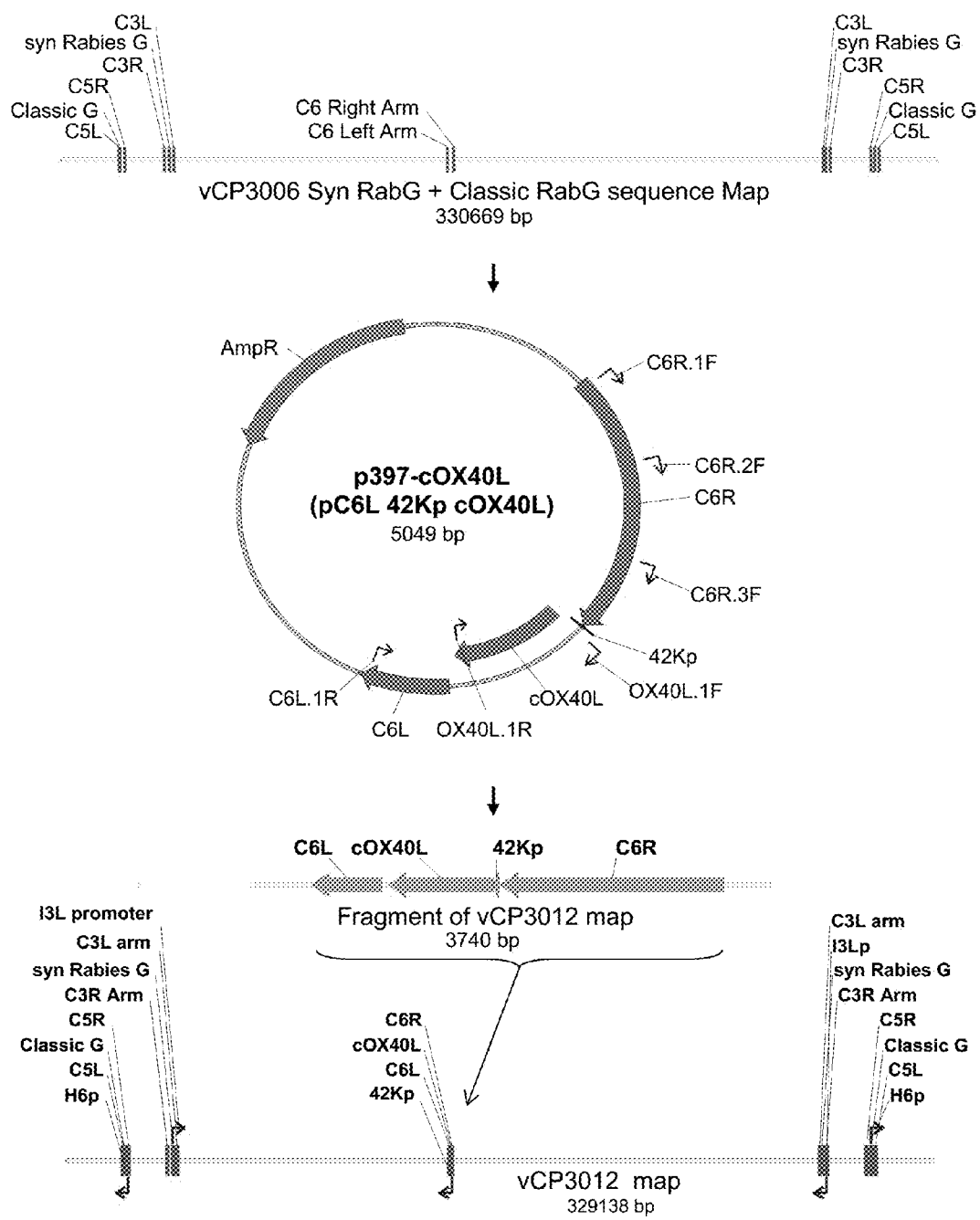
FIG. 20 is a schematic representation of genomic organization of vCP3012, carrying classic Rabies virus G at the C5 site, codon-optimized synthetic rabies virus G at the C3 site and cOX40L at the C6 site.

For expression analysis of classical rabies virus G, primary CEF cells infected with P3 stock of vCP3015 at MOI of 10. Supernatant as well as infected cell samples were processed and subjected to Western blot analysis. As shown in FIG. 13, rabies virus G was detectable in infected cell pellet at the expected size, but not in supernatant samples. A PCR product covering flanking arms of the C6 locus and the cOX40L insert was sequenced using primers shown in FIG. 14. The sequence analysis demonstrated that the sequences of the cOX40L and C6L and C6R regions are as expected (FIGS. 15A-15B). A PCR product covering flanking arms of the C5 locus and the classical rabies virus G insert was sequenced using primers shown in FIG. 17. The resultant sequence is shown in FIGS. 18A-18B (SEQ ID NO:13).

Example 3—Construction of Recombinant vCP3012, Co-Expressing Classical Rabies Virus G, Codon-Optimized Rabies Virus G and OX40L Summary.

Generation and characterization ALVAC recombinant in which a canine OX40 ligand (cOX40L) has been inserted into the C6 locus (one copy) in the background of vCP3006 carrying classic rabies virus G in the C5 loci (2 copies) and codon-optimized rabies virus G in the C3 loci (2 copies). Codon-optimized synthetic canine OX40L sequence (led by 42K promoter) was inserted into the C6 locus of parental virus ALVAC vCP3006 P5 (stock titer was 1.88×10^9 pfu/ml). The donor plasmid 397-cOX40L (pC6 42 Kp cOX40L) was identical to that used in Example 2 in FIG. 9, as was the in vitro recombination method.

Screening of recombinant plaques was essentially done as described in Example 1 using a 551 bp cOX40L-specific probe. After 4 sequential rounds of plaque purification, the recombinant designated as vCP3012.9.2.1.3 was generated. Single plaques were selected from the final round of plaque purification, and expanded to obtain P1 (6 well plate), P2 (T-75 flask) and P3 (roller bottle) stocks to amplify vCP3012.9.2.1.3. The infected cells as well as the culture supernatant from the roller bottles was harvested and pelleted. After removing the supernatant, the pellet was sonicated and concentrated to produce vCP3012 stock virus.

Analysis of vCP3012.

Genomic DNA was extracted from vCP3012 (P3), digested with PmeI, NruI, and BamHI, and separated by agarose electrophoresis. The digested genomic DNA was transferred to nylon membrane and Southern blot analysis was essentially performed as described under example 1 by probing with cOX40L, synthetic rabies G, and classic rabies G probes. PCR primers OX40L.1F (SEQ ID NO:61) and OX40L.1R (SEQ ID NO:62) were used to amplify cOX40L probe, primers CP65.2R (SEQ ID NO:39) and C5R.3F (SEQ ID NO:30) were used to amplify classical rabies virus G probe, and primers RabG.1R (SEQ ID NO:53) and RabG.1F (SEQ ID NO:52) were used to amplify synthetic rabies virus.

Western Blot.

Primary CEF cells were infected with P3 stock of vCP3012 at MOI of 10 and incubated at 37° C. for 24 hrs. The cells and culture supernatant were then harvested. Sample proteins were separated on a 10% SDS-PAGE gel, transferred to PVDF membrane. The membrane was incubated with a monoclonal anti-Rabies G antibody (Chemicon #MAB8727) at a dilution of 1:500 followed by alkaline phosphatase conjugated anti-Mouse antibody.

Sequence Analysis.

For cOX40L at C6, analysis of the P3 stock genomic DNA was performed by PCR amplification and sequence analysis of the C6 locus containing the cOX40L insert. Primers C6R.1F (SEQ ID NO:57) and C6L.1R (SEQ ID NO:60), located at the end of the arms of the C6 locus were used to amplify the entire C6R-cOX40L-C6L fragment. The fragment was sequenced using the primers listed in FIG. 37. For Synthetic Rabies G at C3, analysis of the P3 stock genomic DNA was performed by PCR amplification and sequence analysis of the flanking arms of the C3 locus and the synthetic rabies G insert. Primers C3R.2F (SEQ ID NO:43) and C3L.1R (SEQ ID NO:47) located at the arms of the C3 locus were used to amplify the entire C3R-Syn Rabies G insert-C3L fragment. For classic Rabies G at C5, analysis of the P3 stock genomic DNA was performed by PCR amplification and sequence analysis of the C5 locus containing the classic Rabies G insert. Primers 7635CXL.R (SEQ ID NO:35) and 7635CXL.F (SEQ ID NO:36), located at the end of the arms of the C5 locus were used to amplify the entire C5R-classic Rabies G-05L fragment. The fragment was sequenced using the primers listed in FIG. 37.

Results.

The homogeneity of the P3 stock of vCP3012 was confirmed by hybridization as 100% positive for the cOX40L insert and 100% negative for the empty C6 site. The titer of the P3 stock of vCP3012 virus was 4×10^9 pfu/ml. The genomic integrity of recombinant vCP3012 was also verified by Southern blot. For cOX40L, the probe detected a 200.362 bp fragment (FIG. 21); for synthetic rabies G, 14322 bp for the left C3 site and 5248 bp for right C3 site (FIG. 22); and for classic rabies G 806 bp for both sites, 72,436 bp for the left C5 site and 23,275 bp for the right C5 site (FIG. 23). These expected sizes indicated the correct insertion of cOX40L at the C6 locus, synthetic rabies G at the C3 loci, and classic Rabies G at the C5 loci.

For expression analysis of classical as well as synthetic rabies virus G, primary CEF cells infected with P3 stock of vCP3012 at MOI of 10. Supernatant as well as infected cell samples were processed and subjected to Western blot analysis. As shown in FIG. 24, rabies virus G was detectable in infected cell pellet at the expected size.

Figure 27:
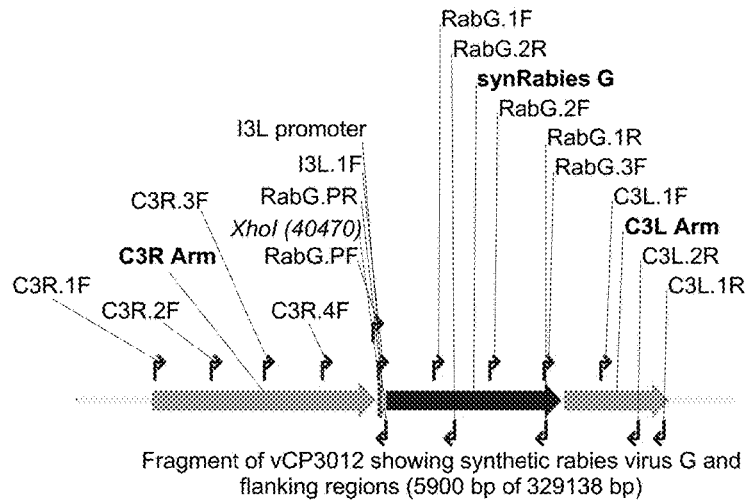
FIG. 27 a schematic drawing of vCP3012 C3 region showing primer locations.
Figure 31:
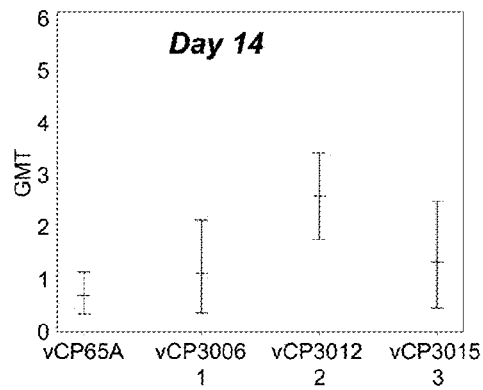
FIG. 31 is a graph of GMT and 95% confidence interval (CI) for day 14.
Figure 32:
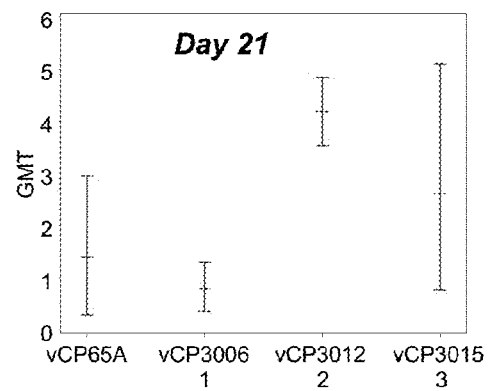
FIG. 32 is a graph of GMT and 95% confidence interval (CI) for day 21.
Figure 33:
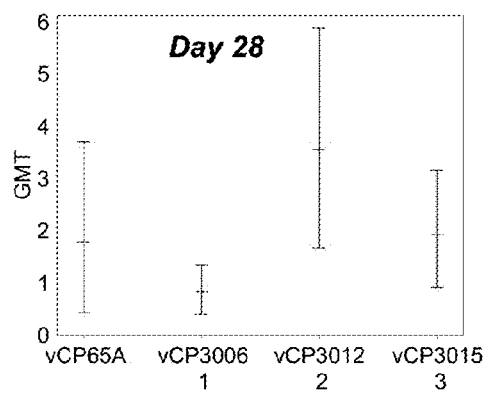
FIG. 33 is a graph of GMT and 95% confidence interval (CI) for day 28.
Figure 34:
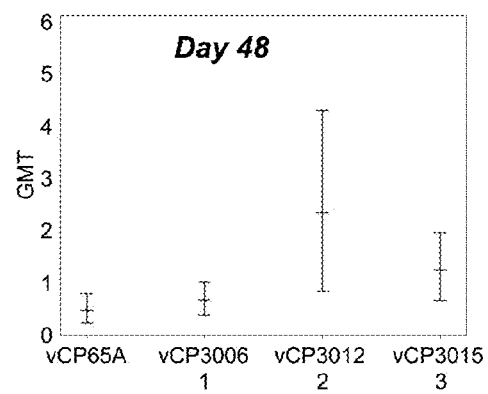
FIG. 34 is a graph of GMT and 95% confidence interval (CI) for day 48.
Figure 35:
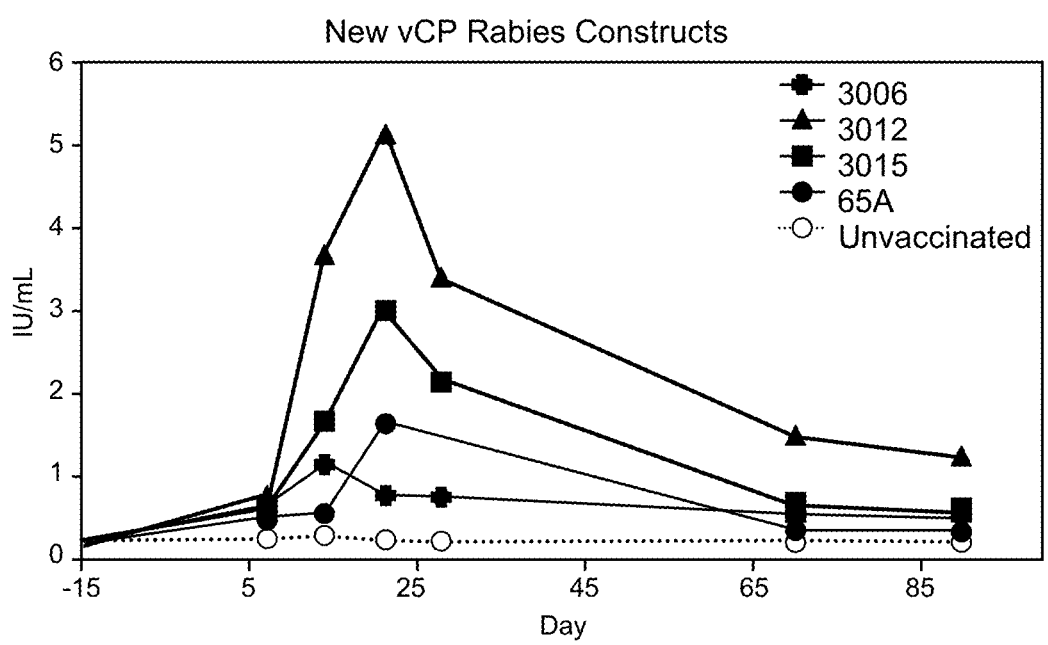
FIG. 35 is a graph presenting Group titers.

A PCR product covering flanking arms of the C6 locus and the cOX40L insert was sequenced using primers shown in FIG. 25. The sequence analysis demonstrated that the sequences of the cOX40L and C6L and C6R regions are as expected (FIG. 26). A PCR product covering flanking arms of the C3 locus and the synthetic rabies virus G insert was sequenced using primers shown in FIG. 27. The resultant sequence is shown in FIGS. 28A-28C (SEQ ID NO:20). The results showed that the sequences of the synthetic Rabies G insert and the C3 left and right arms around the synthetic rabies G insert in vCP3012 were as expected. A PCR product covering flanking arms of the C5 locus and the classical rabies virus G insert was sequenced using primers shown in FIG. 29. The resultant sequence is shown in FIGS. 30A-30B (SEQ ID NO:23). The results showed that the sequences of the classical Rabies G insert and the C5 left and right arms around the classical rabies G insert in vCP3012 were as expected.

Example 4—Efficacy Evaluation of Three New Recombinant Canarypox Vaccines in Comparison to vCP65A by Vaccination and Serology in Dogs For this study, all dogs were randomly assigned to five different treatment groups (6 dogs in each group) with factor of litter ID. Dogs from the different vaccine groups were randomly assigned to pens with vaccine groups commingled within the same pen. Dogs were assigned to pens segregated by sex. Dogs in the control group will be housed in a different pen from the vaccinates during the pre-challenge period. SAS® software V9.1 Enterprise Guide was used for producing the randomization table. Dogs were vaccinated on Day 0 with candidate vaccines (Table 1). Blood samples were taken on Day 0, 7, 14, 21, 28, 48, 70 and 90 and rabies antibody titers determined by RFFIT.

TABLE 1

Treatment Groups

| Groups | Vaccine | Vaccine target dose (TCID50/ml) | Route/ Once | Volume | Dogs per Group |
|---|---|---|---|---|---|
| A | Test Vaccine #1 vCP3006 | $10^{5.9}$ | SQ | 1 ml | 6 |
| B | Test Vaccine #2 vCP3012 | $10^{5.9}$ | SQ | 1 ml | 6 |
| C | Test Vaccine #3 vCP3015 | $10^{5.9}$ | SQ | 1 ml | 6 |
| D | Reference vaccine vCP65A | $10^{5.9}$ | SQ | 1 ml | 6 |
| E (negative control) | — | — | — | — | 6 |

The geometric mean RFFIT titers and the 95% confidence intervals were calculated for each group (A, B, C, and D) and day. The antibody peak appears to be on day 21. The results are shown in Table 2. On day 14, vCP3012 vaccinates have markedly higher titers than all other groups. On Day 21, both groups vaccinated with a cOX40L containing canarypox vector have greater neutralizing responses than other vaccinated groups. Thus, an earlier onset of immunity and higher peak titers are clearly seen in groups vaccinated with a vector expressing cOX40L. After Day 21 and until the end of the study, vCP3012 vaccinates maintained markedly higher titers than all other groups. On Day 90, all of the dogs vaccinated with vCP3012 had titers greater than 0.5 IU/ml, a titer generally considered as protective in rabies virulent challenge experiments. Thus, cOX40L expression improves the duration of immunity of a canarypox vectored rabies vaccine.

Conclusion.

Compared to the parent vCP65a, the addition of cOX40L into the backbone of either vCP65a or vCP3006 clearly enhances the onset of anti-rabies immunity as measured by anti-rabies neutralizing antibodies; increases the peak anti-rabies neutralizing antibody titer as well as prolongs the duration of anti-rabies immunity for at least 90 days (the last date of blood sampling).

TABLE 2

Geometric Mean Titers and 95% confidence interval

| Day | Group | GMT | Lower 95% CI of GMT | Upper 95% CI of GMT |
|---|---|---|---|---|
| 7 | #1 vCP3006 | 0.57 | 0.30 | 1.08 |
|   | #2 vCP3012 | 0.61 | 0.34 | 1.10 |
|   | #3 vCP3015 | 0.47 | 0.23 | 0.95 |
|   | Ref vCP65A | 0.41 | 0.22 | 0.76 |
| 14 | #1 vCP3006 | 0.78 | 0.29 | 2.08 |
|   | #2 vCP3012 | 3.36 | 1.71 | 6.63 |
|   | #3 vCP3015 | 0.98 | 0.39 | 2.43 |
|   | Ref vCP65A | 0.54 | 0.27 | 1.08 |
| 21 | #1 vCP3006 | 0.68 | 0.36 | 1.30 |
|   | #2 vCP3012 | 4.84 | 3.53 | 6.64 |
|   | #3 vCP3015 | 1.97 | 0.76 | 5.10 |
|   | Ref vCP65A | 0.92 | 0.29 | 2.96 |
| 28 | #1 vCP3006 | 0.66 | 0.34 | 1.29 |
|   | #2 vCP3012 | 3.06 | 1.61 | 5.82 |
|   | #3 vCP3015 | 1.63 | 0.85 | 3.10 |
|   | Ref vCP65A | 1.15 | 0.36 | 3.65 |
| 48 | #1 vCP3006 | 0.55 | 0.32 | 0.95 |
|   | #2 vCP3012 | 1.81 | 0.77 | 4.25 |
|   | #3 vCP3015 | 1.06 | 0.60 | 1.90 |
|   | Ref vCP65A | 0.35 | 0.16 | 0.73 |
| 70 | #1 vCP3006 | 0.39 | 0.19 | 0.78 |
|   | #2 vCP3012 | 1.16 | 0.66 | 2.03 |
|   | #3 vCP3015 | 0.58 | 0.37 | 0.89 |
|   | Ref vCP65A | 0.26 | 0.13 | 0.49 |
| 90 | #1 vCP3006 | 0.40 | 0.21 | 0.76 |
|   | #2 vCP3012 | 0.96 | 0.54 | 1.70 |
|   | #3 vCP3015 | 0.48 | 0.28 | 0.82 |
|   | Ref vCP65A | 0.25 | 0.14 | 0.42 |

Example 5—Evaluation of the Immunogenicity of Three New Recombinant Canarypox Vaccines by Virulent Challenge in Dogs Thirty (30) two to three month-old, purpose-bred beagles were randomly allocated into one of five treatment groups (n=6), using litter ID as the primary randomization factor. On Day 0 all dogs were vaccinated according to Table 3 below.

TABLE 3

Vaccination scheme

| Groups | Vaccine* | Vaccine backtitration results (TCID$_{50}$/ml) | TCID$_{50}$ administered | Volume | Dogs per Group |
|---|---|---|---|---|---|
| A | Test Vaccine #1 vCP3006 | $10^{6.16}$ | $10^{6.16}$ | 1 ml | 6 |
| B | Test Vaccine #2 vCP3012 | $10^{6.54}$ | $10^{6.22}$ | 0.7 ml | 6 |
| C | Test Vaccine #3 vCP3015 | $10^{6.08}$ | $10^{5.87}$ | 1 ml | 6 |
| D | Reference vaccine vCP65A | $10^{6.12}$ | $10^{6.07}$ | 1 ml | 6 |
| E (- control) | — | — | — | — | 6 |

*Vaccine target titer $10^{5.9}$ TCID$_{50}$/ml.

Animals were monitored, for one hour post-vaccination for acute systemic reactions. Injection sites were examined and rectal temperatures recorded daily for 3 days thereafter. Blood was collected for rabies antibody titers as measured by Rapid Fluorescent Focus Inhibition Test (RFFIT) prior to, and at regular intervals following vaccination. Based on a favorable serological response, dogs from Group C (vCP3015) were subject to a virulent rabies challenge approximately one year after vaccination (Day 397). The challenge material (New York Strain 1 42.90 at a dilution of 1:100) was administered under anesthesia by the intramuscular route, into the left and the right frontalis muscles (0.5 ml into each muscle). Back titration of the challenge material was performed in accordance with QCD-CM-030. Post-challenge, dogs were observed for 30 days for mortality or evidence of progressive neurological signs. Serum was obtained from all dogs immediately after euthanasia for RFFIT testing. Both brain hemispheres were collected at necropsy and the right hemisphere was submitted for detection of rabies virus using direct immunofluorescence.

All statistical analyses were performed using SAS, Cary, N.C. (SAS Version 9.1, Enterprise Guide). All tests were two-sided and statistical significance was declared at a P value of 0.05 or less. The primary variable was serum rabies antibody titer as measured by Rapid Fluorescent Focus Inhibition Test (RFFIT). Seroconversion was defined as a change from a negative antibody titer (under detection threshold, i.e. <0.2 IU/ml) to a positive rabies antibody titer (>0.2 IU/ml). All dogs were seronegative for rabies prior to vaccination except for one dog in Group A (vCP3006) that presented with a low rabies titer of 0.3 IU/ml and a value of 0.5 IU/ml on a re-test. Three dogs from Group E (negative control group) demonstrated low antibody titers within 30 days of initiation of the study. By Day 48 all dogs in Group E were seronegative and remained negative throughout the study. The low rabies titers were almost certainly due to residual maternal antibodies. The Group Geometric Mean RFFIT antibody titer following vaccination for Groups A, B, C and D are shown in Table 4.

TABLE 4

Serum Rabies Ab Geometric Mean Titer (IU/ml) per Group following vaccination.

| Group | Day post-vaccination - RFFIT GMT IU/ml | | | | | | |
|---|---|---|---|---|---|---|---|
| | 7 | 14 | 21 | 28 | 48 | 70 | 90 |
| A vCP3006 | 0.57 | 0.78 | 0.68 | 0.66 | 0.55 | 0.39 | 0.40* |
| B vCP3012 | 0.61 | 3.36* | 4.84* | 3.06* | 1.81* | 1.16* | 0.96* |
| C vCP3015 | 0.47 | 0.98 | 1.97* | 1.63 | 1.06* | 0.58* | 0.48* |
| D vCP65A | 0.41 | 0.54 | 0.92 | 1.15 | 0.35 | 0.26 | 0.25 |
| E (- control) | 0.23 | 0.25 | 0.21 | 0.20 | 0.20 | 0.20 | 0.20 |

*GMT significantly (p < 0.05) and different from the reference vaccine (Group D vCP65A)

Seroconversion was observed for all dogs in Group B (vCP3012) and 5/6 dogs in Groups A (vCP3006), C (vCP3015) and D (vCP65A) seven days following vaccination. Dogs vaccinated with vCP3012 demonstrated a significantly and unpredictably higher rabies titer in comparison to Group A (vCP3006) and the reference vaccine group D (vCP65A) from Days 14 through Day 90. The rabies GMT for Group C (vCP3015) was significantly higher than the reference vaccine group D (vCP65A) on Days 21, 48, 70 and 90. Dogs vaccinated with vCP3006 did not show a significant difference in rabies titers in comparison to the reference vaccine Group D (vCP65A) except for Day 90.

Approximately one year after vaccination, dogs from Group C (vCP3015) were subjected to a virulent rabies challenge. The remaining dogs from Group B and E remained under the current study number until termination of the study at a later date. The calculated 50% mouse lethal dose ($MLD_{50}$) of the challenge virus administered was 2.2 $\log_{10}$ (158.5 $MLD_{50}$) in 0.03 ml. As 1 ml was administered to each dog, the dog dose was 3.96 $\log_{10}$ $MLD_{50}$. The pre- and post-challenge RFFIT titers, and post-challenge rabies fluorescent antibody results and morbidity/mortality data are shown in Table 5 below.

TABLE 5

Summary results

| Vaccine Group | ID | Serology RFFIT (IU/ml)* | | Rabies fluorescent antibody results Brain sample | Morbidity/ Mortality** Day of death post-challenge |
|---|---|---|---|---|---|
| | | Pre-challenge (Day 392 post-vaccination)* | Post-challenge (day of euthanasia) | | |
| Group C vCP3015 | CCECAC | ≤0.2 | 0.9 | Negative | 30 |
| | CCECAN | ≤0.2 | 0.7 | Negative | 30 |
| | CCECAV | 0.2 | 5.8 | Negative | 30 |
| | CCECCY | 0.2 | 1.1 | Negative | 30 |
| | CCECEP | 0.8 | 3.4 | Negative | 30 |
| | CCECFE | 0.2 | 1.8 | Negative | 30 |
| Negative control group from study 10-074 | CBCCTX | ≤0.2 | ≤0.2 | Positive | 13 |
| | CBDCCE | ≤0.2 | ≤0.2 | Positive | 17 |
| | CBDCCY | ≤0.2 | 0.4 | Positive | 12 |

*All dogs euthanatized prior to Day 30 post-challenge demonstrated clinical signs of rabies infection.
**CBCCTX, CBDCCE and CBDCCY pre-challenge day was Day 752.

None of the Group C dogs demonstrated any clinical abnormalities up to 30 days post challenge. All dogs in the negative control group developed clinical signs compatible with canine rabies infection between Days 12 and 17, such as change in behavior, lethargy, salivation, facial twitching, difficulty to swallow, and limb paralysis. All dogs euthanatized up to 17 days post-challenge were positive for rabies fluorescent antibody testing and the remaining dogs euthanatized at the end of the study were negative for rabies fluorescent antibody testing in the brain tissue. Further, no local injection site reactions (diffuse swelling, firm swelling, pain upon palpation or pruritus) nor clinically significant elevations in rectal temperature were observed following vaccination.

Discussion.

Based on the pre-vaccination titer results, the final volume of each test vaccine was adjusted to reach a target titer of approximately $10^{5.9}$ TCID$_{50}$/ml. Consequently, a lower volume was administered at vaccination for vCP3012 (Group B) which had a higher titer pre-vaccination in comparison to the other test vaccines. The selection of animals subject to rabies challenge one or two years following vaccination was based on the rabies geometric mean serology titer over a 3 month period in comparison to the reference vaccine (Group D vCP65A). Group A (vCP3006) did not meet the challenge criteria, therefore dogs pertaining to that group were released from the study on Day 151. Groups B and C clearly met the challenge criteria. One and two-year duration of immunity evaluation was selected for vCP3015 and vCP3012, respectively. The selection of which test vaccine to evaluate first was based on the serology results and the construct with the lowest number of rabies G gene copies. Since the vCP3015 construct contains 2 copies and the vCP3012 contains 4 copies, vCP3015 was thus selected to be evaluated first. The two year duration of immunity evaluation will be conducted in dogs vaccinated with vCP3012 and compared to the reference group (vCP65A).

These results demonstrated the vCP constructs were safe when administered once via the subcutaneous route in dogs. Dogs vaccinated via the subcutaneous route with a single-dose of a construct containing 2 copies of the rabies G gene and the immunomodulator OX40L (vCP3015) at $10^{5.87}$ TCID$_{50}$/ml were protected against a virulent rabies challenge 1 year after vaccination. vCP3012, containing 4 copies of the rabies G gene and OX40L, induced an earlier and stronger rabies antibody response in comparison to all other vCP constructs, and will be evaluated by rabies challenge at 2 years post-vaccination.

Example 6—Other Effective Antigen/OX40L Combinations

Inventors envision many other combinations of antigen and OX40L will result in poxvirus-vectored vaccines having improved efficacy over poxvirus expressing the same antigen alone. Table 3 presents a non-limiting list of antigen and OX40L combinations, where the OX40L is selected based upon its likely ability to function as an effective genetic adjuvant in the target animal. FIG. 38 presents the alignment of known/putative OX40L from a variety of different species. A skilled person will appreciate that OX40L proteins may also vary somewhat within a single animal genus or species (e.g. Canis familiaris). Thus, OX40L proteins having sufficient homology to SEQ ID NO:12 should also function as effective genetic adjuvants in canine, and are encompassed by the instant invention. Additionally, inventors envision similar results are likely achievable using other vectors, including viral vectors, to express in vivo in an animal host genes encoding an antigen and an adjuvanting OX40L. For example, viral vectors include but are not limited to: DNA viruses, RNA viruses, herpes viruses, adenoviruses, adeno-like viruses, leukemia viruses, Newcastle disease virus (NDV), infectious bronchitis virus (IBV), infectious bursal disease virus (IBDV), marek's disease virus (MDV, SB1, and HVT), etc.

TABLE 3 combinations of antigen and OX40L, which are envisioned to function as genetically-adjuvanted, effective vaccine compositions

| Antigen | Target Animal | OX40L |
|---|---|---|
| Influenza, distemper (CDV), CPV, west nile, coronavirus, | Canine | SEQ ID NO: 12, or variant thereof having comparable adjuvancy in canine |
| Influenza, FCV, FeLV, FIPV, FIV, WNV, etc. | Feline | SEQ ID NO: 63, or variant thereof having comparable adjuvancy in feline |
| Influenza, WNV, E/W encephalitis virus, EHV, herpesvirus, vesicular stomatitis, infectious anemia, arteritis, AHSV, Hendra, etc. | Equine | SEQ ID NO: 64, or variant thereof having comparable adjuvancy in equine |
| BRSV, BVD, herpesvirus, pleuropneumoniae, adenovirus, parvo, enterovirus, FMDV, BTV, | Bovine | SEQ ID NO: 65, or variant thereof having comparable adjuvancy in bovine |
| PCV2, PRRSV, FMDV, BVD, Aujeszky's disease, Nipah, etc | Porcine | SEQ ID NO: 66, or variant thereof having comparable adjuvancy in porcine |
| MDV, SB1, HVT, NDV, IBDV), IBV | Avian | SEQ ID NO: 70, or variant thereof having comparable adjuvancy in avian |
| BTV, etc. | Ovine | SEQ ID NO: 71 |

The following numbered paragraphs provide non-limiting embodiments.

1. A composition comprising:
a) an expression vector comprising a polynucleotide encoding both:
i. one or more polypeptide selected from a Rabies G, an influenza, an FMDV, a BTV, a PCV2, a PRRSV, a WNV, a Nipah virus, a leukemia virus, a *leishmania* virus, an FIV, an FIPV, a FCV, an AHSV, a VSV, and an immunogenically effective variant or fragment thereof; and
ii. an OX40L polypeptide, or a comparably adjuvanting variant or fragment thereof; and b) a pharmaceutically or veterinarily acceptable vehicle, diluent or excipient.

2. The composition of paragraph 1 wherein the vector comprises a polynucleotide encoding an OX40L polypeptide from the target animal (i.e. type of animal to which the composition will be administered).

3. The composition of paragraph 2 wherein the OX40L polypeptide is at least 90% identical to the sequence as set forth in SEQ ID NO:12 (for canine target), SEQ ID NO:63 (for feline target), SEQ ID NO:64 (for equine target), SEQ ID NO:65 (for bovine target), or SEQ ID NO:66 (for porcine target), SEQ ID NO:70 (for avian target), SEQ ID NO:71 (for ovine target), or SEQ ID NO:67 (for primate target).

4. The composition of paragraph 3 wherein the one or more polypeptide is a Rabies G polypeptide, and the target animal is a canine or a feline.

5. The composition of paragraph 3 wherein the one or more polypeptide is a BTV polypeptide, and the target animal is a bovine or a sheep.

6. The composition of paragraph 3 wherein the one or more polypeptide is a FMDV polypeptide, and the target animal is a bovine or a porcine.

7. The composition of paragraph 3 wherein the one or more polypeptide is a PRRSV polypeptide, and the target animal is a porcine.

8. The composition of paragraph 3 wherein the one or more polypeptide is a PCV2 polypeptide, and the target animal is a porcine.

9. The composition of paragraph 3 wherein the one or more polypeptide is a leukemia virus polypeptide, and the target animal is a feline.

10. The composition of paragraph 3 wherein the one or more polypeptide is an influenza polypeptide, and the target animal is an equine, a canine, or a feline.

11. The composition of paragraph 3 wherein the one or more polypeptide is a WNV polypeptide, and the target animal is a canine or an equine.

12. The composition of paragraph 3 wherein the one or more polypeptide is capable of eliciting an immune response in an avian animal.

13. The composition of paragraph 12 wherein the polypeptide is from NDV, MDV, IBD, or IBDV.

14. The compositions of any one of paragraphs 1-4 wherein the expression vector is MDV, NDV, IBD, IBDV, adenovirus, adeno-like virus, or a herpesvirus.

15. The composition of paragraph 4 wherein the Rabies G polypeptide in encoded by the sequence as set forth in SEQ ID NO:5.

16. The composition of paragraph 4 wherein the OX40L polypeptide is at least 90% identical to the sequence as set forth in SEQ ID NO:12.

17. The composition of paragraph 13 wherein the OX40L polypeptide has the sequence as set forth in SEQ ID NO:12.

18. The composition of any one of paragraphs 1-4 wherein the expression vector is a recombinant poxviral vector.

19. The composition of paragraph 15 wherein the vector is canarypox.

20. The composition of paragraph 16 wherein the vector comprises the sequence as set forth in SEQ ID NO:23.

21. A vector comprising a polynucleotide encoding both:
   (a) one or more polypeptide selected from Rabies G Rabies G, an influenza, an FMDV, a BTV, a PCV2, a PRRSV, a WNV, a Nipah virus, a leukemia virus, a *leishmania* virus, an FIV, an FIPV, a FCV, an AHSV, a VSV, and an immunogenically effective variant or fragment thereof; and
   (b) an OX40L polypeptide, or a comparably adjuvanting variant or fragment thereof.

22. The vector of paragraph 21 wherein the OX40L polypeptide is at least 90% identical to the sequence as set forth in SEQ ID NO:12 (for canine target), SEQ ID NO:63 (for feline target), SEQ ID NO:64 (for equine target), SEQ ID NO:65 (for bovine target), SEQ ID NO:66 (for porcine target), or SEQ ID NO:71 (for ovine target).

23. The vector of paragraph 22 wherein the one or more polypeptide is a Rabies G polypeptide, and the target animal is a canine or a feline.

24. The vector of paragraph 22 wherein the one or more polypeptide is a BTV polypeptide, and the target animal is a bovine or a sheep.

25. The vector of paragraph 22 wherein the one or more polypeptide is a FMDV polypeptide, and the target animal is a bovine or a porcine.

26. The vector of paragraph 22 wherein the one or more polypeptide is a PRRSV polypeptide, and the target animal is a porcine.

27. The vector of paragraph 22 wherein the one or more polypeptide is a PCV2 polypeptide, and the target animal is a porcine.

28. The vector of paragraph 22 wherein the one or more polypeptide is a leukemia virus polypeptide, and the target animal is a feline.

29. The vector of paragraph 22 wherein the one or more polypeptide is an influenza polypeptide, and the target animal is an equine, a canine, or a feline.

30. The vector of paragraph 22 wherein the one or more polypeptide is a WNV polypeptide, and the target animal is a canine or an equine.

31. The vector of paragraph 23 wherein the Rabies G polypeptide is encoded by the sequence as set forth in SEQ ID NO:5.

32. The vector of paragraph 22 wherein the polynucleotide encodes a Rabies G polypeptide having the sequence as set forth in SEQ ID NO:1 and an OX40L polypeptide having at least 90% identity to the sequence as set forth in SEQ ID NO:12.

33. The vector of paragraph 21 wherein the vector is a poxvirus.

34. A method of vaccinating an animal comprising administering at least one dose of the composition of any one of paragraphs 1-14.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An immunogenically protective recombinant canarypox vector comprising and capable of expressing in vivo in an animal host in need thereof:
   a) two, three or four genes, separately inserted into the C3 and C5 arms of the vector, and each gene encoding the same immunogenic Rabies G polypeptide; and
   b) an OX40L gene, inserted into the C6 arm of the vector, and encoding an OX40L polypeptide, which when expressed in vivo in an animal host functions as an adjuvant for the in vivo-expressed immunogenic polypeptide(s).

2. The vector of claim 1, wherein the OX40L polypeptide is from the type of animal to which the vector is intended to be administered.

3. The vector of claim 2, wherein the OX40L polypeptide is at least 99% identical to the sequence as set forth in:
   a) SEQ ID NO:12 when the animal is a canine;
   b) SEQ ID NO:63 when the animal is a feline;
   c) SEQ ID NO:64 when the animal is an equine;
   d) SEQ ID NO:65 when the animal is a bovine;
   e) SEQ ID NO:66 when the animal is a porcine;
   f) SEQ ID NO:70 when the animal is an avian;
   g) SEQ ID NO:71 when the animal is an ovine; and,
   h) SEQ ID NO:67 when the animal is primate.

4. The vector of claim 3, wherein the OX40L polypeptide has the sequence as set forth in:
   a) SEQ ID NO:12 when the animal is a canine;
   b) SEQ ID NO:63 when the animal is a feline;
   c) SEQ ID NO:64 when the animal is an equine;
   d) SEQ ID NO:65 when the animal is a bovine;
   e) SEQ ID NO:66 when the animal is a porcine;
   f) SEQ ID NO:70 when the animal is an avian;
   g) SEQ ID NO:71 when the animal is an ovine; and,
   h) SEQ ID NO:67 when the animal is primate.

5. The vector of claim 2, wherein the animal is a canine or a feline.

6. The vector of claim 5, wherein when there are three or four genes encoding immunogenic polypeptides, at least one of the three or four genes contains a different polynucleotide sequence.

7. The vector of claim 5, wherein at least one of the two, three or four genes is codon-optimized; and wherein:

a) when there are two genes, the genes have the same or different nucleotide sequences;

b) when there are three genes, at least one of the genes has a different nucleotide sequence than the other two genes; and c) when there are four genes, at least two of the genes have a different nucleotide sequences than the other two genes.

8. The vector of claim 7, wherein the two, three or four genes encode a Rabies G polypeptide having the sequence as set forth in SEQ ID NO: 1.

9. The vector of claim 8, wherein the vector contains only two or only four Rabies G genes.

10. The vector of claim 9, wherein:

a) when there are only two Rabies G genes, either:

i) one of the genes has the sequence as set forth in SEQ ID NO: 5; and, the other gene has the sequence as set forth in SEQ ID NO:16; or ii) both of the genes have the sequence as set forth in SEQ ID NO: 5; or iii) both of the genes have the sequence as set forth in SEQ ID NO:16; and b) when there are four Rabies G genes, two of the genes have the sequence as set forth in SEQ ID NO: 5; and, the other two genes have the sequence as set forth in SEQ ID NO:16.

11. The vector of claim 10, wherein the OX40L gene encodes an OX40L polypeptide having a sequence that is at least 99% identical to the sequence as set forth in SEQ ID NO:12.

12. The vector of claim 11, wherein the OX40L gene encodes for an OX40L polypeptide having a sequence as set forth in SEQ ID NO:12.

13. The vector of claim 11, wherein the OX40L gene is inserted into the C6 locus, and wherein either:

a) only two Rabies G genes are present in the vector, wherein one Rabies G gene is inserted into each of the C5 loci;

b) only two Rabies G genes are present in the vector, wherein one Rabies G gene is inserted into each of the C3 loci; or c) only four Rabies G genes are present in the vector, wherein one Rabies G gene is inserted into each of the C5 loci, and a different Rabies G gene is inserted into each of the C3 loci.

14. The vector of claim 12, wherein the OX40L gene is inserted into the C6 locus, and wherein either:

a) only two Rabies G genes are present in the vector, wherein one Rabies G gene is inserted into each of the C5 loci;

b) only two Rabies G genes are present in the vector, wherein one Rabies G gene is inserted into each of the C3 loci; or c) only four Rabies G genes are present in the vector, wherein one Rabies G gene is inserted into each of the C5 loci, and a different Rabies G gene is inserted into each of the C3 loci.

15. The vector of claim 14, wherein the vector comprises the sequences as set forth in SEQ ID NOs: 9, 18, 19, 21, 4, 22, 24 and 15.

16. The vector of claim 14, wherein the vector comprises the sequences as set forth in SEQ ID NOs: 8, 9, 11, 14 and 15.

17. A method of vaccinating an animal in need of immunological protection comprising administering to the animal at least one dose of the composition of claim 1.

18. A method of vaccinating an animal in need of immunological protection comprising administering to the animal at least one dose of the composition of claim 14.

19. The method of claim 17, wherein the protection elicited by the administration lasts at least 1 year.

20. The method of claim 19, wherein the protection lasts at least 3 years.

* * * * *